(12) United States Patent
Zhou et al.

(10) Patent No.: US 11,473,140 B2
(45) Date of Patent: Oct. 18, 2022

(54) HIGHLY SELECTIVE OMEGA PRIMER AMPLIFICATION OF NUCLEIC ACID SEQUENCES

(71) Applicants: Xiaochuan Zhou, Houston, TX (US); Qi Zhu, Missouri City, TX (US); Nijing Sheng, Sugar Land, TX (US)

(72) Inventors: Xiaochuan Zhou, Houston, TX (US); Qi Zhu, Missouri City, TX (US); Nijing Sheng, Sugar Land, TX (US)

(73) Assignee: LC Sciences LC, Houston, TX (US)

( * ) Notice: Subject to any disclaimer, the term of this patent is extended or adjusted under 35 U.S.C. 154(b) by 0 days.

(21) Appl. No.: 14/554,966

(22) Filed: Nov. 26, 2014

(65) Prior Publication Data

US 2016/0068903 A1 Mar. 10, 2016

Related U.S. Application Data

(60) Provisional application No. 61/963,211, filed on Nov. 26, 2013.

(51) Int. Cl.
*C12Q 1/6876* (2018.01)
*C12Q 1/686* (2018.01)

(52) U.S. Cl.
CPC ........... *C12Q 1/6876* (2013.01); *C12Q 1/686* (2013.01)

(58) Field of Classification Search
CPC .... C12Q 1/6876; C12Q 1/686; C12Q 1/6832; C12Q 1/6853; C12Q 2525/101; C12Q 2525/119; C12Q 2525/161; C12Q 2525/186; C12Q 2525/197; C12Q 2525/30
See application file for complete search history.

(56) References Cited

U.S. PATENT DOCUMENTS

| 6,183,967 B1 * | 2/2001 | Jayasena | C07H 21/00 |
| | | | 435/194 |
| 6,627,748 B1 * | 9/2003 | Ju | B82Y 5/00 |
| | | | 435/4 |
| 6,692,915 B1 * | 2/2004 | Nallur | C12Q 1/6874 |
| | | | 435/173.1 |

(Continued)

FOREIGN PATENT DOCUMENTS

| WO | WO-2012126639 A1 * | 9/2012 | ........... C12Q 1/6853 |
| WO | WO-2012152708 A1 * | 11/2012 | ............. C07H 21/00 |
| WO | WO-2012153153 A1 * | 11/2012 | ........... C12Q 1/6851 |

OTHER PUBLICATIONS

SantaLucia, J. Proceedings of the National Academy of Sciences, USA 1998; 95: 1460-1465. (Year: 1998).*

(Continued)

*Primary Examiner* — Angela M. Bertagna
(74) *Attorney, Agent, or Firm* — G. Kenneth Smith

(57) ABSTRACT

The present invention relates to the field of nucleic acid sequence replication including PCR. Specifically, the present invention relates to methods and compositions for amplifying one or more target sequences from one or more template sequences. In particular, the present invention provides novel primer designs to enhance specificity of PCR reactions. The present invention also provides methods and compositions to perform the selection of specific sequence sections using specific primers and the amplification of all selected sequence sections using a pair of common primers in a single reaction tube.

1 Claim, 22 Drawing Sheets

Specification includes a Sequence Listing.

(56) References Cited

U.S. PATENT DOCUMENTS

| | | | | |
|---|---|---|---|---|
| 2008/0305478 | A1* | 12/2008 | Chun | C12Q 1/6848 |
| | | | | 435/6.11 |
| 2010/0062494 | A1* | 3/2010 | Church | C12Q 1/6855 |
| | | | | 435/91.52 |
| 2010/0086916 | A1* | 4/2010 | Mao | C07H 21/02 |
| | | | | 435/6.12 |
| 2010/0227320 | A1* | 9/2010 | Fu | C12Q 1/6858 |
| | | | | 435/6.12 |
| 2011/0008845 | A1* | 1/2011 | Kim | C12Q 1/686 |
| | | | | 435/91.2 |
| 2011/0195406 | A1* | 8/2011 | Sorenson | C12N 9/1252 |
| | | | | 435/6.1 |

OTHER PUBLICATIONS

Mitsuhashi, M. Journal of Clinical Laboratory Analysis 1996; 10: 277-284 (Year: 1996).*

Vestheim, H. and Jarman, S.N. Frontiers in Zoology 2008; 5: 12 (Year: 2008).*

* cited by examiner

SEQUENCE LISTING

```
<160> NUMBER OF SEQ ID NOS: 30

<210> SEQ ID NO 1
<211> LENGTH: 46
<212> TYPE: DNA
<213> ORGANISM: Artificial Sequence
<220> FEATURE:
<223> OTHER INFORMATION: Synthetic: lambda Prm 1

<400> SEQUENCE: 1
gttcagagtt ctacagtccg acgatcatac tcccgacaat ccccac          46

<210> SEQ ID NO 2
<211> LENGTH: 43
<212> TYPE: DNA
<213> ORGANISM: Artificial Sequence
<220> FEATURE:
<223> OTHER INFORMATION: Synthetic: lambda Prm 2

<400> SEQUENCE: 2
ccttggcacc cgagaattcc agtatgtcgc aggtaaaaag tgc             43

<210> SEQ ID NO 3
<211> LENGTH: 50
<212> TYPE: DNA
<213> ORGANISM: Artificial Sequence
<220> FEATURE:
<223> OTHER INFORMATION: Synthetic: Com prm 1

<400> SEQUENCE: 3
aatgatacgg cgaccaccga gatctacacg ttcagagttc tacagtccga       50

<210> SEQ ID NO 4
<211> LENGTH: 63
<212> TYPE: DNA
<213> ORGANISM: Artificial Sequence
<220> FEATURE:
<223> OTHER INFORMATION: Synthetic: Com prm 2

<400> SEQUENCE: 4
caagcagaag acggcatacg agatacatcg gtgactggag ttccttggca cccgagaatt    60
cca                                                         63

<210> SEQ ID NO 5
<211> LENGTH: 80
<212> TYPE: DNA
```

```
<213> ORGANISM: Artificial Sequence
<220> FEATURE:
<223> OTHER INFORMATION: Synthetic: Index 1

<400> SEQUENCE: 5
cgcatgtttg tttctttgct gccgtcttcc aggttcagag ttctacagtc cgacgatctt    60
gctttatctg ttcacttgtg                                                80

<210> SEQ ID NO 6
<211> LENGTH: 65
<212> TYPE: DNA
<213> ORGANISM: Artificial Sequence
<220> FEATURE:
<223> OTHER INFORMATION: Synthetic: Index 2

<400> SEQUENCE: 6
acaacctccg tcatgtgctg tgactgctcc ttggcacccg agaattccat gtagatggcc    60
atggc                                                                65

<210> SEQ ID NO 7
<211> LENGTH: 64
<212> TYPE: DNA
<213> ORGANISM: Artificial Sequence
<220> FEATURE:
<223> OTHER INFORMATION: Synthetic: Index 3

<400> SEQUENCE: 7
gcgatggtga gcagctgggg ctgggttcag agttctacag tccgacgatc agagacgaca    60
gggc                                                                 64

<210> SEQ ID NO 8
<211> LENGTH: 65
<212> TYPE: DNA
<213> ORGANISM: Artificial Sequence
<220> FEATURE:
<223> OTHER INFORMATION: Synthetic: Index 4

<400> SEQUENCE: 8
cccttaaccc ctcctcccag agacccacc ttggcacccg agaattccag ttgcaaacca     60
gacct                                                                65

<210> SEQ ID NO 9
<211> LENGTH: 78
<212> TYPE: DNA
<213> ORGANISM: Artificial Sequence
<220> FEATURE:
<223> OTHER INFORMATION: Synthetic: Index 5

<400> SEQUENCE: 9
gggcttctaa acaactcgcc ccactgcagg ttcagagttc tacagtccga cgatctgaaa    60
agagtctcaa acacaaac                                                  78

<210> SEQ ID NO 10
<211> LENGTH: 77
<212> TYPE: DNA
<213> ORGANISM: Artificial Sequence
<220> FEATURE:
<223> OTHER INFORMATION: Synthetic: Index 6

<400> SEQUENCE: 10
cttttagatc tgagatgcac aataaacagt tagccagagg ttccttggca cccgagaatt    60
ccatggcctg cttttgg                                                   77
```

<210> SEQ ID NO 11
<211> LENGTH: 85
<212> TYPE: DNA
<213> ORGANISM: Artificial Sequence
<220> FEATURE:
<223> OTHER INFORMATION: Synthetic: Index 7

<400> SEQUENCE: 11
ccaaaagcag taccatggac actggattaa gaagcaatgg ttcagagttc tacagtccga    60
cgatcccctc tcaagagaca aaaca                                         85

<210> SEQ ID NO 12
<211> LENGTH: 84
<212> TYPE: DNA
<213> ORGANISM: Artificial Sequence
<220> FEATURE:
<223> OTHER INFORMATION: Synthetic: Index 8

<400> SEQUENCE: 12
aacagtagac acaaaacagg ctcaggactt agcaaccttg gcacccagaa ttccagaagt    60
tatggaattc cttttattga aaca                                          84

<210> SEQ ID NO 13
<211> LENGTH: 83
<212> TYPE: DNA
<213> ORGANISM: Artificial Sequence
<220> FEATURE:
<223> OTHER INFORMATION: Synthetic: Index 9

<400> SEQUENCE: 13
agatagaagt ttggagagag aacgcggaat tggtctagtt cagagttcta cagtccgacg    60
acgatcggca actaccatcc agc                                           83

<210> SEQ ID NO 14
<211> LENGTH: 79
<212> TYPE: DNA
<213> ORGANISM: Artificial Sequence
<220> FEATURE:
<223> OTHER INFORMATION: Synthetic: Index 10

<400> SEQUENCE: 14
gggcagcaga gcttcttcta agtgcatttc tctcaccttg gcacccgaga attccatctg    60
tcacacaatg taattcagt                                                79

<210> SEQ ID NO 15
<211> LENGTH: 86
<212> TYPE: DNA
<213> ORGANISM: Artificial Sequence
<220> FEATURE:
<223> OTHER INFORMATION: Synthetic: Index 11

<400> SEQUENCE: 15
cctgtttata ctgagagcac tgatgataaa cacctcaatt gttcaggagt tctacagtcc    60
gacgatccca accacatttt ggacag                                        86

<210> SEQ ID NO 16
<211> LENGTH: 84
<212> TYPE: DNA
<213> ORGANISM: Artificial Sequence
<220> FEATURE:
<223> OTHER INFORMATION: Synthetic: Index 12

<400> SEQUENCE: 16
gttggtctct cttcttcttc atgctgttct tcttcagagt accttggcac ccgagaattc      60
caacgttcac tataattggt aggc                                              84

<210> SEQ ID NO 17
<211> LENGTH: 52
<212> TYPE: DNA
<213> ORGANISM: Artificial Sequence
<220> FEATURE:
<223> OTHER INFORMATION: Synthetic: APC1_R1

<400> SEQUENCE: 17
gttcagagtt ctacagtccg acgatcgaga gaacgcggaa ttggtctagg ca              52

<210> SEQ ID NO 18
<211> LENGTH: 50
<212> TYPE: DNA
<213> ORGANISM: Artificial Sequence
<220> FEATURE:
<223> OTHER INFORMATION: Synthetic: APC1_R2

<400> SEQUENCE: 18
ccttggcacc cgagaattcc aagtggtaga cccagaactt ctgtcttcct                 50

<210> SEQ ID NO 19
<211> LENGTH: 103
<212> TYPE: DNA
<213> ORGANISM: Artificial Sequence
<220> FEATURE:
<223> OTHER INFORMATION: Synthetic: MPL1_2_tile01_prm1_tube1

<400> SEQUENCE: 19
gagcttcggt tcacgcaatg ccgaagtctg accctttttg tctcctagcc gttctacagt      60
ccgacgatct ggatctcctt ggtagttgat ccggtcctag gca                       103

<210> SEQ ID NO 20
<211> LENGTH: 101
<212> TYPE: DNA
<213> ORGANISM: Artificial Sequence
<220> FEATURE:
<223> OTHER INFORMATION: Synthetic: MPL1_2_tile01_prm2_tube1

<400> SEQUENCE: 20
gagcttcggt tcacgcaatg acggaggatc tggggtcaca gagcgacctt ggcacccgag      60
aattccaacc aaggaatgcc tagttgatcc ggtcctaggc a                         101

<210> SEQ ID NO 21
<211> LENGTH: 20
<212> TYPE: DNA
<213> ORGANISM: Artificial Sequence
<220> FEATURE:
<223> OTHER INFORMATION: Synthetic: prepPrm1

<400> SEQUENCE: 21
gagcttcggt tcacgcaatg                                                  20

<210> SEQ ID NO 22
<211> LENGTH: 20
<212> TYPE: DNA
<213> ORGANISM: Artificial Sequence
<220> FEATURE:
<223> OTHER INFORMATION: Synthetic: prepPrm2
<220> FEATURE:
<221> NAME/KEY: modified_base

```
<222> LOCATION: (20)..(20)
<223> OTHER INFORMATION: dU

<400> SEQUENCE: 22
tgcctaggac cggatcaacu                                                    20

<210> SEQ ID NO 23
<211> LENGTH: 34
<212> TYPE: DNA
<213> ORGANISM: Artificial Sequence
<220> FEATURE:
<223> OTHER INFORMATION: Synthetic: prepPrm1

<400> SEQUENCE: 23
ttttcgcgtt agtatccgac cgatctacgt agcg                                    34

<210> SEQ ID NO 24
<211> LENGTH: 41
<212> TYPE: DNA
<213> ORGANISM: Artificial Sequence
<220> FEATURE:
<223> OTHER INFORMATION: Synthetic: prepPrm2

<400> SEQUENCE: 24
ttttgaccgt actatcgaac cgtcgtacta gctcttcgcg t                            41

<210> SEQ ID NO 25
<211> LENGTH: 121
<212> TYPE: DNA
<213> ORGANISM: Artificial Sequence
<220> FEATURE:
<223> OTHER INFORMATION: Synthetic: APC_1_chr5_112173790_p1

<400> SEQUENCE: 25
atccgaccga tctacgtagc gggcaacatg actgtccttt caccatattt gaatactcgt        60
tcagagttct acagtccgac gatcacagtg ttacccagca cgcgaagagc tagtacgacg       120
g                                                                      121

<210> SEQ ID NO 26
<211> LENGTH: 107
<212> TYPE: DNA
<213> ORGANISM: Artificial Sequence
<220> FEATURE:
<223> OTHER INFORMATION: Synthetic: APC_1_chr5_112173944_p2

<400> SEQUENCE: 26
atccgaccga tctacgtagc gggtatgaat ggtgacactt cttccatgac tttccttggc        60
acccgagaat tccaggcaat ctgggacgcg aagagctagt acgacgg                    107

<210> SEQ ID NO 27
<211> LENGTH: 98
<212> TYPE: DNA
<213> ORGANISM: Artificial Sequence
<220> FEATURE:
<223> OTHER INFORMATION: Synthetic: APC_1_chr5_112173790_p1_no p3 flank

<400> SEQUENCE: 27
tccgaccgat ctacgtagcg ggcaacatga ctgtcctttc accatatttg aatactcgtt        60
cagagttcta cagtccgacg atcacagtgt tacccagc                               98

<210> SEQ ID NO 28
<211> LENGTH: 86
<212> TYPE: DNA
```

```
<213> ORGANISM: Artificial Sequence
<220> FEATURE:
<223> OTHER INFORMATION: Synthetic: APC_1_chr5_112173944_p1_no p3 flank

<400> SEQUENCE: 28
tccgaccgat ctacgtagcg ggtatgaatg gctgacactt cttccatgac tttccttggc    60
acccgagaat tccaggcaat ctgggc                                         86

<210> SEQ ID NO 29
<211> LENGTH: 61
<212> TYPE: DNA
<213> ORGANISM: Artificial Sequence
<220> FEATURE:
<223> OTHER INFORMATION: Synthetic: comPrm1

<400> SEQUENCE: 29
aagatacggc gaccaccgag atctacacat gatgacacac gttcagagtt ctacagtccg    60
a                                                                    61

<210> SEQ ID NO 30
<211> LENGTH: 63
<212> TYPE: DNA
<213> ORGANISM: Artificial Sequence
<220> FEATURE:
<223> OTHER INFORMATION: Synthetic: comPrm2

<400> SEQUENCE: 30
caagcagaag acggcatacg agatgaagat agtgactgga gttccttggc accgagaatt    60
cca                                                                  63
```

HIGHLY SELECTIVE OMEGA PRIMER AMPLIFICATION OF NUCLEIC ACID SEQUENCES

PRIOR APPLICATIONS

This application claims priority to U.S. Ser. No. 61/963,211 filed Nov. 26, 2013, which is hereby incorporated in its entirety into this application.

FIELD OF INVENTION

The present invention relates to the field of nucleic acid sequence replication including PCR. Specifically, the present invention relates to methods and compositions for amplifying one or more target sequences from one or more template sequences. In particular, the present invention provides novel primer designs to enhance specificity of PCR reactions. The present invention also provides methods and compositions to perform the selection of specific sequence sections using specific primers and the amplification of all selected sequence sections using a pair of common primers in a single reaction tube.

BACKGROUND

Many biological and biomedical applications, such as genetic disease screening, personal medicine, forensic tests, and targeted sequencing, require replication and/or amplification of one or more selected nucleic acid sequence sections from a large pool of nucleic acid sequences, such as genomic DNA from various living cells, nucleic acid sequence mixtures from metagenomic samples, and microbiome DNA from intestinal flora. PCR is a powerful tool to selectively amplify the nucleic acid sequences of interest in a nucleic acid mixture. For applications involving multiple sequences of interest multiplex PCR has been widely applied. Multiplexing PCR was first reported in 1988 by Chamberlain et al in "Deletion screening of the Duchenne muscular dystrophy locus via multiplex DNA amplification" (1988) Nucleic Acids Res. 16: 11141-11156. However, conventional multiplex PCR is generally considered difficult to perform on more than a few dozen targets per reaction due to the requirement of significant optimization efforts that are described by Henegariu et al. (1997) "Multiplex PCR: Critical Parameters and Step-by-Step Protocol" BioTechniques 23: 504-511. The main challenges with multiplex PCR include the formation of primer-dimers, non-uniform amplification of targets, and high rates of mispriming events, as described by Edwards et al. (1994) "Multiplex PCR: advantages, development, and applications" Genome Res. 3:S65-75.

For the purpose of unifying primer-dependent PCR conditions, a variation of multiplex PCR has been described by A. P. Shuber et al. (1995) "A Simplified Procedure for Developing Multiplex PCRs" Genome Res. 5: 488-493. Chimeric primers each containing a 3' region complementary to sequence-specific recognition sites and a 5' region made up of an unrelated 20-nucleotide sequence are used in multiplex PCR. Identical reaction conditions, cycling times, and annealing temperatures were demonstrated for any PCR primer pair comprising the chimeric motif. This method was said to have helped eliminating the multiple optimization steps involved in developing multiplex PCR. However, the adjustment of individual primer concentrations was still required. The present invention provides a solution to eliminate the requirement for the individual primer concentration adjustment.

For the purposes of reducing primer-dimer formation and reducing mispriming events, variations of multiplex PCR have been reported. Z. Lin et al. (1996), in "Multiplex genotype determination at a large number of gene loci" Proc. Natl. Acad. Sci. 93: 2582-2587, described a method of converting multiplex amplification into uniplex amplification so as to reduce primer-primer interaction. The process to implement the method consists of three separate PCR rounds. In the first two PCR rounds locus specific primers containing 5' universal tails or tags are used to attach the universal tails to the target sequences. Then, in round 3, all the universal tail tagged targets (26 genetic loci) are amplified simultaneously using one pair of universal primers that are sequence-matched to the universal tails. Round 1 and round 2 are similar to conventional multiplex PCR runs and a time-consuming optimization process involving primer concentration adjustments is required. Additionally, the workflow consists of multiple hands-on steps including three separate PCR rounds and PCR product purifications between the PCR rounds. As comparison, the present invention provides a significantly simplified workflow.

A DNA typing method, Minisatellite Variant Repeat mapping by PCR (MVR-PCR), is described by A. J. Jeffreys et al. (1991) "Minisatellite repeat coding as a digital approach to DNA typing" Nature 354:204-209. Each PCR reaction includes three primers: a 5' tagged variant repeat specific primer at a low concentration of 10 to 20 nM, a minisatellite flanking primer at a high concentration of 1 μM, and a tag primer that has a sequence matching to the tagged section of the variant repeat specific primer at a high concentration of 1 μM. The flanking primer has a sequence matches to a flanking section of the minisatellite region. Recombinant Taq polymerase, AmpliTaq (Perkin-Elmer-Centus) is used. PCR reactions are cycled for 1.3 min denaturation at 96° C., 1 min annealing at 68° C., and 5 min extension at 70° C. for 18 cycles, followed by a chase for 1 min at 67° C., and 10 min at 70° C. for 2 cycles on a DNA thermal cycler. In one reaction run more than 50 amplicons of different lengths were produced each representing the distance between a specific variant repeating unit and the flanking site. The production of the amplicons starts in a thermo cycle with the annealing of the variant repeat specific primers to matching variant repeat units of the minisatellite region of a sample DNA. The annealed specific primers are then extended beyond the flanking site forming the first extension products by polymerase extension reaction. In the next thermo cycle, the flanking primers are annealed to the first extension products and are extended creating the second extension products with ends complementary to tag sequence. From the next thermo cycle on the high concentration flank primers and the tag primers work as a pair on the second extension products to efficiently generate PCR products. Occasional internal priming off the PCR products by the specific primers generates authentic shorter PCR products. This is the first work to demonstrate the feasibility of tag-driven PCR by incorporating the tag primer at a higher concentration relative to the tagged specific primer. On the other hand, the described approach is designed to reveal the patterns of repeating sequence units that share one target specific primer. Together only three primers were used in each PCR reaction mixture. The work does not provide any obvious solution on how to handle a general type of multiplex PCR in which multiple target specific primers are involved and primer-dimer formation must be minimized.

J. Brownie et al. (1997), in "the elimination of primer-dimer accumulation in PCR" Nucleic Acids Res. 25: 3235-3241, described a Homo-Tag Assisted Non-Dimer System (HANDS) to reduce the formation primer-dimers. Multiple tagged genome-specific primers at low concentrations and a single Tag or common primer at a high concentration are used. Similar to Jeffreys method above, the Tag primer has the same sequence as that of the 5' tail portion of the tagged genome-specific primers. The authors suggested designing the genome-specific primers such that the Tm (melting temperature) of the Tag annealed to its complementary sequence is higher than that of the genome-specific primed duplex. This design enables a switch from genomic priming by the genome-specific portions of the genome-specific primers at a low annealing temperature to tail priming by the Tag at an elevated annealing temperature. After two cycles of genomic priming, the complement of Tag sequence is incorporated into the amplicon ends. Then the annealing temperature is raised and subsequent amplifications are largely driven by the Tag primers. All the amplicons produced have the same pair of complementary ends. When the amplicons are short (100 to 120 nucleotides), as with primer-dimers, the complementary ends tend to gives rise to hairpin structures. The formation of these hairpin structures out-competes the annealing of further tag primers thereby preventing the accumulation of non-specific primer-dimer products.

A drawback of HANDS method is the product yield reduction of short on-target sequences. By design the method inhibits the amplification of short sequences no matter if they are unwanted primer dimers or wanted on-target sequences. Indeed the reported data reveals a pattern of significantly reduced product yields as the lengths of on-target products decreased from 550 to 300 nucleotides. This makes the method inadequate for applications involving on-target amplicon length below 300 nucleotides. Such applications include sequence enrichment for highly parallel sequencing uses.

Taq polymerase was used in both methods described by Jeffreys and Brownie shown above. Taq polymerase has a well-known 5'-3' endonuclease activity (P. M. Holland et al. (1991) "Detection of specific polymerase chain reaction product by utilizing the 5'-3' exonuclease activity of *Thermus aquaticus* DNA polymerase" Proc. Natl. Acad. Sci. 88 7276-7280) and 5' flap endonuclease activity (V. Lyamichev et al. (1993) "Structure-specific endonucleolytic cleavage of nucleic acids by eubacterial DNA polymerases" Science 260:778-783). These nuclease activities cause degradation of double-stranded DNA that the polymerase encounters while extending a DNA fragment. This imposes limitations on applications where two or more target regions are in tandem or in positional proximity. Primers hybridized to the middle of the tandem regions have high probability of being degraded and failing to produce desired amplicons. Such phenomenon is indeed observed in the data presented in the above Jeffreys' publication. One aspect of the present invention is to overcome this limitation by utilizing newly available polymerases that lack 5'-3' exonuclease activity and strand displacement activity.

Another tag-driven PCR method for multiplex amplification applications is disclosed in B. Frey et al. (2013) "Methods and amplification of target nucleic acids using a multi-primer approach" US Patent Application Publication US 2013/00045894 A1. Similar to the methods of Jeffreys and Brownie, two sets of primers including tagged target specific primers and common primers are used to amplify target nucleic acids in a single amplification reaction. A distinct reaction condition feature is that specific primer set concentration is suggested to be the same or higher than that of common primer set. Consequently, reaction product contains shorter sequences flanked by the tagged specific primers and longer sequences flanked by the common primers at comparable concentration levels. The authors suggest separating the longer sequences (the desired product) from the shorter sequences (undesired product) before being used for corresponding applications. The present invention identified significantly different reaction conditions that result in clean products overwhelmingly dominated by the desired full length sequences.

The advances of high multiplex nucleic acid detection technologies such as microarray and massively parallel sequencing have made it possible to analyze hundreds, thousands, and up to millions of nucleic sequences in one test run. Successful applications of these detection technologies often share a common feature in that there is a requirement for an amplification of the regions of interests prior to actual detections. High multiplex amplification using surface immobilized primer pairs has been described in various publications including A. Pemov et al. (2005) "DNA analysis with multiplex microarray-enhanced PCR", Nucleic Acids Res. 33: e11; L. S. Meuzelaar et al. (2007) "MegaPlex PCR: a strategy for multiplex amplification", Nat. Methods 4: 835-837; and references quoted therein. Multiple target specific primer pairs are immobilized either to a solid surface or inside a gel matrix through their 5' ends. The immobilization is said to help avoid primer-dimer formation due to physical separation of the primers. Each primer consists of a target specific priming section on 3' side and a common priming section at 5' side. The immobilized primers are used to selectively replicate target sequences and to incorporate common priming sections into the replicated sequences in a solid-phase PCR process. Then a pair of common primers is used to amplify the solid-phase PCR products. The use of a single common primer pair eliminates target specific primer related amplification biases. However, the use of solid phase PCR complicates process workflows. A simpler method is desirable.

Solution phase multiplex PCR using cleavable primers have been described in K. E. Varley et al. (2008) "Nested Patch PCR enables highly multiplexed mutation discovery in candidate Genes" Genome Res. 18:1844-1850. The method relies on two rounds of target-specific enrichment. First, primer pairs are designed against each target, and the mixture of primers used for a predetermined number of cycles of multiplex PCR. The primers contain uracil bases in place of thymine, such that post-amplification exposure to uracil DNA glycosylase, endonuclease VIII, and Exonuclease I effectively removes the primer regions from amplicons. For the second round of selection, Nested Patch adaptors are used. These adaptors consist of a double-stranded universal segment and a single-stranded overhang that is target specific. Hybridization and ligation of Nested Patch adaptors to primer-depleted amplicons is followed by multi-template PCR amplification with primers corresponding to the universal sequences. Because this ligation is dependent on sequences immediately internal to the original primers used in the limited multiplex PCR, the Nested Patch adaptors confer additional specificity. A variation of the method is describe by J. Leamon et al. (2012) "Methods and compositions for multiplex PCR" US Patent Application Publication US 2012/0295819 A1. The method omits the second round of selection by attaching common adapters using blunt end ligation. These two versions of the method share a similar workflow requiring multiple hands-on steps.

Additionally, amplifications of individual targets in the first round multiplex PCR are carried out by individual target specific primers. Inevitably primer related yield differences are exponentially amplified as the number of thermo cycles increases. This leads to non-uniform amplification of targets. One aspect of the present invention is to provide a simple workflow and to achieve uniform high multiplex amplification in solution phase.

Lane 1: Regular PCR, specific primer 1&2=500 nM, lambda DNA=10 fM

Lane 2: Relay PCR, specific primer 1&2=5 nM, common primer 1&2=500 nM, lambda DNA=10 fM Lane 3: Relay PCR, specific primer 1&2=0.5 nM, common primer 1&2=500 nM, lambda DNA=10 fM Lane L: is a DNA ladder run showing the sizes (in base pair or bp) of corresponding markers.

Figure 17:
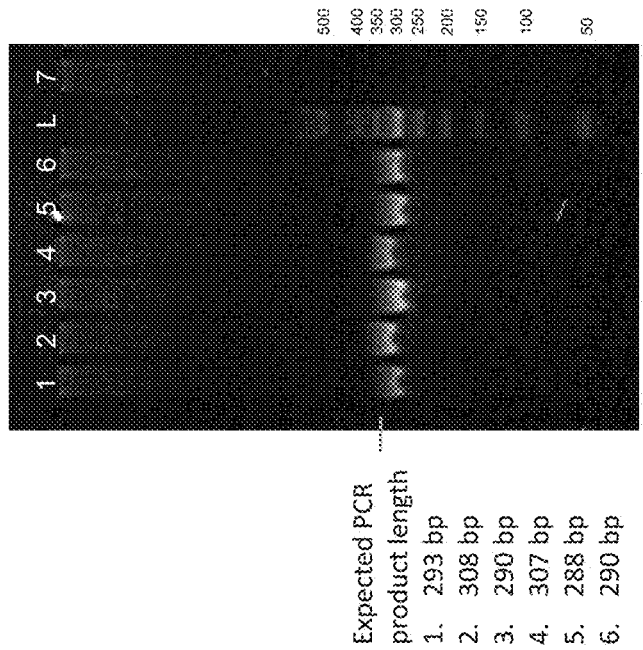

FIG. 17 shows agarose gel electrophoresis image of example relay PCR using omega primers on a human genomic DNA sample. Lane 1 through lane 6 shows the products of six individual PCR runs each involving a pair of omega primers of a unique target region as shown in corresponding table in Experiment II. The same common primer pairs were used in all six PCR runs. Lane 7 shows the result of no-specific primer control run. Lane L is a DNA ladder showing the sizes (in base pair or bp) of corresponding markers.

Figure 5:
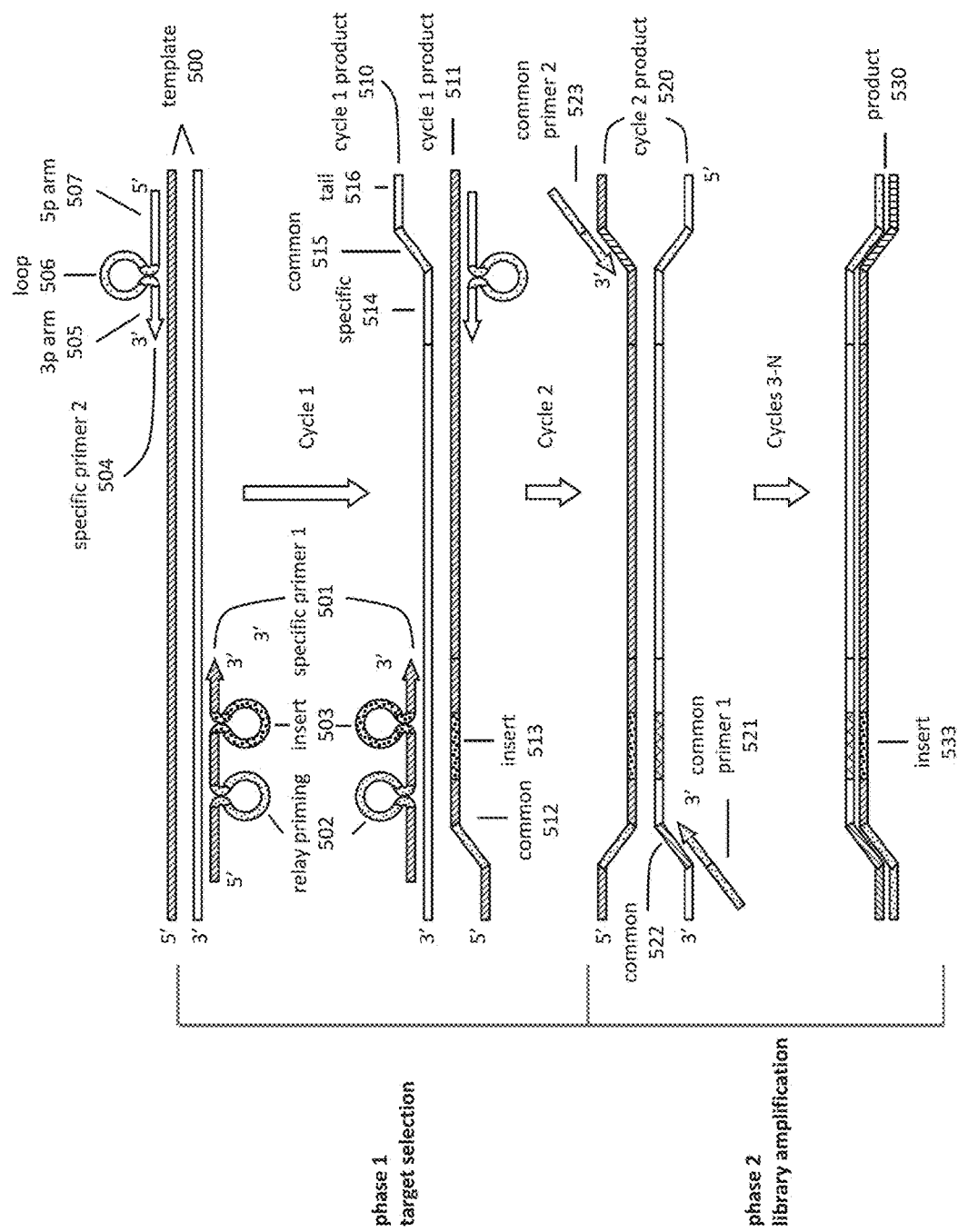
FIG. 5 schematically outlines an exemplary embodiment of relay PCR method using multi-loop omega specific primers.
Figure 18:
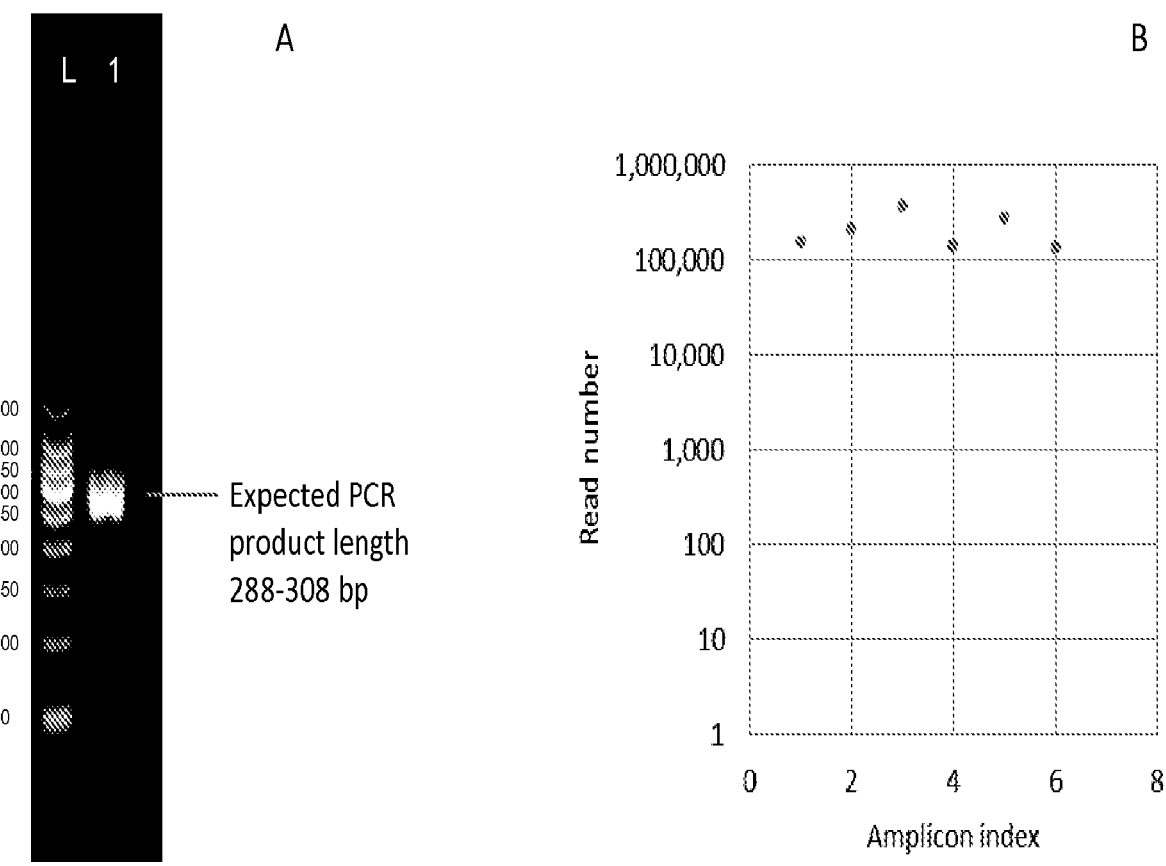

FIG. 18 shows the experimental results of a multiplex relay PCR using omega primers. A. shows agarose gel electrophoresis image of an example multiplex relay PCR using omega primers on a human genomic DNA sample. Lane 1 shows the product of a multiplex PCR run, which include 6 pairs of omega primers and one pair common primers that are used in the individual relay PCR runs of FIG. 5. Lane L is a DNA ladder showing the sizes (in base pair or bp) of corresponding markers. B. shows a scatter plot of the sequencing read number distribution of the 6 expected amplicons.

Figure 19:
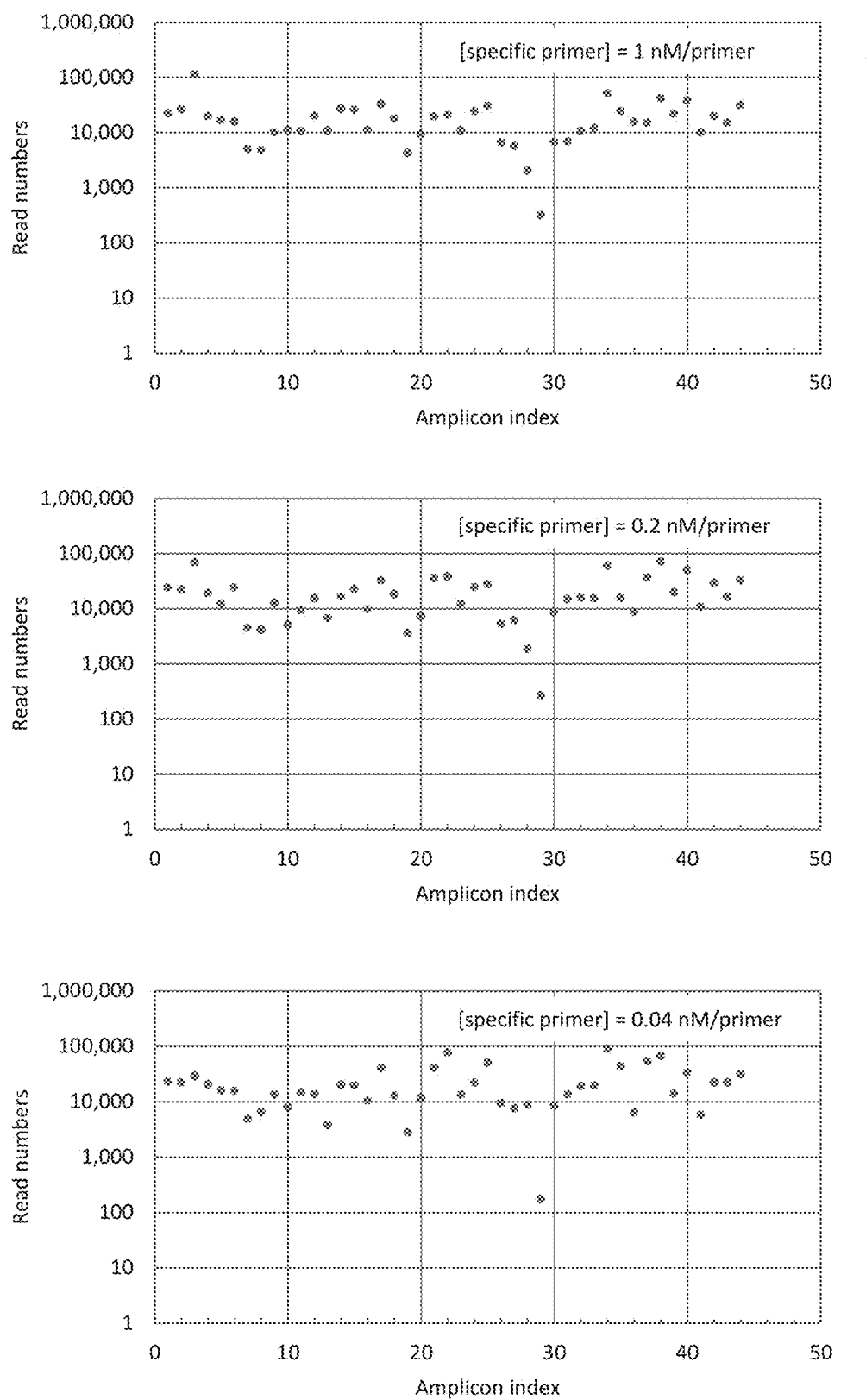

FIG. 19 shows high-throughput sequencing measurement results of amplicon read number distributions in multiplex PCR products. Figures A, B, and C are obtained by using specific omega primer concentrations of 1 nM, 0.2 nM, and 0.04 nM per primer, respectively.

Figure 20:
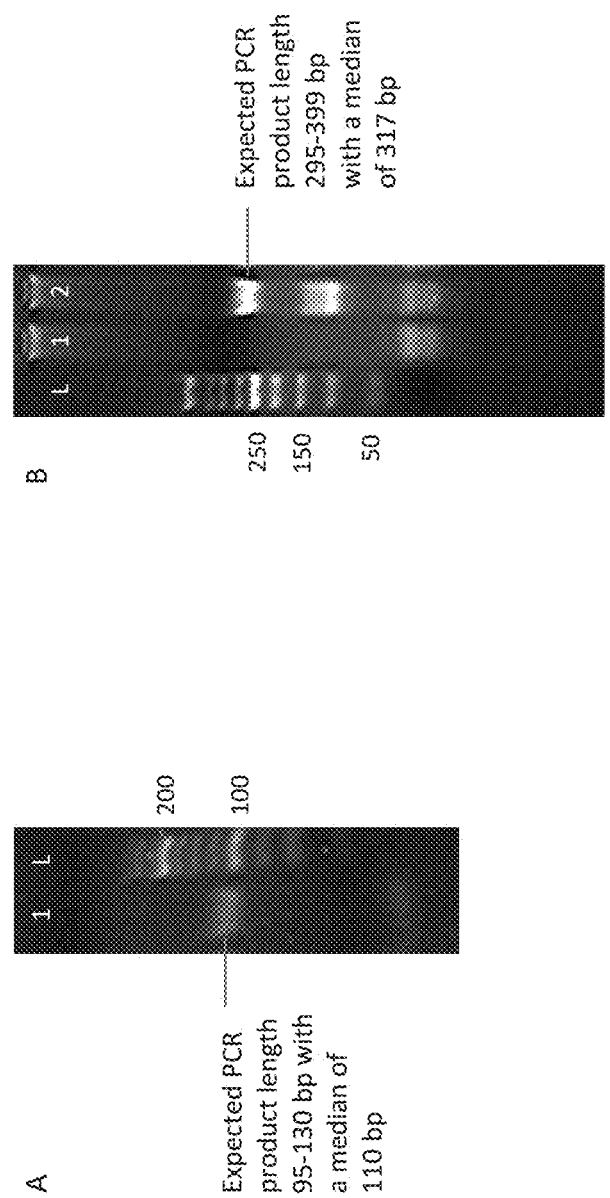

FIG. 20 shows the experimental results of multiplex relay PCR using omega primers derived from microarray synthesized oligonucleotides. A. shows an agarose gel electrophoresis image of a PCR product of microarray synthesized primer precursor templates. Lane 1 is the PCR product of a mixed template pool 204 oligonucleotide sequences. Lane L is a DNA ladder showing the sizes (in base pair or bp) of corresponding markers. B. shows an agarose gel electrophoresis image of a multiplex relay PCR product using the microarray derived primer precursor mixture of FIG. 20A on a human genomic DNA sample. Lane 1 shows the product of the multiplex PCR run. Lane L is a DNA ladder showing the sizes (in base pair or bp) of corresponding markers.

Figure 21:
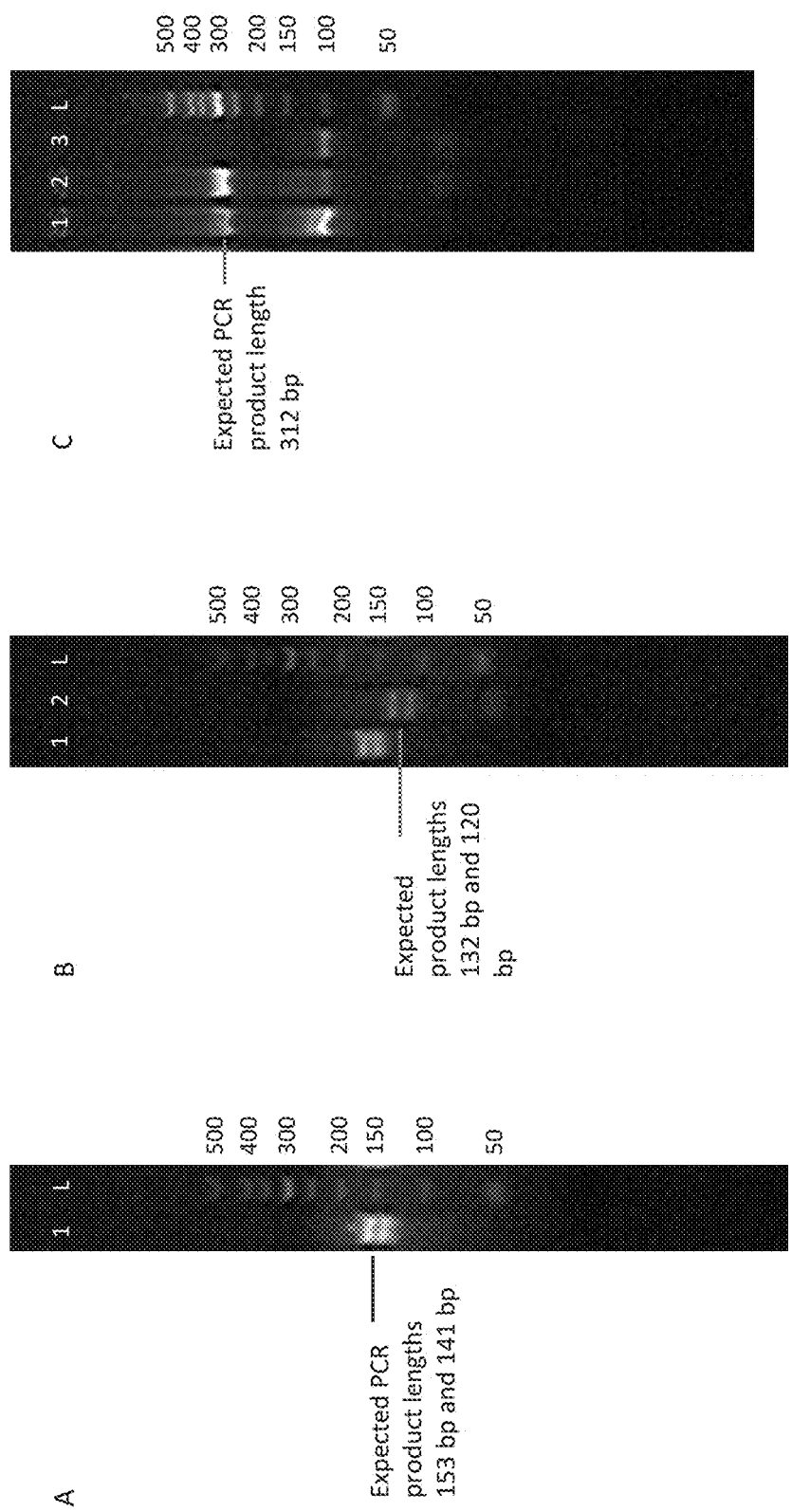

FIG. 21 shows the experimental results of enzymatic preparation of specific primers and the use of the specific primers in multiplex relay PCR. A. shows an agarose gel electrophoresis image of PCR products of specific primer templates. Lane 1 is the PCR products of mixed templates. Lane L is a DNA ladder showing the sizes (in base pair or bp) of corresponding markers. B. lane 2 shows the gel image of restriction enzyme digestion products. Lane 1 shows the original PCR product before restriction enzyme digestion. Lane L is a DNA ladder showing the sizes (in base pair or bp) of corresponding markers. C. shows the images of relay PCR products. Lane 1 shows the result of the positive control derived from chemically synthesized specific primers. Lane 2 is the relay PCR products derived from enzymatically prepared specific primers. Lane 3 is the result of negative control. Lane L is a DNA ladder showing the sizes (in base pair or bp) of corresponding markers.

DEFINITIONS

Term "tube" refers to a vessel in which PCR or any other types of bimolecular reactions take place. The "tube" may be made of plastic and in form of micro tubes or Eppendorf tubes. The "tube" may also be made of glass, silicone, silicon, and metals and be a part of microfabricated devices.

Terms "target", "target sequence", and their derivatives refer to any single or double-stranded nucleic acid sequence that is suspected or expected to be present in a sample and is designated to be selected, analyzed, examined, probed, captured, replicated, synthesized, and/or amplified using any appropriate methods.

Term "library", "DNA library" and their derivatives, as used herein, refer to a collection of DNA fragments or DNA sequences that is subject to parallel sample preparation and/or parallel detection assay processes. In some embodiments, such as multiplex amplification, target sequences are selectively amplified using target specific primers and form a target sequence library.

Term "sample" refers to any specimen, culture and the like that is suspected of including a target. The sample can include any biological, clinical, surgical, agricultural, atmospheric or aquatic-based specimen containing one or more nucleic acids. The sample can include any type of specimens such as cheek tissue, whole blood, dried blood spot, organ tissue, plasma, urine, feces, skin, and hair. The term also includes any isolated nucleic acid sample such as genomic DNA from fresh-frozen or formalin-fixed paraffin-embedded tissues.

Terms "synthesize", "synthesizing", and their derivatives refer generally to a reaction involving nucleotide polymerization by a polymerase, optionally in a template-dependent fashion. Polymerases synthesize an oligonucleotide via transfer of a nucleoside monophosphate from a nucleoside triphosphate (NTP), deoxynucleoside triphosphate (dNTP), or dideoxynucleoside triphosphate (ddNTP) to the 3' hydroxyl of an extending oligonucleotide chain. For the purposes of this disclosure, synthesizing includes the serial extension of a hybridized primer via transfer of a nucleoside monophosphate from a deoxynucleoside triphosphate.

Terms "oligo", "oligonucleotide", and their derivatives refer to short, single-stranded nucleic acid sequences including DNA, RNA, DNA-RNA hybrid, and various modification group containing molecules. They can be produced or synthesized by chemical methods, enzymatic methods, or combinations of chemical and enzymatic methods.

Term "extension" and its variants, as used herein, when used in reference to a given primer, comprise any in vivo or in vitro enzymatic activity characteristic of a given polymerase that relates to polymerization of one or more nucleotides onto an end of an existing nucleic acid molecule. Typically but not necessarily such primer extension occurs in a template-dependent fashion; during template-dependent extension, the order and selection of bases is driven by established base pairing rules, which can include Watson-Crick type base pairing rules or alternatively (and especially in the case of extension reactions involving nucleotide analogs) by some other type of base pairing paradigm. In one non-limiting example, extension occurs via polymerization of nucleotides on the 3'OH end of the nucleic acid molecule by the polymerase.

Terms "amplify", "amplifying", "amplification", and their derivatives refer generally to any action or process whereby at least a portion of a nucleic acid molecule (referred to as a template nucleic acid molecule) is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. In some embodiments, amplification includes a template-dependent in vitro enzyme-catalyzed reaction for the production of at least one copy of at least some portion of the nucleic acid molecule or the production of at least one copy of a nucleic acid sequence that is complementary to at least some portion of the nucleic acid molecule. Amplification optionally includes linear or exponential replication of a nucleic acid molecule. In some embodiments, such amplification is performed using isothermal conditions; in other embodiments, such amplification can include thermocycling. In some embodiments, the amplification is a multiplex amplification that includes the simultaneous amplification of a plurality of target sequences in a single amplification reaction. At least some of the target sequences can be situated on the same nucleic acid molecule or on different target nucleic acid molecules included in the single amplification reaction. In some embodiments, "amplification" includes amplification of at least some portion of DNA- and RNA-base nucleic acids alone, or in combination. The amplification reaction can include single or double-stranded nucleic acid substrates and can further including any of the amplification processes known to one of ordinary skill in the art. In some embodiments, the amplification reaction includes polymerase chain reaction (PCR).

Term "primer" and its derivatives refer to any polynucleotide or oligonucleotide that can hybridize to a target sequence of interest. In some embodiments of this disclosure, at least 3' end portion of a primer is complementary to a portion of the target sequence. Typically, the primer acts as a point of initiation for amplification or synthesis when exposed to amplification or synthesis conditions; such amplification or synthesis can occur in a template-dependent fashion and optionally results in formation of a primer extension product that is complementary to at least a portion of the target sequence. Exemplary amplification or synthesis conditions can include contacting the primer with a polynucleotide template (e.g., a template including a target sequence), nucleotides and an inducing agent such as a polymerase at a suitable temperature, salt concentration, and pH to induce polymerization of nucleotides onto an end of the target-specific primer. A primer can be paired with a compatible primer within an amplification or synthesis reaction to form a primer pair consisting of a forward primer and a reverse primer. In some embodiments, the forward primer includes a 3' portion substantially complementary to at least a portion of a strand of a nucleic acid molecule and the reverse primer includes a 3' portion substantially identical to at least of portion of the strand. In some embodiments, the forward primer and the reverse primer are capable of hybridizing to opposite strands of a nucleic acid duplex. Optionally, the forward primer primes synthesis of a first nucleic acid strand, and the reverse primer primes synthesis of a second nucleic acid strand, wherein the first and second strands are substantially complementary to each other, or can hybridize to form a double-stranded nucleic acid molecule.

Term "specific primer" and "target-specific primer" refer to a single stranded oligonucleotide that includes a 3' specific section that is substantially complementary or substantially identical to at least a portion of a nucleic acid molecule that includes a target sequence. In some embodiments, the specific primer includes two or more specific sections that are substantially complementary or substantially identical to portions of a nucleic acid molecule that includes a target sequence. In some embodiments, the specific primer includes at least a common segment. The common segment is a sequence segment that is designed to be shared in plurality of primers. In some embodiments, the common segment is located between two specific sections. In some embodiments, the common segment is located at 5' end portion of the specific primer.

Term "common primer" and "library primer" refer to a single stranded oligonucleotide that includes a 3' section that is substantially complementary or substantially identical to at least a portion of a common segment of a nucleic acid molecule. In some embodiments, the common segment of the nucleic acid molecule is in a PCR product of a target sequence. In some embodiments, the common segment of the nucleic acid molecule is in a primer extension product of a target sequence.

Term "hybridization" is consistent with its use in the art, and generally refers to the process whereby two nucleic acid molecules undergo base pairing interactions. Two nucleic acid molecules are said to be hybridized when any portion of one nucleic acid molecule is base pared with any portion of the other nucleic acid molecule; it is not necessarily required that the two nucleic acid molecules be hybridized across their entire respective lengths and in some embodiments, at least one of the nucleic acid molecules can include portions that are not hybridized to the other nucleic acid molecule.

Term "polymerase chain reaction" or "PCR" refers to the method of K. B. Mullis U.S. Pat. Nos. 4,683,195 and 4,683,202, hereby incorporated by references, which describe a method for increasing the concentration of a segment of a polynucleotide of interest in a mixture of genomic DNA without cloning of purification. This process of amplifying the polynucleotide of interest consists of introducing a large excess of two oligonucleotide primers to the DNA mixture containing the desired polynucleotide of interest, followed by a precise sequence of thermal cycling in the presence of a DNA polymerase. The two primers are complementary to their respective strands of the double stranded polynucleotide of interest. To effect amplification, the mixture is denatured and the primers then annealed to their complementary sequences within the polynucleotide of interest molecules. Following annealing, the primers are extended with a polymerase to form a new pair of complementary strands. The steps of denaturation, primer annealing and polymerase extension can be repeated many times (i.e., denaturation, annealing and extension constitute one "cycle", there can be numerous "cycles") to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified".

Term "single-strand PCR" and "linear amplification reaction" refer to an amplification reaction that uses only one primer per primer specific sequence set. The "primer specific sequence" refers to a nucleic acid sequence containing at least one primer complementary section. A primer specific sequence set contains one or more primer specific sequences.

Term "polymerase" and its derivatives generally refer to any enzyme that can catalyze the polymerization of nucleotides into a nucleic acid strand. Typically but not necessarily, such nucleotide polymerization can occur in a template-dependent fashion. Such polymerase can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerases, or the linkage of parts of two or more polymerases. Some exemplary polymerases include without limitation DNA polymerases and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a reporter enzyme or a processivity-enhancing domain. Optionally, the polymerase can possess 5' exonuclease activity or terminal transferase activity. In some embodiments, the polymerase can be optionally reactivated, for example through the use of heat, chemicals or re-addition of new amounts of polymerase into a reaction mixture. In some embodiments, the polymerase can include thermo stable, hot-start, high-fidelity, 3' to 5' nuclease activity, 5' to 3' nuclease activity, and strand displacement activity.

Term "multiplex amplification", "multiplex PCR" and their derivatives refer to selective and non-random amplification of two or more target sequences within a sample using at least one target specific primer. In some embodiments, multiplex amplification is performed such that some or all of the target sequences are amplified within a single reaction vessel. The "plexity" or "plex" of a given multiplex amplification refers generally to the number of different target-specific sequences that are amplified during that single multiplex amplification.

Term "GC content" refers to the cytosine and guanine content of a nucleic acid molecule.

Term "DNA barcode" and its derivatives, refers generally to a unique short (4-14 nucleotide) nucleic acid sequence within a common primer that can act as a 'key' to distinguish or separate a plurality of amplified target sequences in a sample.

Term "complementary" and "complement" and their variants refer to any two or more nucleic acid sequence (e.g., portions or entireties of template nucleic acid molecules, target sequence and/or primers) that can undergo cumulative base pairing at two or more individual corresponding positions in antiparallel orientation, as in a hybridized duplex. Such base pairing can proceed according to any set of established rules, for example according to Watson-Crick base pairing rules or according to some other base pairing paradigm. Optionally there can be "complete" complementarity between a first and a second nucleic acid sequence where each nucleotide in the first nucleic acid sequence can undergo a stabilizing base pairing interaction with a nucleotide in the corresponding antiparallel position on the second nucleic acid sequence. "Partial" complementarity describes nucleic acid sequences in which at least 20%, but less than 100%, of the residues of one nucleic acid sequence are complementary to residues in the other nucleic acid sequence. "Partial" complementarity also describes nucleic acid sequences in which at least 20%, but less than 100%, of the residues of a section of interest of one nucleic acid sequence are complementary to residues in the other nucleic acid sequence.

Term "association fraction", "binding coefficient", "fraction of binding", and their derivatives refer to the fraction of a template being hybridized with corresponding primer, a target being hybridized with corresponding probe, or one section being hybridized with another section of the same nucleic acid sequence. The calculation of the association fraction is described by Miura (Miura el al. (2005) "A novel strategy to design highly specific PCR primers based on the stability and uniqueness of 3'-end subsequences" Bioinformatics 21 4363-4370) and in specifications of this disclosure.

Term "parallel sequencing", "massive parallel sequencing", "high-throughput sequencing", "next generation sequencing" and their variants refer to sequencing technologies that parallelize the sequencing process, producing thousands or millions of sequences concurrently. Various methodologies and processes involved in the technology are described by Mardis E R (2008) "Next-generation DNA sequencing methods", Annu Rev Genomics Hum Genet 9: 387-402; and by M. L. Metzker (2010) "Sequencing technologies—the next generation", Nature Review Genetics 11:31-46.

Term "priming region", "priming section", and their derivatives refer to a section of a target sequence of interest that is designed to be substantially hybridized with a corresponding primer.

Term "probe sequence", "probe", and their derivatives refer to a nucleic acid sequence that is designed to be hybridized with a target sequence of interest for the purposes of detection, capture, and enrichment. In some embodiments, a probe contains one or more fluorescence dye groups. In some embodiments, the probe contains one or more fluorescence quencher groups. In some embodiments, the probe contains one or more fluorescence quencher groups. In some embodiments, the probe contains one or more donor and/or acceptor fluorophore groups. In some embodiments, the probe sequence is a free molecule in a solution. In some embodiments, the probe sequence is immobilized on a bead surface. In some embodiments, the probe sequence is immobilized on a substantially flat surface. In some embodiments, the probe sequence is embedded in gel.

Term "specificity" generally refers to the fraction of correctly reported events among all reported events. In some embodiments, the term refers to the fraction of the primers correctly extended on the intended targets among all primers under consideration that have extended in primer extension reactions. In some embodiments, the term refers to the fraction of correct PCR products among all PCR products produced in PCR reactions. In some embodiments, the term refers to the fraction of perfectly matched probe-target pairs among all probe-target pairs in hybridization reactions.

Term "variant", "sequence variation", and their derivatives refer to a sequence section of a sample of interest that is different from the sequence section at the same location in a reference sample or in a reference sequence. The variation includes point and structural variation. For the purpose of this disclosure, the variation can be either disease related or non-disease related. The point variation includes single-nucleotide polymorphism or SNP. The structural variation includes short insertion, short deletion, large insertion, large deletion, indel (a deletion followed by an insertion), substitution, duplications, inversion, translocations, or any other types of variations.

Term "captured region", "capture region", and their derivatives refer to the region of a target sequence sandwiched between two paired primers including the target specific sections of the primers.

SUMMARY

It is the object of the present invention to provide a new and improved PCR method that is simple to perform, has improved sequence specificity, has low primer related amplification bias, and is suitable for multiplex amplification uses.

One application aspect of the present invention relates to the field of target enrichment for massive parallel sequencing applications. Target sequences of interest are selected from genomic samples, amplified, and flanked with sequencing priming sections containing optional DNA barcodes. Another application aspect of the present invention relates to field of target enrichment for DNA array genotyping applications. Target sequences of interest are selected from genomic samples, amplified, and labeled with fluorescence dyes or with conjugation ligands. Technical approaches in the target enrichment methods of the two applications share many similarities. Extensive technology reviews of the field have been provided by E. H. Turner et al. (2009) "Methods for genomic partitioning", Annu. Rev. Genomics Hum. Genet. 10:263-284 and by Memanova et al. (2010) "Target-enrichment strategies for nextgeneration sequencing" Nat. Methods 7, 111-118. Prevailing methods include multiplex PCR, capture-by-circularization, and capture-by-hybridization. The performance of a method is mainly evaluated by capture specificity, uniformity, multiplexity, input requirements, scalability, workflow simplicity, and cost. The present invention provides methods and compositions for target enrichment with significantly improved performances.

The present invention relates to oligonucleotide primers having a 3p arm which includes a 3' end and a 5' end, a loop section and a 5p arm having a 3' end and a 5' end, where the 5p arm hybridizes to a DNA template and wherein the 3p arm hybridizes to the DNA template and provides sequence specificity for polymerase extension and where the loop section is located between the 5p arm and the 3p arm and does not bind the DNA template.

The present invention relates to stable hybridization structures comprising a designed oligonucleotide and a target nucleic acid, wherein the designed sequence and the target sequence form a stable, where the hybridization structure has one or more single stranded loops and two or more duplex segments wherein each loop is located between the duplex segments.

The present invention relates to methods of amplifying a target nucleic acid comprising providing a first specific primer, a second specific primer, a first common primer, a second common primer a target nucleic acid, a polymerase and nucleotides, performing a target selection comprising two cycles of a first thermocycling routine comprising an denaturation step, annealing step and an extension step and performing amplification comprising two or more cycles of a second thermocycling routine comprising an denaturation step, annealing step and an extension step thereby amplifying the target nucleic acid.

The present invention relates to methods of amplifying two or more different target nucleic acids comprising providing a first set of specific primers containing two specific primers each primer specifically designed for a first target nucleic acid, a second set of specific primers, each primer specifically designed for a second target nucleic acid, a first common primer, a second common primer and a target nucleic acid; performing two cycles of a first thermocycling routine comprising an denaturation step, annealing step and an extension step; and performing two or more cycles of a second thermocycling routine comprising an denaturation step, annealing step and an extension step thereby amplifying the target nucleic acid.

The present invention relates to methods of purifying PCR products comprising adding to a mixture of PCR reaction components comprises target sequences, a first common primer and a second common primer, DNA fragments, polymerase, PCR buffer solution wherein the target sequences are flanked with priming segments that are either identical or complementary to the first common primer and the second common primer and wherein the fragments do not contain priming segments and wherein the second common primer comprises a priming segment, a modifier segment and a tag segment probe grafted beads wherein the probe has a sequence that is substantially complementary to that of tag segment and facilitates the capture of the PCR product by the beads 721 through hybridization.

The present invention relates to methods of sequence library preparation comprising amplifying a target sequence with a first common primer and a second common primer each common primer comprising a priming segment, modifier segment and tag segment to produce PCR products containing a single-stranded tag applying a guide solution to the substrate thereby hybridizing the probes to the substrate to produce guide/probe pairs on the substrate surface, washing away excess guide solution and adding the single-strand tag containing PCR products to the substrate thereby co-hybridizing the single-strand tag, a guide, and the probe on the substrate surface.

DETAILED DESCRIPTION

Target Specific Primer

Figure 1:
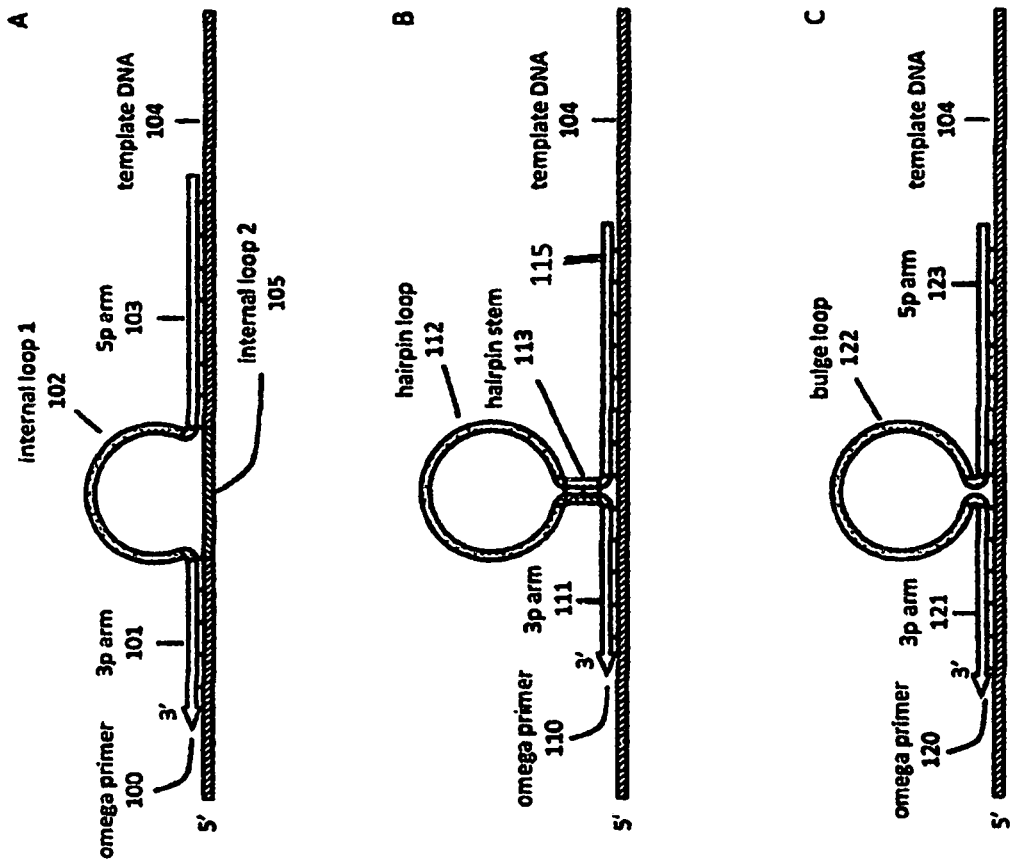
FIG. 1 shows schematic diagrams of three exemplary designs of the disclosed omega primer. A. omega primer with internal loops; B. omega primer with hairpin loop; and C. omega primer with bulge loop.

One aspect of the invention relates to a primer form, called omega primer. FIG. 1 shows schematic diagrams of three exemplary structural designs of the omega primer 100, 110, and 120. Each primer comprises three functional sections including a 3p arm 101, 111, and 121, a loop 102, 112, and 122, and a 5p arm 103, 115, and 123. One function of the 3p arm 101, 111, and 121 is to hybridize to a DNA template 104 and to provide a starting point for polymerase extension reaction. The 5p arm 103, 115 and 123 stabilizes the binding between the omega primer and the DNA template. The loop 102, 112, and 122 provides a separation between the two arms. FIG. 1A schematically illustrates an omega primer 100 with internal loops 102 and 105. The internal loops are single-stranded nucleic acid sequence sections on both primer 100 and template 104 strands between the double-stranded 3p arm 101 and 5p arm 103 sections. FIG. 1B schematically illustrates an omega primer 110 with a hairpin loop. The hairpin loop is formed by the primer sequence, comprising a single-stranded loop 112 and a double-stranded stem 113. FIG. 1C schematically illustrates an omega primer 120 with a bulge loop 122. This bulge loop structure is formed solely inside the primer. These structures are formed by hybridization interactions between primer and template sequences and can be designed with theoretical calculations by those of skilled in the art (see J. SantaLucia Jr. et al. (2004) "The thermodynamics of DNA structural motifs" Annu. Rev. Biophys. Biomol. Struct. 33:415-440).

The disclosed omega primers provide desirable features and/or properties in various applications. One aspect of the invention is the utilization of two separate binding sections to balance priming specificity and binding strength. In one exemplary application, the 5p arm is designed to have higher binding energy than 3p arm has so that 5p arm may initiate and sustain binding while 3p arm checks sequence specificity for polymerase extension. A successful priming reaction requires the hybridizations of the two separate sections. This reduces the chance for off-target priming and results in highly specific primer designs. The binding strength of the 5p arm compared to the binding strength of the 3p arm may be 1.1 times greater, or 1.2 times greater or 1.3 times greater or 1.4 times greater or 1.5 times greater of 1.6 times greater or 1.7 times greater, or 1.8 times greater or 1.9 times greater or 2 times greater or 2.5 times greater of 3 times greater or 5 times greater or 10 times greater. The binding strength of the 5p arm compared to the binding strength of the 3p arm may be between 1.1 to 100 times greater, 1.1 to 50 times greater, 1.1 to 25 times greater, 1.1 to 20 times greater, 1.1 to 15 times greater, 1.1 to 10 times greater, 1.1 to 5 times greater, 1.5 to 100 times greater, 1.5 to 50 times greater, 1.5 to 25 times greater, 1.5 to 20 times greater, 1.5 to 15 times greater, 1.5 to 10 times greater, 1.5 to 5 times greater, 2.0 to 100 times greater, 2.0 to 50 times greater, 2.0 to 25 times greater, 2.0 to 20 times greater, 2.0 to 15 times greater, 2.0 to 10 times greater, 2.0 to 5 times greater, 5.0 to 100 times greater, 5.0 to 50 times greater, 5.0 to 25 times greater, 5.0 to 20 times greater, 5.0 to 15 times greater, 5.0 to 10 times greater, 5.0 to 5 times greater.

Another aspect of this design is the ability to make the omega primers tolerant to certain template sequence variations at designated priming site. This feature is highly desirable in assays designed for covering general populations. For example, the 1000 Genomes Project reported a validated haplotype map of 38 million single nucleotide polymorphism (SNP) variants in human populations (The 1000 Genomes Project Consortium (2012) "An integrated map of genetic variation from 1,092 human genomes" Nature 491:56-65). This means one SNP variant in an average of less than 200 nucleotides in human genome of 6 billion diploid nucleotides long. The current version NCBI dbSNP for human contains 74 million SNP variants with genotype, meaning one SNP variant in average of every 40 nucleotides in human genome of 3 billion nucleotides long. SNP is the most abundant form of variant in human genome. These variants impose challenges to PCR primer design since a primer designed for a reference target sequence may not work well when it is applied to an actual target sample that happens to contain one or more variants in corresponding priming region. Due to the high density of the variants in general populations, it is desirable to have primers that are able to tolerate the variants so as to maximize the accessible regions for priming in the target sequence. One aspect of this disclosure is to include the variants into consideration in primer design. In designing omega primers the 5p arm length should be sufficiently long that the binding between the 5p arm and all anticipated variant target alleles is stable at the corresponding reaction temperature. The 3p arm length should be just long enough to achieve a stable binding with the reference target allele. Thus, the 5p arm serves as an anchor and the 3p arm checks for correctness of the priming site. This design strategy significantly expands the assessable regions for priming in the target sequence, results in variant tolerant primers, and yet produces high priming specificity. The 5p arm may be at least 10 nucleotides long, or at least 15 nucleotides long or at least 20 nucleotides long, or at least 25 nucleotides, or at least 30 nucleotides long, or at least 35 nucleotides long or at least 40 nucleotides long, or at least 45 nucleotides long, or at least 50 nucleotides long, or at least 55 nucleotides long or at least 60 nucleotides long, or at least 65 nucleotides or at least 70 nucleotides long, or at least 75 nucleotides long or at least 80 nucleotides long, or at least 85 nucleotides, or at least 90 nucleotides long, or at least 95 nucleotides long or at least 100 nucleotides long, or at least 125 nucleotides long, or at least 150 nucleotides long, or at least 200 nucleotides long or at least 250 nucleotides long. The 5p arm may be between 10 to 200 nucleotides in length, or be between 10 to 150 nucleotides in length, or be between 10 to 100 nucleotides in length, or be between 10 to 90 nucleotides in length, or between 10 to 80 nucleotides in length, or be between 10 to 70 nucleotides in length, or be between 10 to 60 nucleotides in length, or be between 10 to 50 nucleotides in length, or between 10 to 40 nucleotides in length, or be between 10 to 30 nucleotides in length, or be between 10 to 20 nucleotides in length, or be between 15 to 200 nucleotides in length, or be between 15 to 150 nucleotides in length, or be between 15 to 100 nucleotides in length, or be between 15 to 90 nucleotides in length, or between 15 to 80 nucleotides in length, or be between 15 to 70 nucleotides in length, or be between 15 to 60 nucleotides in length, or be between 15 to 50 nucleotides in length, or between 15 to 40 nucleotides in length, or be between 15 to 30 nucleotides in length, or be between 15 to 20 nucleotides in length, or between 20 to 200 nucleotides in length, or be between 20 to 150 nucleotides in length, or be between 20 to 100 nucleotides in length, or be between 20 to 90 nucleotides in length, or between 20 to 80 nucleotides in length, or be between 20 to 70 nucleotides in length, or be between 20 to 60 nucleotides in length, or be between 20 to 50 nucleotides in length, or between 20 to 40 nucleotides in length, or be between 20 to 30 nucleotides in length, or between 25 to 200 nucleotides in length, or be between 25 to 150 nucleotides in length, or be between 25 to 100 nucleotides in length, or be between 25 to 90 nucleotides in length, or between 25 to 80 nucleotides in length, or be between 25 to 70 nucleotides in length, or be between 25 to 60 nucleotides in length, or be between 25 to 50 nucleotides in length, or between 25 to 40 nucleotides in length, or be between 25 to 30 nucleotides in length, or between 30 to 200 nucleotides in length, or be between 30 to 150 nucleotides in length, or be between 30 to 100 nucleotides in length, or be between 30 to 90 nucleotides in length, or between 30 to 80 nucleotides in length, or be between 30 to 70 nucleotides in length, or be between 30 to 60 nucleotides in length, or be between 30 to 50 nucleotides in length, or between 30 to 40 nucleotides in length, or be between 35 to 200 nucleotides in length, or be between 35 to 150 nucleotides in length, or be between 35 to 100 nucleotides in length, or be between 35 to 90 nucleotides in length, or between 35 to 80 nucleotides in length, or be between 35 to 70 nucleotides in length, or be between 35 to 60 nucleotides in length, or be between 35 to 50 nucleotides in length, or between 35 to 40 nucleotides in length, or be between 40 to 200 nucleotides in length, or be between 40 to 150 nucleotides in length, or be between 40 to 100 nucleotides in length, or be between 40 to 90 nucleotides in length, or be between 40 to 80 nucleotides in length, or be between 40 to 70 nucleotides in length, or be between 40 to 60 nucleotides in length, or be between 40 to 50 nucleotides in length.

The 3p arm may be at least 5 nucleotides long, or at least 6 nucleotides long or at least 7 nucleotides long, or at least 8 nucleotides, or at least 9 nucleotides long, or at least 10, or at least 11 nucleotides long or at least 12 nucleotides long, or at least 13 nucleotides long, or at least 14 nucleotides long, or at least 15 nucleotides long or at least 20 nucleotides long, or at least 25 nucleotides or at least 30 nucleotides long, or at least 35 nucleotides long or at least 40 nucleotides long, or at least 45 nucleotides, or at least 50 nucleotides long, or at least 55 nucleotides long or at least 60 nucleotides long, or at least 65 nucleotides long, or at least 70 nucleotides long, or at least 80 nucleotides long or at least 90 nucleotides long. The 3p arm may be between 5 to 100 nucleotides in length, or be between 5 to 90 nucleotides in length, or between 5 to 80 nucleotides in length, or be between 5 to 70 nucleotides in length, or be between 5 to 60 nucleotides in length, or be between 5 to 55 nucleotides in length, or between 5 to 50 nucleotides in length, or be between 5 to 45 nucleotides in length, or be between 5 to 40 nucleotides in length, or be between 5 to 35 nucleotides in length, or be between 5 to 30 nucleotides in length, or be between 5 to 25 nucleotides in length, or be between 5 to 20 nucleotides in length, or between 5 to 15 nucleotides in length, or be between 5 to 10 nucleotides in length, or be between 6 to 100 nucleotides in length, or be between 6 to 90 nucleotides in length, or between 6 to 80 nucleotides in length, or be between 6 to 70 nucleotides in length, or be between 6 to 60 nucleotides in length, or be between 6 to 55 nucleotides in length, or between 6 to 50 nucleotides in length, or be between 6 to 45 nucleotides in length, or be between 6 to 40 nucleotides in length, or be between 6 to 35 nucleotides in length, or be between 6 to 30 nucleotides in length, or be between 6 to 25 nucleotides in length, or be between 6 to 20 nucleotides in length, or between 6 to 15 nucleotides in length, or be between 6 to 10 nucleotides in length, or between 7 to 100 nucleotides in length, or be between 7 to 90 nucleotides in length, or between 7 to 80 nucleotides in length, or be between 7 to 70 nucleotides in length, or be between 7 to 60 nucleotides in length, or be between 7 to 55 nucleotides in length, or between 7 to 50 nucleotides in length, or be between 7 to 45 nucleotides in length, or be between 7 to 40 nucleotides in length, or be between 7 to 35 nucleotides in length, or be between 7 to 30 nucleotides in length, or be between 7 to 25 nucleotides in length, or be between 7 to 20 nucleotides in length, or between 7 to 15 nucleotides in length, or be between 7 to 10 nucleotides in length, be between 10 to 100 nucleotides in length, or be between 10 to 90 nucleotides in length, or between 10 to 80 nucleotides in length, or be between 10 to 70 nucleotides in length, or be between 10 to 60 nucleotides in length, or be between 10 to 55 nucleotides in length, or between 10 to 50 nucleotides in length, or be between 10 to 45 nucleotides in length, or be between 10 to 40 nucleotides in length, or be between 10 to 35 nucleotides in length, or be between 10 to 30 nucleotides in length, or be between 10 to 25 nucleotides in length, or be between 10 to 20 nucleotides in length, or between 10 to 15 nucleotides in length, or between be between 15 to 100 nucleotides in length, or be between 15 to 90 nucleotides in length, or between 15 to 80 nucleotides in length, or be between 15 to 70 nucleotides in length, or be between 15 to 60 nucleotides in length, or be between 15 to 55 nucleotides in length, or between 15 to 50 nucleotides in length, or be between 15 to 45 nucleotides in length, or be between 15 to 40 nucleotides in length, or be between 15 to 35 nucleotides in length, or be between 15 to 30 nucleotides in length, or be between 15 to 25 nucleotides in length, or be between 15 to 20 nucleotides in length.

There can be various embodiments of the disclosed omega primer designs. For example, a primer can consist of three or more binding sections that are separated by two or more loops. It is desirable to distribute the binding feature of a primer into two or more segmented binding sections separated by loop sections for the purpose of improving priming specificity, modulating binding strength, inserting or incorporating specific sequences, and/or obtaining other desirable functions. The loop may be at least 5 nucleotides long, or at least 6 nucleotides long or at least 7 nucleotides long, or at least 8 nucleotides, or at least 9 nucleotides long, or at least 10, or at least 11 nucleotides long or at least 12 nucleotides long, or at least 13 nucleotides long, or at least 14 nucleotides long, or at least 15 nucleotides long or at least 20 nucleotides long, or at least 25 nucleotides or at least 30 nucleotides long, or at least 35 nucleotides long or at least 40 nucleotides long, or at least 45 nucleotides, or at least 50 nucleotides long, or at least 55 nucleotides long or at least 60 nucleotides long, or at least 65 nucleotides long, or at least 70 nucleotides long. The loop may be between 7 to 100 nucleotides in length, or be between 7 to 90 nucleotides in length, or between 7 to 80 nucleotides in length, or be between 7 to 70 nucleotides in length, or be between 7 to 60 nucleotides in length, or be between 7 to 55 nucleotides in length, or between 7 to 50 nucleotides in length, or be between 7 to 45 nucleotides in length, or be between 7 to 40 nucleotides in length, or be between 7 to 35 nucleotides in length, or be between 7 to 30 nucleotides in length, or be between 7 to 25 nucleotides in length, or be between 7 to 20 nucleotides in length, or between 7 to 15 nucleotides in length, or be between 7 to 10 nucleotides in length, be between 10 to 100 nucleotides in length, or be between 10 to 90 nucleotides in length, or between 10 to 80 nucleotides in length, or be between 10 to 70 nucleotides in length, or be between 10 to 60 nucleotides in length, or be between 10 to 55 nucleotides in length, or be between 10 to 50 nucleotides in length, or be between 10 to 45 nucleotides in length, or be between 10 to 40 nucleotides in length, or be between 10 to 35 nucleotides in length, or be between 10 to 30 nucleotides in length, or be between 10 to 25 nucleotides in length, or be between 10 to 20 nucleotides in length, or between 10 to 15 nucleotides in length, or between 12 to 100 nucleotides in length, or be between 12 to 90 nucleotides in length, or between 12 to 80 nucleotides in length, or be between 12 to 70 nucleotides in length, or be between 12 to 60 nucleotides in length, or be between 12 to 55 nucleotides in length, or between 12 to 50 nucleotides in length, or be between 12 to 45 nucleotides in length, or be between 12 to 40 nucleotides in length, or be between 12 to 35 nucleotides in length, or be between 12 to 30 nucleotides in length, or be between 12 to 25 nucleotides in length, or be between 12 to 20 nucleotides in length, or between 12 to 15 nucleotides in length or between be between 15 to 100 nucleotides in length, or be between 15 to 90 nucleotides in length, or between 15 to 80 nucleotides in length, or be between 15 to 70 nucleotides in length, or be between 15 to 60 nucleotides in length, or be between 15 to 55 nucleotides in length, or between 15 to 50 nucleotides in length, or be between 15 to 45 nucleotides in length, or be between 15 to 40 nucleotides in length, or be between 15 to 35 nucleotides in length, or be between 15 to 30 nucleotides in length, or be between 15 to 25 nucleotides in length, or be between 15 to 20 nucleotides in length.

Figure 2:
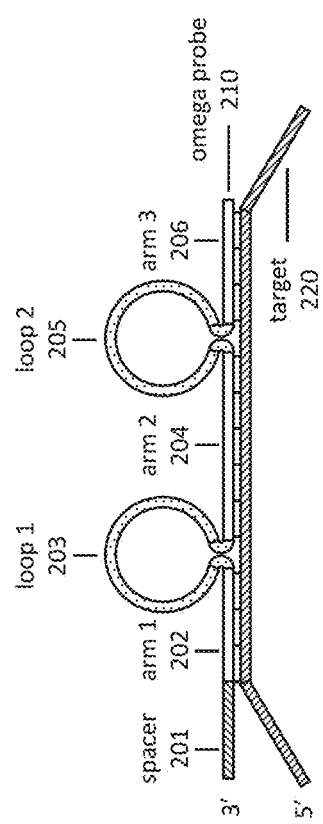
FIG. 2 shows schematic diagrams of an exemplary design of the disclosed omega probe.

An exemplary embodiment of this invention is a high specificity hybridization probe. The probe (omega probe) sequence is designed to form one or more omega loops flanked by omega arms when hybridized with a target sequence. FIG. 2 shows an exemplary omega probe 210, which comprises of a spacer 201, omega arms 1 through 3 202, 204 and 206, and omega loop 1 203 and loop 2 205. The spacer 201 is optional depending on specific applications and can be attached to either 3' or 5' end of the probe. For applications requiring the attachment of the probe to a surface, it is often preferred to have the attachment through the spacer. In some embodiments, the spacer 201 comprises one or more nucleotides. In some embodiments, the spacer 201 comprises one or more non-nucleotide moieties. In some embodiments, the non-nucleotide moieties include but not limited to at least one C3 alkyl spacer, at least one ethylene glycol spacer, and at least one 1',2'-dideoxyribose. In some embodiments, omega arm 202, 204, or 206 comprises at least one nucleotide. In some embodiments, the number of nucleotides is between 1 and 100. In some embodiments, the number of nucleotides is between 3 and 60. In some embodiments, the number of nucleotides is between 5 and 40. In some embodiments, each loop 203 or 205 comprises one or more nucleotides. In some embodiments, the number of nucleotides is between 1 and 100. In some embodiments, the number of nucleotides is between 3 and 60. In some embodiments, the number of nucleotides is between 5 and 40. In some embodiments, each loop 203 or 205 comprises one or more non-nucleotide moieties. In some embodiments, the non-nucleotide moieties include but not limited to at least one C3 alkyl spacer, at least one ethylene glycol spacer, and at least one 1',2'-dideoxyribose. In some embodiments, the length of each non-nucleotide loop 203 or 205 is between 1 and 200 molecular bonds. In some embodiments, the length of each loop 203 or 205 is between 5 and 100 molecular bonds. In some embodiments, the length of each loop 203 or 205 is between 5 and 60 molecular bonds.

Thermodynamically, in a binding reaction between the probe 210 and the corresponding target template sequence 220, the omega arms 202, 204, and 206 bind to the template 220, reduce free energy, and stabilize the binding while the omega loops 203 and 205 are strained, increase free energy, and destabilize the binding. In an exemplary embodiment, the lengths of the arms and loops are designed in such a way that the free energy decrease due to the arms and the increase due to the loops are carefully balanced to produce stable omega shaped structures at a predetermined hybridization condition when the probe is hybridized with the intended target. When the target contains one or more variant nucleotides the probe-target binding of the original structure is no longer stable and results in reduced binding. A significant advantage of the disclosed omega probe design over a regular hybridization probe design that contains one continuous target-complementary binding segment is the ability to extend probe length without sacrificing specificity. In general, a nucleic acid binding assay reports the number of targets hybridized to corresponding probes. The number is usually measured through binding densities either on a probe containing surface or in a probe containing solution. An equilibrium binding density is determined by binding free energy. The lower the free energy the higher the equilibrium binding density will be (Miura el al. (2005) "A novel strategy to design highly specific PCR primers based on the stability and uniqueness of 3'-end subsequences" Bioinformatics 21 4363-4370). The binding free energy of a regular probe increases with the increase of probe length. When the regular probe is long (e.g. longer than 35 nucleotides), a short variant such as a SNP in the target would only produce a small fraction of free energy increase in the probe-target binding. Therefore, sequence specificity of a regular probe decreases with increase of probe length. By comparison, free energy of the omega probe-target binding is modulated by omega loops and can be maintained by design at a certain desired level even when the overall binding length is long. Therefore, an omega probe retains high specificity over a wider range of probe-target binding length. The free energy of the entire omega structure should kept below zero at the hybridization condition. The free energy calculations for the omega primer are described in section "Computation methods" of this specification. One exemplary embodiment of the omega probe is microarray assay which may involves one or more detection methods including but not limited to labeling target sequence with a fluorescence dyes for regular fluorescence detection and labeling omega probes on or near loop nucleotides with donor and acceptor fluorophore groups for FRET (fluorescence resonance energy transfer)

detection. These and additional labeling and detection methods are described by Buzdin in A. Buzdin and S. Lukyanov (2007) "Stem-loop oligonucleotides as hybridization probes and their practical use in molecular biology and biomedicine" Nucleic Acids Hybridization, Chapter 14, 85-96, Springer.

Relay PCR

Figure 3:
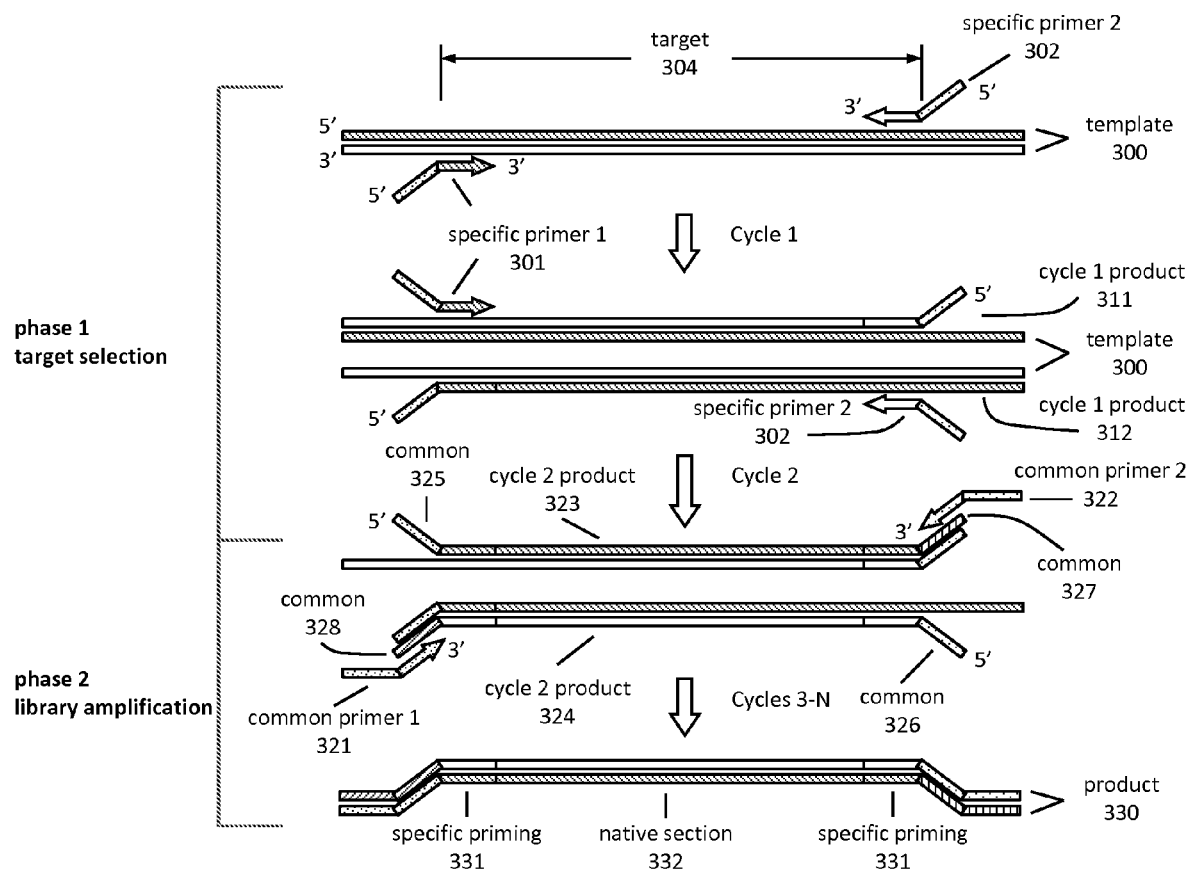
FIG. 3 schematically outlines an exemplary embodiment of relay PCR method using regular specific primers.
Figure 3:

One aspect of the invention relates to a method of target amplification which is named Relay PCR. A complete PCR run consists of two functionally distinct but sequentially connected reaction phases, namely target selection and library amplification, which are shown in FIG. 3 as phase 1 and phase 2 reactions. A significant advantage of the methods of the present invention is that the two functionally distinct reaction phases are carried out in a single tube, in a programmed process on a PCR machine, and without any hands-on operation during the process. A reaction mixture for the relay PCR includes two sets of primers, templates, plus appropriate polymerase, nucleotides and PCR buffer. The first set of primers includes at least one pair of specific primers 301 and 302. Generally, each pair of primers delineates a target region 304 of interest. An exemplary specific primer pair consists of specific primer 1 301 and specific primer 2 302. An exemplary specific primer 340 (a "regular" primer) consists of a specific segment 341 at 3' end (between 10 and 80 nucleotides, preferably 12 to 50, in length) and a common segment 342 at 5' end (between 10 and 80 nucleotides, preferably 12 to 50, in length). The sequence of the specific segment of each specific primer is substantially identical or complementary to corresponding portion of the corresponding target sequence or template. The second set of primers includes at least one pair of common primers. In an exemplary embodiment, one pair of common primers, comprising common primer 1 321 and common primer 2 322, are used. An exemplary common primer 350 has a common segment 351 at 3' end and a tail segment at 5' end 352. The sequences of the common segments of specific primer 1 301 and common primer 1 321 are substantially the same. The sequences of the common segments of specific primer 2 302 and common primer 2 322 are substantially the same. In preferred embodiments, the sequences of the common segments do not hybridize substantially with any portion of sample DNA sequences. In preferred embodiments, the concentration of a common primer is substantially higher than the concentration of corresponding specific primers. In some embodiments, the molar concentration ratio of a common primer to a corresponding specific primer is at least 50, 100, 500, 1,000, 5,000, 10,000, 50,000, or greater. Sequence designs of individual primers, suitable concentrations of the primers, common primer to specific primer concentration ratios, and polymerase selections will become clear as reaction conditions and application requirements are described.

FIG. 3 schematically outlines an exemplary embodiment of the relay PCR. In the figure, phase 1 is the target selection phase that consists of two thermo cycles and involves a pair of specific primers: specific primer 1 301 and specific primer 2 302. In cycle 1, specific primer 1 301 and specific primer 2 302 are extended on corresponding templates 300 producing two replicated cycle-one product sequences 311 and 312 of complementary strands. Herein, templates are nucleic acid sequences on which polymerase extension reactions take place and complementary replicates are produced. Throughout this specification, terms "template", "target sequence", and "sample DNA" are used interchangeably depending on the context of descriptions. By the extension reaction, the common segments of the specific primers are incorporated into the cycle-one product sequences. In cycle 2, specific primer 1 301 and specific primer 2 302 are extended on corresponding cycle-one product sequences 311 and 312 producing two replicated cycle-two product sequences 323 and 324 of complementary strands. Cycle-two product sequences 323 and 324 are flanked with common segments 325 and 326 of specific primers 1 and 2 at 5' ends and with complementary common segments 327 and 328 of the specific primers at 3' ends. The cycle-two product sequences are the both-end flanked target sequences that are amplified in the remaining thermo cycles. Generally, common primers are designed not to hybridize substantially with any portion of sample DNA sequences and not to involve in cycle 1 and cycle 2 reactions. In FIG. 3, cycle 3 through cycle N constitute phase 2, in which a library of target sequences is amplified. Starting from cycle 3, the both-end flanked target sequences 323 and 324 become available and they carry complementary common segments 327 and 328 with which the common primers 321 and 322 hybridize and carry out amplification reactions. When plurality pairs of specific primers and one pair of common primers are involved, all corresponding target sequences are flanked with the same pair of common segments at the end of cycle 2 and are amplified with one pair of common primers between cycle 3 to cycle N (the last cycle). The high concentration ratio of common primer to specific primer ensures the dominance of the common primers in phase 2 amplification reactions.

One aspect of the disclosed relay PCR method is the elimination of the need to perform multiple hands-on PCR rounds and product purifications that were used previously to switch from target specific primer amplifications to common primer amplifications (e.g. Z. Lin et al. (1996), in "Multiplex genotype determination at a large number of gene loci" Proc. Natl. Acad. Sci. 93: 2582-2587; K. E. Varley et al. (2008) "Nested Patch PCR enables highly multiplexed mutation discovery in candidate Genes" Genome Res. 18:1844-1850; and J. Leamon et al. (2012) "Methods and compositions for multiplex PCR" US Patent Application Publication US 2012/0295819 A1).

Another aspect of the disclosed relay PCR method is the exclusion of target specific primers from participating in amplification process (cycle 3 to cycle N of FIG. 3) and so as to minimize specific primer related amplification bias. A characteristic of the disclosed relay PCR reaction is to limit the function of specific primers to producing flanked target sequences directly from original sample templates in phase 1 and to minimize the contribution of the specific primers to the target sequence amplification reactions in phase 2. This minimizes the primer-dependent amplification yield variations when two or more pairs of specific primers are involved.

Reaction conditions and primer designs have significant impact to the outcomes of the disclosed relay PCR reactions. For multiplex PCR applications, a distinct reaction condition of the present invention is the significantly lower specific target primer concentrations than that used in regular PCR reactions and in known variations of multiplex PCR reactions. Relay PCR reactions may be performed at much lower specific primer concentrations than previously used. In regular PCR reactions the primer concentration is between 100 nM and 5,000 nM (see Dieffenbach et al., PCR Primer: A Laboratory Manual, Cold Spring Harbor Laboratory Press, 2003). In known variations of multiplex PCR reactions, target specific primer concentration is between 10 nM and 400 nM (see Henegariu et al. (1997) "Multiplex PCR: Critical Parameters and Step-by-Step Protocol" BioTechniques 23: 504-511; J. Brownie et al. (1997), in "the elimination of primer-dimer accumulation in PCR" Nucleic Acids Res. 25: 3235-3241; K. E. Varley et al. (2008) "Nested Patch PCR enables highly multiplexed mutation discovery in candidate Genes" Genome Res. 18:1844-1850; and B. Frey et al. (2013) "Methods and amplification of target nucleic acids using a multi-primer approach" US Patent Application Publication US 2013/00045894 A1). By comparison, in an exemplary embodiment of the present invention, as shown in Examples I to III, the concentration of each individual specific primer is 1 nM or lower and the concentration of each common primer is 500 nM. Another distinct reaction condition of the present invention is the use of significantly extended annealing times in thermo cycles 1 and 2 in combination with the low specific primer concentrations. In regular PCR and known variations of multiplex PCR reactions, annealing time is between 10 sec and 2 min. By comparison, in an exemplary embodiment of the present invention, as shown in Examples I through IV, extension times between 30 min and 4 hours are used in thermo cycles 1 and 2. Using the previously reported annealing time of 30 sec (e.g. B. Frey et al. (2013) "Methods and amplification of target nucleic acids using a multi-primer approach" US Patent Application Publication US 2013/00045894 A1) at specific primer concentration of 1 nM or lower the amount PCR product obtained was low and was below the detection limit of regular agarose gel electrophoresis measurement in experiments. Another distinct reaction condition of the present invention is the use of high annealing temperatures in cycles 1 and 2, in combination with the long extension times. These exemplary reaction conditions merely represent certain aspects of the present invention and are not intended, nor should be construed, as limiting the invention in any manner. The exact reaction conditions for specific applications can be determined by those who are skilled in the art by following the teachings of this specification in whole including references.

Figure 4A:
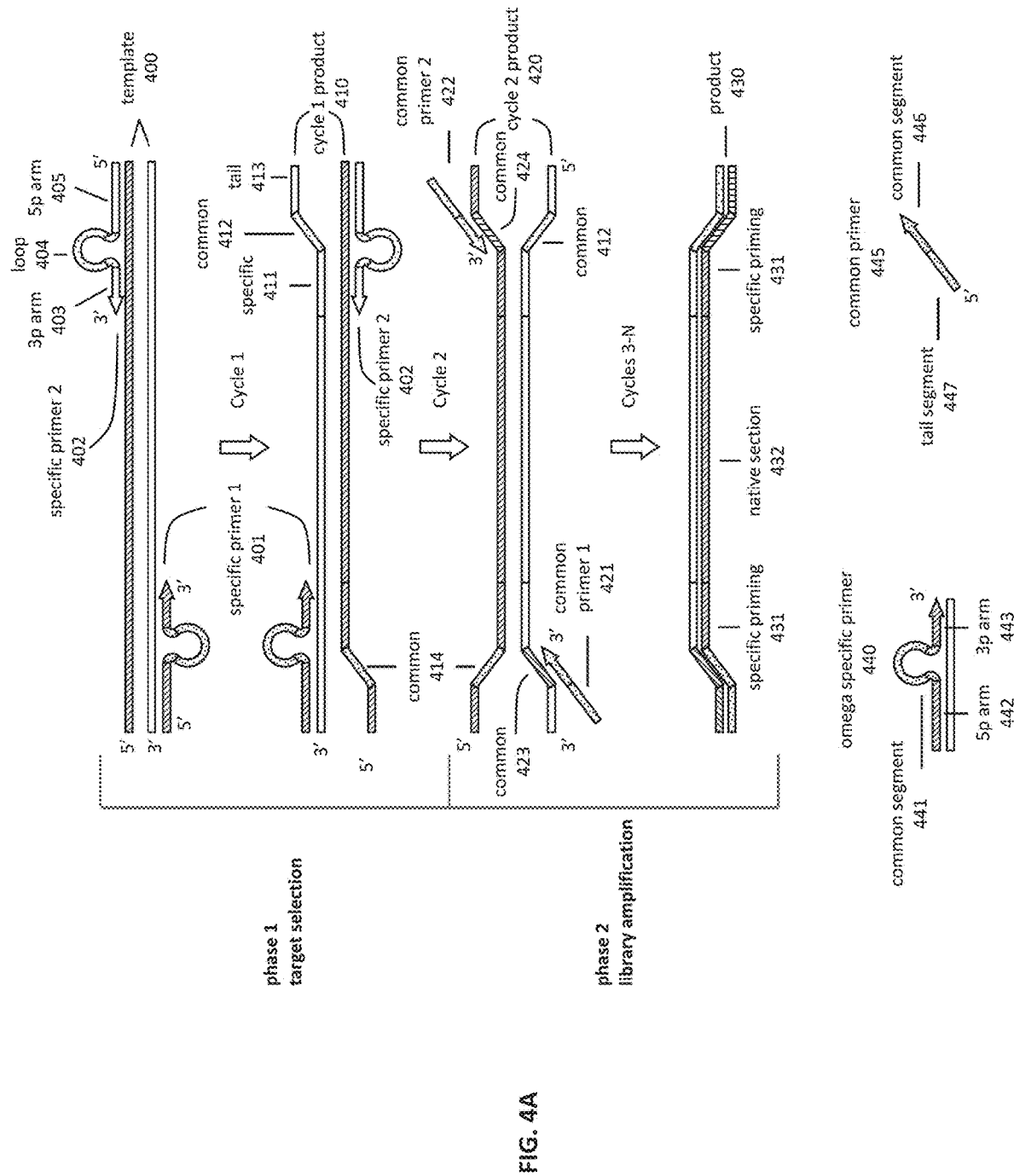
FIG. 4A schematically outlines an exemplary embodiment of relay PCR method using internal loop omega specific primers.

One aspect of the present invention is the use of omega primers advantageously as specific primers in relay PCR. FIG. 4A schematically outlines exemplary embodiments of a relay PCR using omega primers 401 and 402 as specific primers. In each primer, 3p arm 403 and 5p arm 405 are both target sequence specific. In other words, the arm sequences are complementary to the priming sections of corresponding template sequences 400. Loop sections 404 and 441 of the omega primers serve as common segments of the specific primers. Common primers 421, 422, and 445 consist of common segments 446 at 3' end and tail segments 447 at 5' end. The sequences of the common segments 441 and 446 of corresponding common primers 445 and omega primers 440 are substantially the same.

As shown in FIG. 4A, a complete relay PCR process comprises two phases, phase 1 for target selection and phase 2 for amplification. The target selection phase consists of two thermo cycles and involves a pair of specific primers: specific primer 1 401 and specific primer 2 402. In cycle 1, specific primer 1 401 and specific primer 2 402 are extended on corresponding templates 400 producing two replicated cycle-one product sequences 410 of complementary strands. The original specific primer 402 comprises the 5' section of the cycle-one products 410. The original 3p arm 403, loop 404, and 3p arm 405 of specific primer 402 become specific priming segment 411, common priming segment 412, and 5p arm tail segment 413 of the cycle-one product 410. In cycle 2, specific primer 1 401 and specific primer 2 402 are extended on corresponding cycle-one product sequences 410 producing two replicated cycle-two product sequences 420 of complementary strands. Cycle-two product sequences 420 are flanked with common segments 412 and 414 in sections close to 5' ends and with complementary common segments 423 and 424 in sections close to 3' ends. The complementary common segments 423 and 424 are complementary to common primers 421 and 422 and serve as priming sites for PCR amplification reaction from cycle 3 to cycle N. In some embodiments involving plurality pairs of specific primers, all primer pairs share the same pair of loop sequences so that a library of target sequences are amplified by one pair of common primers. The 5p arm tails 413 of cycle-one and cycle-two products are bypassed for library amplification by the common primers 422 and 423. As result, the final amplification products 430 retain only 3p arm portions of the original omega specific primers.

Figure 4B:
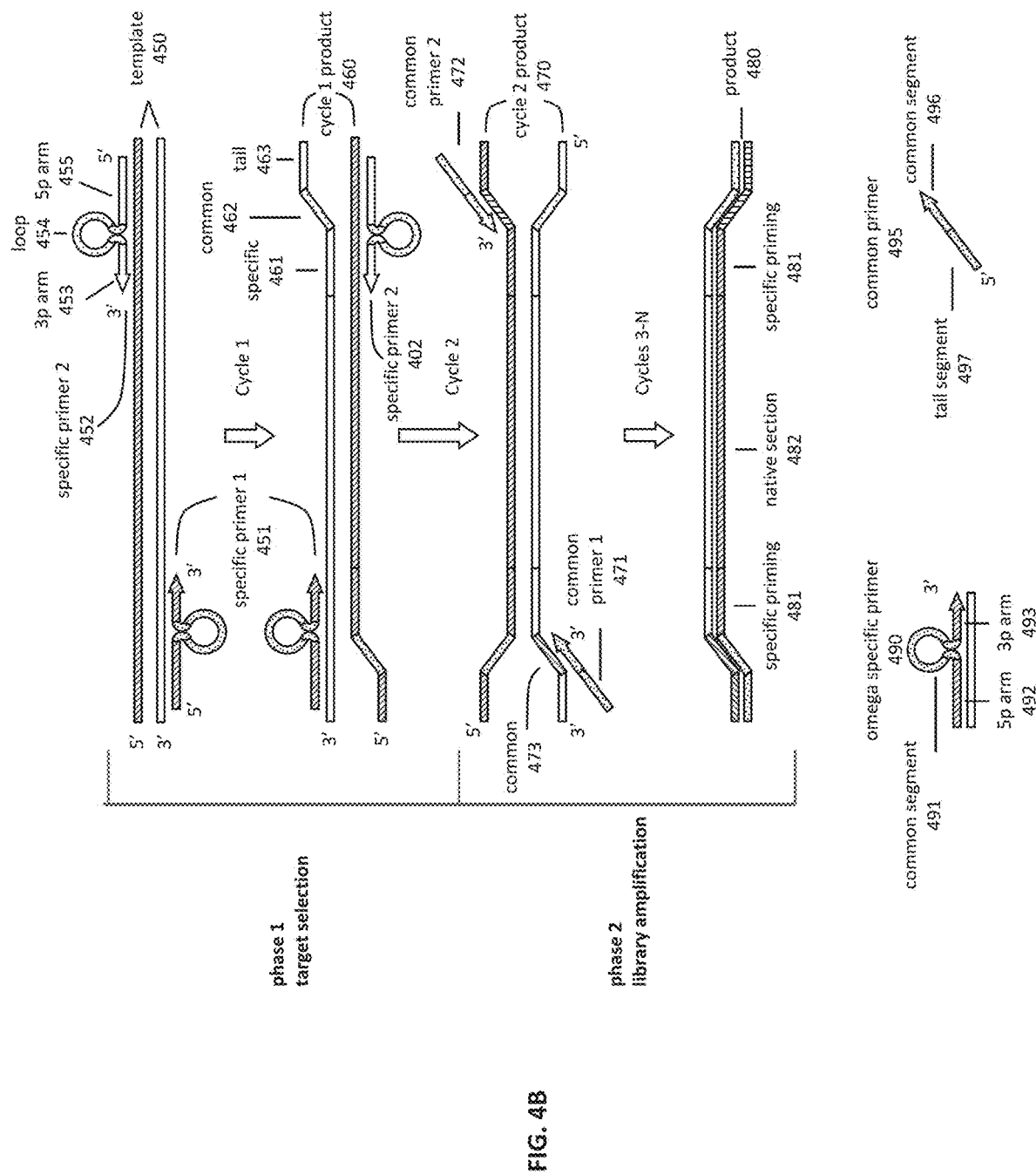
FIG. 4B schematically outlines an exemplary embodiment of relay PCR method using bulge loop omega specific primers.

While omega primers in FIG. 4A have internal loops, omega primers of other loop forms can be used in relay PCR as well. As another exemplary embodiment, FIG. 4B depicts a relay PCR process using omega primers of bulge loops as specific primers 451 and 452. The target selection and library amplification principles of the processes shown in FIG. 4A and FIG. 4B are substantially the same.

An exemplary application of combining omega primers with relay PCR is target enrichment for sequencing assay. The combination brings significant and unique benefits to the application. The fact that only the 3p arm portions 403 and 453 of the original omega specific primers are retained in the amplification products is highly desirable since it provides an opportunity to minimize the lengths of specific primer sections 431 and 481 in the amplified target sequences 430 and 480. This is achieved by using long 5p arms and short 3p arms while maintaining sufficiently stable bindings between the omega primers and corresponding templates at corresponding annealing temperature. For sequencing use, sequencing reads from the native sections 432 and 482 between specific priming sections 431 or 481 are from the native sequences of testing samples while sequencing reads from the specific primer sections 431 and 481 are dictated by the primers used. Since the reading length of a sequencing run is limited, it is highly desirable to shorten the specific primer sections 431 and 481 so as to maximize the useful reading length of the native sequences. In some embodiment, the tail segment 352, 447 and 497 of common primer 1 further comprises at least one barcode section. In some embodiment, the tail segment 352, 447 and 497 of common primer 2 further comprises at least one barcode section. In some embodiment, the tail segments 352, 447 and 497 of both common primer 1 and common primer 2 further comprise at least one barcode section. The design and the use of the barcodes are described in Bystrykh L V (2012) Generalized DNA Barcode Design Based on Hamming Codes. PLoS ONE 7(5): e36852. doi:10.1371/journal.pone.0036852.

In some embodiment, at least one omega primer contains two or more loops. In one exemplary embodiment shown in FIG. 5, a specific primer 501 comprises of a relay priming loop 502 and an insertion loop 503. The relay priming loop 502 serves as common segment of the specific primer. In cycle 1 reaction specific primer 1 501 extends and form cycle 1 product 511. This results in the incorporation of the insertion loop 503 into product as an insert 513. The remaining cycles proceed in a similar fashion as described above relating to the relay PCR processes of FIG. 4A and FIG. 4B. At the completion of the process, an insert 533 is incorporated into the final product 530. Exemplary applications of such segmented primers include but not limited to mutagenesis, gene knock out, gene knock in, signature tag, protein engineering, and gene therapy.

Figure 6:
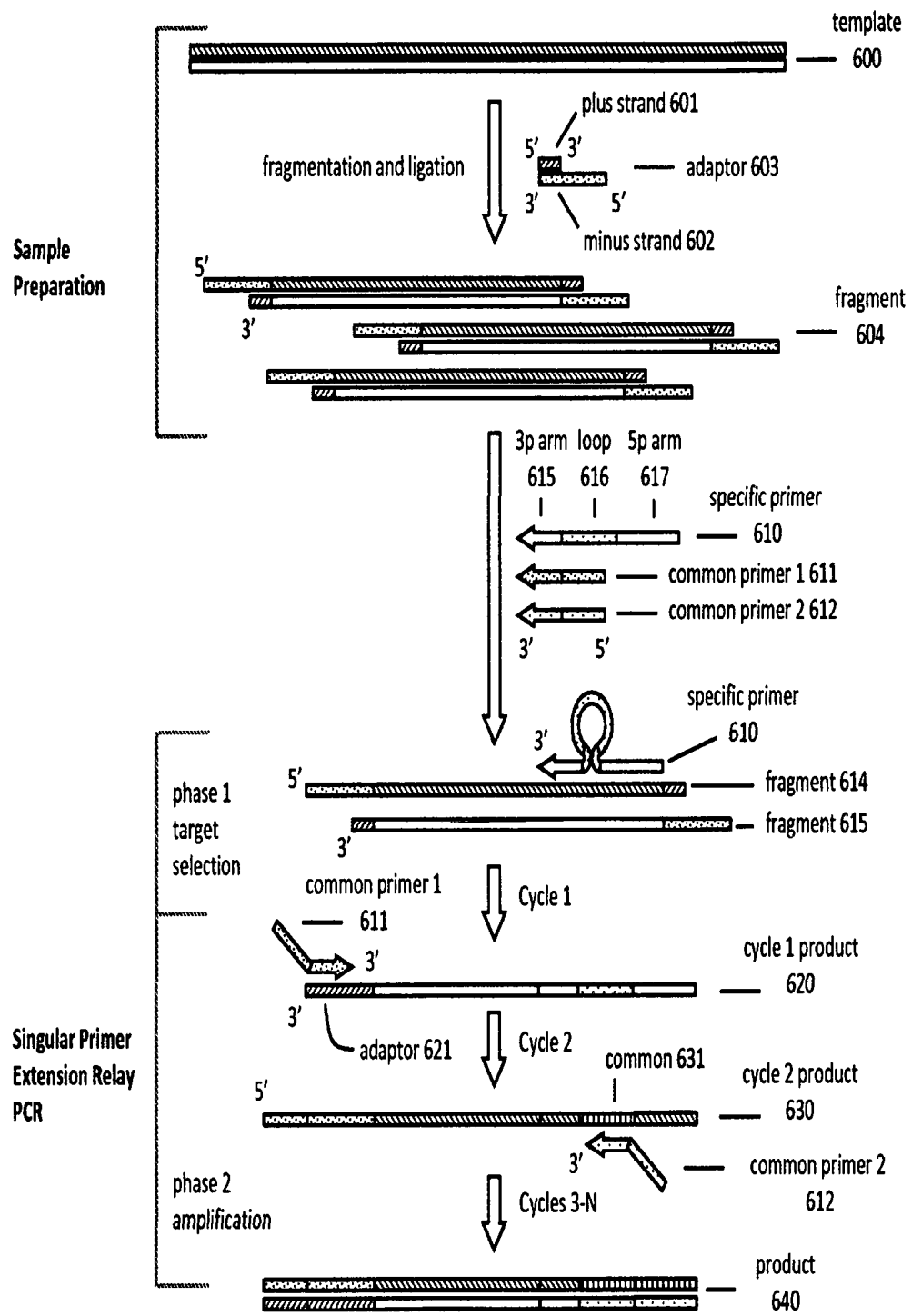
FIG. 6 schematically outlines an exemplary embodiment of singular primer extension relay PCR method using singular omega specific primers in target selection.

Some embodiments of target enrichment using relay PCR comprise target selection using singular primer extension and amplification using common primer PCR: singular primer extension relay PCR. FIG. 6 depicts an exemplary application embodiment, which comprises sample preparation and the relay PCR processes. The sample preparation involves fragmentation and adapter ligation. The process is well known to the field of molecular biology and is described in detail by N. Arneson et al. (2008) "Whole-Genome Amplification by Adaptor-Ligation PCR of Randomly Sheared Genomic DNA (PRSG)" Cold Spring Harb Protoc; and by D. Bentley et al. (2008) "Accurate whole human genome sequencing using reversible terminator chemistry" Nature 456 53-59 and associate supporting documents. An exemplary sample preparation starts with random fragmentation of double stranded DNA template 600 into short segments. The double stranded DNA sequences can be produced from various sources including not limited to genomic DNA and RNA derived double stranded cDNA. Fragmentation of the double stranded DNA can be accomplished using one or more various well known processes including nebulization, sonication, and enzymatic digestion. Nebulization may be accomplished using a commercial product Nebulizers and product instructions from Life Technologies (Grand Island, N.Y.). Sonication may be accomplished using one of various commercial products, e.g. Focused-ultrasonicator from Covaris instrument (Woburn, Mass.). Enzymatic digestion may be accomplished using commercial kit NEBNext® dsDNA Fragmentase from NEB (Ipswich, Mass.). Repair the ends of the DNA fragments using NEBNext® Ultra™ End Repair/dA-Tailing Module from NEB (Ipswich, Mass.). Add adaptors 603 to the end polished fragments by ligation using T4 DNA ligase from NEB (Ipswich, Mass.). Adaptor flanked fragments 604 are obtained. Adaptor 603 is a double strand DNA sequence comprising a plus strand oligonucleotide 601 and a minus strand oligonucleotide 602. In some embodiments, plus strand oligonucleotide 601 and minus strand oligonucleotide 602 are completely complementary to each other. In some embodiments, plus strand oligonucleotide 601 and minus strand oligonucleotide 602 are partially complementary to each other. In some embodiments, plus strand oligonucleotide 601 is shorter than minus strand oligonucleotide 602 and is substantially complementary to 3' section of the minus strand oligonucleotide 602. In some embodiments, the 3' end of plus strand oligonucleotide 601 a modified nucleotide that blocks the oligonucleotide from polymerase extension reaction. The exemplary modified nucleotide includes but is not limited to dideoxycytidine, inverted dT, 3' amino modifier, and 3' biotin. In some embodiments, 5' end of the plus strand oligonucleotide 601 is phosphorylated. In some embodiments, 3' end of the minus strand oligonucleotide 602 is a dA overhang.

The lower portion of FIG. 6 depicts the singular primer extension relay PCR process in which each target sequence is selected by the extension reaction of a singular specific primer and then amplified by PCR of one pair of common primers. In the exemplary embodiment, the reaction mixture comprises adaptor flanked fragments 604 as sample templates, one or more omega primers as target specific primers 610, common primer 1 611, common primer 2 612, and polymerase, all mixed in a PCR buffer solution. Each omega primer comprises a 3p arm 615, at least one loop 616, and a 5p arm 617. The sequences of 3p arm 615 and 5p arm 617 are designed based on predetermined target sequences from the starting DNA template 600. The loop 616 contains a section having substantially the same sequence as 3' section of common primer 2 612. The sequences of 3' section of common primer 1 611 and a selected section of minus strand oligonucleotide 602 are substantially the same. In some embodiments, the selected section of minus strand oligonucleotide 602 covers a substantial portion of minus strand oligonucleotide 602. In some embodiments, the selected section of minus strand oligonucleotide 602 covers a substantial portion of minus strand oligonucleotide 602 minus the portion overlapping with plus strand oligonucleotide 601. In cycle-one reaction, specific primer 610 binds to the corresponding target sequence fragment 614 and then is extended to produce cycle-one product 620. In cycle-two, common primer 1 611 binds to the adaptor 621 section of the cycle-one product 620 and then extends to produce cycle-two product 630. The cycle-two product 630 contains a common priming section 631 that is complementary to loop 616 of specific primer 610 and binds with common primer 2 612 to facilitate PCR amplification in the remaining cycles. From cycle 3 to cycle N the specific primer 610 selected target sequences are amplified by the paired common primer 1 611 and common primer 2 612 resulting in product 640. While the exemplary embodiment of FIG. 6 depicts omega primers as the specific primers, alternative embodiments may use regular primers as the specific primers in the singular primer extension relay PCR. The use of regular primers in relay PCR has been described above relating to FIG. 3. A regular primer is one that is not an omega primer; a regular primer has a binding segment without loops and/or, in some embodiments, extraneous mismatches (i.e., it has a one-to-one correspondence with its target sequence).

Separation

Figure 7:
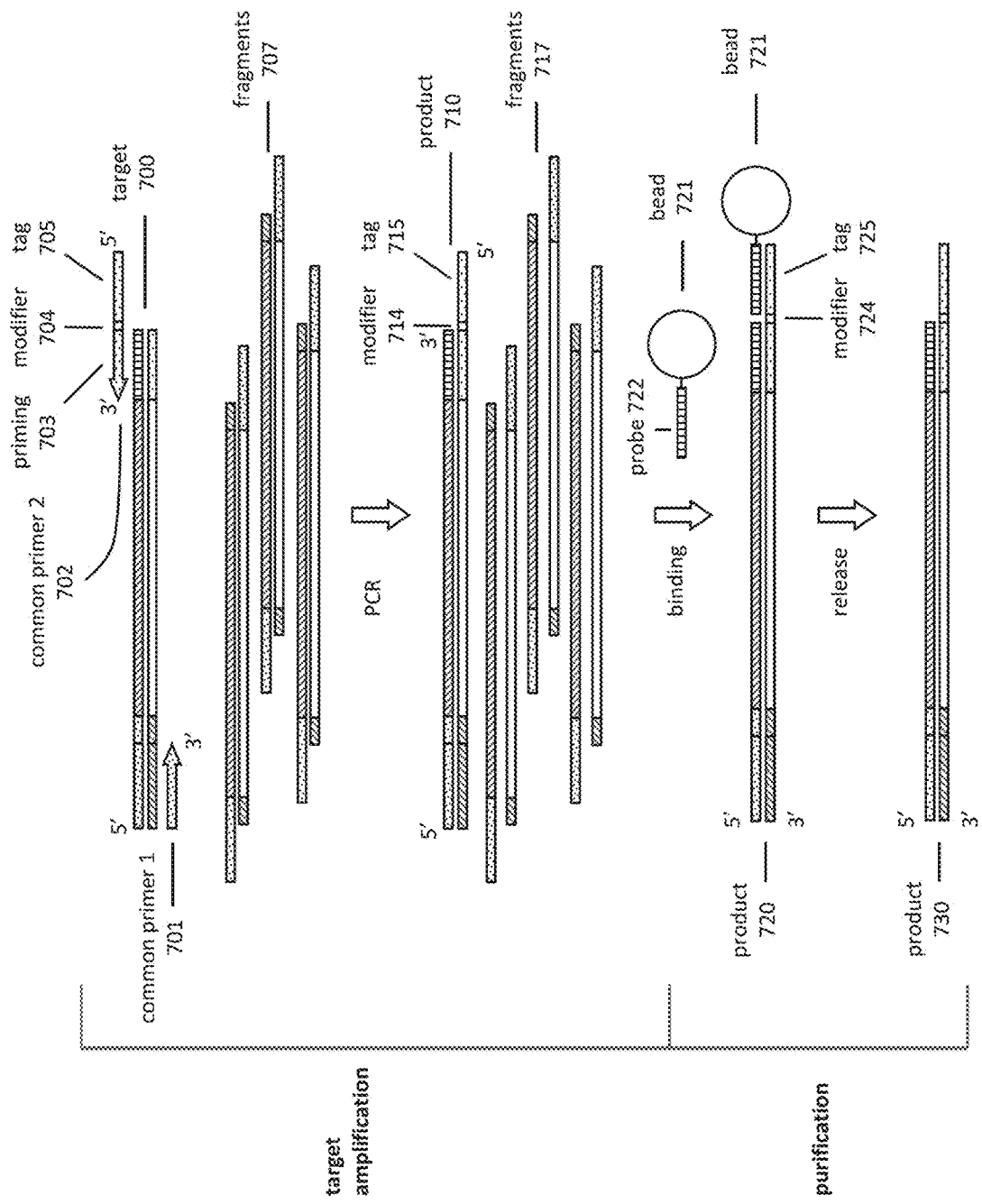
FIG. 7 illustrates an exemplary embodiment of purification method of this invention.

In some embodiments, the relay PCR product solutions are further purified to separate the PCR products 330, 430, 480, 530, and 640 from the rest of the reaction mixture. Various established PCR reaction purification methods and commercial kits can be used for the purpose. These include but not limited to normalization beads from Axygen Biosciences (Union City, Calif.), PCR purification columns from Qiagen (Valencia, Calif.), and gel cut purification. FIG. 7 illustrates an exemplary embodiment of a purification method of this invention. The starting mixture comprises target sequences 700, common primer 1 (701), common primer 2, fragments 707, and polymerase, all in a PCR buffer solution. The target sequences 700 are flanked with priming segments that are either identical or complementary to common primer 1 and common primer 2 and are designed to be amplified by the primers. Fragments 707 do not carry the priming segments and are not expected to be amplified by the primers. This starting mixture is similar to the reaction mixture of FIG. 6 at the end of the cycle 1 reaction. Common primer 2 (702) comprises of a priming segment, a modifier segment 704 and a tag segment 705. The function of the modifier segment 704 is to prohibit the polymerase extension reaction from passing through the segment and/or to facilitate enzymatic, chemical, or photo cleavage at the location. Exemplary embodiments of modifier segment 704 include but not limited to at least one C3 alkyl spacer, at least one ethylene glycol spacer, at least one photo-cleavable spacer, at least one 1',2'-dideoxyribose, and at least one deoxyuridine. The incorporations of these modifiers into oligonucleotides are well known in the field of nucleic acid synthesis and can be performed by commercial suppliers such as Integrated DNA Technologies, Inc. (Coralville, Iowa). In an exemplary embodiment, common primer 2

(702) comprises a hexa-ethylene glycol spacer as the modifier segment 704 that stops polymerase extension reaction from passing through the segment and into tag segment 705. This results in PCR product 710 containing a single strand overhang tag segment 715. In some embodiments the tag segment 705 comprises an oligonucleotide. In some embodiments the tag segment 705 comprises of at least one binding moiety. An exemplary binding moiety is biotin. In some embodiments the tag segment 705 comprises of a combination of an oligonucleotide and a binding moiety. In some embodiments the binding moiety is attached to the 5' end of the tag segment 705 oligonucleotide. In some embodiments, one or more of the above mentioned purification kits or methods are applied to the PCR product solution to remove polymerase and residual single stranded primers. In some applications, such as singular primer extension relay PCR, fragments 717 have an average size that is similar to that of PCR product 710 and an additional or a different purification process is needed to remove fragments 717.

The lower portion of FIG. 7 illustrates an exemplary embodiment of the disclosed purification method involving the direct capture of the PCR product 720. Add probe 722 grafted beads 721 into the PCR product solution or a primer removed PCR product solution. Probe 722 has a sequence that is substantially complementary to that of tag segment 715 and facilitates the capture of the PCR product 720 by the beads 721 through hybridization. Optionally, the solution salt concentration may be adjusted to ensure a sufficient hybridization. Salts include but are not limited to sodium chloride, sodium citrate, sodium phosphate, potassium chloride, potassium phosphate, ammonium chloride, tris chloride, and/or mixture of two or more salts. Agitation and incubation of the solution at room temperature or at a predetermined temperature increase the capture yield. Washing the beads 721 with a hybridization buffer solution removes fragments 717, residual polymerase and free primers while retaining the hybridized PCR products 720. To complete the purification, the beads 721 are placed into an elution buffer and the buffer temperature is elevated to release the PCR product 720 from the beads 721. The immobilization of oligonucleotides to form probe 722 grafted beads 721 and the use of the beads to capture nucleic sequences are well known in the field of biology. An exemplary embodiment uses Dynabeads® MyOne™ Streptavidin C1 from Life Technologies (Grand Island, N.Y.) as beads 721. Sequence designs for the complementary pair of probe 722 and tag segment 705 share many principles and procedures of the hybridization probe designs that are familiar to one skilled in the art. The sequences are designed in such way that a stable hybridization between the pair is achieved during binding process and in the hybridization buffer but denaturation between the pair is achieved during release process. In general, the binding and/or hybridization buffers have a relatively high salt concentration of at least 50 mM, 100 mM, 500 mM, 1M, 2M, or higher. The elution buffer has a relatively low salt concentration of at most 100 mM, 50 mM, 10 mM, 5 mM, 1 mM or lower. In general, the binding temperature is lower than elution temperature. The temperatures are decided based on Tm (melting temperature) of the probe 722/tag 705 pair in the corresponding buffer solutions. A preferred binding temperature is below the Tm of the probe/tag pair in the binding or hybridization buffer. A preferred elution temperature is above the Tm of the probe/tag pair in the elution buffer. In some embodiments, the PCR products 730 remain double stranded after the elution process. In some embodiments, binding temperature is at most 40° C., 35° C., 30° C., 25° C., 22° C., or lower. Elution temperature is at least 30° C., 35° C., 40° C., 45° C., 50° C., 55° C., or higher. Other considerations in the sequence design include the minimizing cross hybridization of the probe 722 sequence to any target sequences and minimizing secondary structure involving tag segment 705.

Alternative embodiments of the disclosed method involve indirect capture of the PCR products 720. In some embodiments, probes 722 are not pre-grafted to beads 721 but rather contain ligand moieties, such as biotin. The beads 721 are coated with capture moieties such as streptavidin. In the embodiments, first, the free probes 722 are hybridized with the tag segments 715. Then the capture moiety coated beads 721 are added to the hybridization solution to capture the PCR product 720. The remaining processes are similar to what described above.

One aspect of the above described purification method is the direct formation of PCR products with single-strand overhangs. The overhangs may be used to facilitate purification. The method makes it possible to release the double stranded product 730 in a mild denaturation condition. By comparison, a regular biotinylated primer, without the modifier segment 704 and tag segment 705, would produce blunt ends. Although the PCR product can be captured by streptavidin coated beads, the release of the product requires strong denature conditions (see user manual of Dynabeads® MyOne™ Streptavidin C1 from Life Technologies, Grand Island, N.Y.) under which the double stranded structure of the PCR product would be denatured as well.

Figure 8:
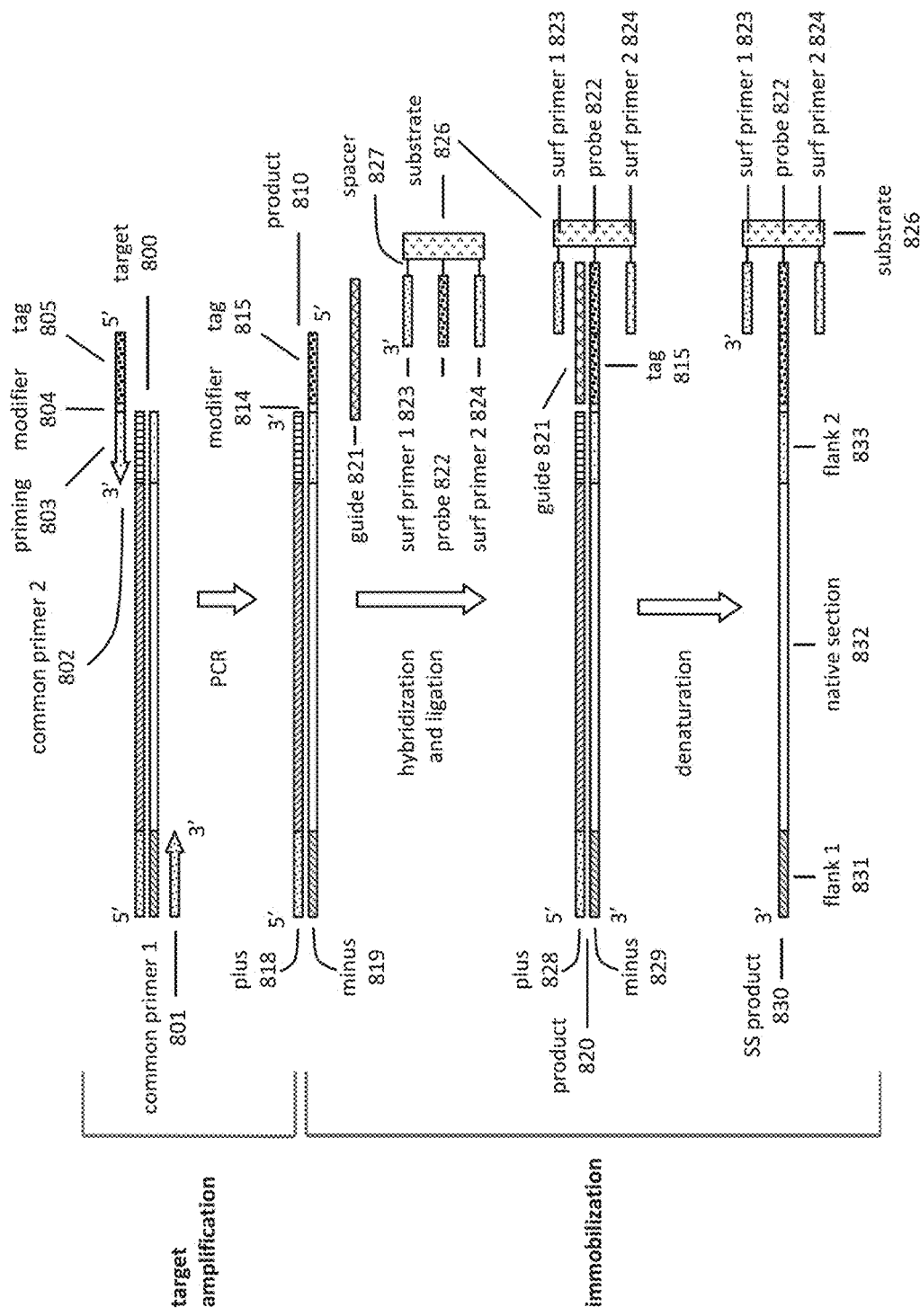
FIG. 8 illustrates an exemplary embodiment of target immobilization method of this invention.

This disclosure describes the use of the single strand overhang containing PCR products in new and improved approaches for library preparation and cluster formation in surface cluster based sequencing (D. Bentley et al. (2008) "Accurate whole human genome sequencing using reversible terminator chemistry" Nature 456 53-59). FIG. 8 schematically illustrates the new approaches. The top of FIG. 8 illustrates target amplification by PCR, which is similar to that of FIG. 7 and has been described above. The target amplification process shown in FIG. 8 is a PCR process for general use, including for sequence library preparation in Next Generation Sequencing (Mardis ER (2008) "Next-generation DNA sequencing methods", Annu Rev Genomics Hum Genet 9: 387-402). One feature of the disclosed method is to produce PCR products 810 that contain single-strand tag 815. In some embodiments, the common primer 2 (802) comprising priming segment 803, modifier segment 804 and tag segment 805 is used as common primer 1 321, 421, 471, 521, and 611 or as common primer 2 322, 422, 472, 523, and 612 in relay PCR processes of FIGS. 3 through 6. The disclosed method further comprises immobilization of the single-strand tag 815 containing PCR products 810 to a substrate for conducting chemical and/or biochemical reactions. As an exemplary illustration, in FIG. 8, a substrate 826 is grafted with probe 822, surface primer 1 (823), and surface primer 2 (824). Depending on applications, the substrate 826 can be made of glass, silicon, polymer, metal or any other appropriate materials. The grafted moieties, probe 822, surface primer 1 (823), and surface primer 2 (824) are oligonucleotides of predetermined sequences. In some embodiments, the grafted moieties further comprise spacer 827 to connect the oligonucleotides to substrate surface. Grafting oligonucleotides to substrate surfaces is a well-known art and has been described in literature (B. Joos et al. (1997) "Covalent attachment of hybridizable oligonucleotides to glass supports" Anal Biochem, 247 96-101; Y. Rogers et al. (1999) "Immobilization of oligonucleotides onto a glass support via disulfide bonds: A method for preparation of DNA microarrays" Anal Biochem, 266 23-30; D. Bentley et al. (2008) "Accurate whole human genome sequencing using reversible terminator chemistry" Nature 456 53-59, Supplementary Information). Immobilization of the PCR products 810 begins with co-hybridization of single-strand tag 815, guide 821, and probe 822. Guide 821 is an oligonucleotide having a portion of the sequence complementary to tag 815 and a portion of the sequence complementary to probe 822. In some embodiments, the co-hybridization is performed by first applying a guide 821 solution to substrate 826 at a sufficiently high guide 821 concentration to substantially hybridize all probes 822 on the substrate and then wash away any extra guide 821 in the solution. This step produces guide/probe pairs on the substrate surface. The co-hybridization is completed by applying a PCR product 810 solution at a sufficiently high PCR product 810 concentration (threshold concentration) to substantially hybridize all the guide/probe pairs. In some embodiments, upon the hybridization, 5' end of tag 815 stacks to 3' end of the probe and there is no gap in between the two ends. In some embodiments, the 5' terminal of tag 815 is phosphorylated and 3' terminal of probe 822 is a hydroxyl group. Tag 815 and probe 822 may be covalently joined together by ligation. In some embodiments, the ligation is done using T4 ligase from NEB (Ipswich, Mass.).

The main considerations for sequence designs of tag 815, probe 822, and guide 821 include melting temperature, sequence uniqueness, and intra-molecular folding. Melting temperatures for both tag/guide and probe/guide pairs should be considerably above both hybridization and ligation temperatures in corresponding buffers so that sufficiently high hybridization yields can be achieved and/or maintained in both reaction conditions. In some embodiments, melting temperatures of probe/guide pair is higher than that of tag/guide pair. All three sequences should have minimal folding under the reaction conditions. All three sequences should be sufficiently different from that of surface primer 1 (823) and surface primer 2 (824) so that no cross hybridization to the two surface primers will take place. Additionally, hybridization temperature, ligation temperature and buffer compositions should be designed in such way that the double stranded structure of PCR product 810 remains stable in both reactions. More accurate sequence and reaction condition designs will be described in later sections of this disclosure.

Alternative methods can be used to join tag 815 and probe 822. In some embodiments, the 5' terminal of tag 815 is an azide group and 3' terminal of probe 822 is an alkyne group. Tag 815 and probe 822 are then joined together using click chemistry as described by R. Kumar el al. (2007) "Template-Directed Oligonucleotide Strand Ligation, Covalent Intramolecular DNA Circularization and Catenation Using Click Chemistry" J. AM. CHEM. SOC. 129, 6859-6864.

In some embodiments, after the tag 815 and the probe 822 are covalently joined, the system, including substrate and immobilized PCR product 820, is placed into a denature buffer and is washed to remove plus strand 828 and guide 821. In some embodiments, the denature buffer comprises high concentration of formamide. The result is a single strand product 830 covalently attached to substrate 826.

In some embodiments, product 830, surface primer 1 (823), and surface primer 2 (824) are subject to further enzymatic and/or chemical reactions to extend the surface primers using the product 830 as initial template thereby producing additional copies of product 830 in the vicinity of the starting product 830 which form surface clusters of the product 830. The parallel copies of product 830 are then used as templates for sequencing. The surface cluster formation and the sequencing process have been described in detail in D. Bentley et al. (2008) "Accurate whole human genome sequencing using reversible terminator chemistry" Nature 456 53-59 and associated supplementary information which are hereby incorporated by reference in their entirety. In some embodiments, the sequence of surface primer 1 (823) is substantially complementary to the sequence of flank 1 (831). In some embodiments, the sequence of surface primer 2 (824) is substantially the same as the sequence of flank 2 (833). In some embodiments, the surface density of surface primer 1 (823) is substantially the same as the surface density of surface primer 2 (824). The definition of the surface density is the number of immobilized molecules per unit surface area. In some embodiments, surface densities of surface primer 1 (823) and surface primer 2 (824) are substantially higher than that of probe 822. In some embodiments, the surface density ratio of surface primer 1 (823) (or surface primer 2 (824)) to probe 822 is at least 1,000, 10,000, 100,000, 1,000,000, 10,000,000, 100,000,000, or greater. In some embodiments, the surface density ratios are controlled by relative concentrations of probe 822, primer 1 (823), and primer 2 (824) mixture solution for the grafting preparation of substrate surface.

Certain aspects of the disclosed method include the addition of probes as well as surface primers to the substrate surface and the use of probe captured sequences as the seeds of cluster formation. In the state of art practice (D. Bentley et al. (2008) "Accurate whole human genome sequencing using reversible terminator chemistry" Nature 456 53-59), the substrate surface may be grafted with only two primers which are present in substantially equal surface densities. The seeding of surface clusters is formed by hybridization between one of the surface primers and one of the flanks of PCR product followed by polymerase extension of the primer. While the surface primers are densely populated on the substrate surface, the seed density is controlled by the solution concentration of the PCR product. Under normal conditions, the end cluster density is proportional to the seed density. In a parallel sequencing process, signals emitted from each cluster are used to derive the sequence of the seed template. In order to obtain reliable signal detection from individual clusters, the distance between adjacent clusters needs to be sufficient, otherwise, signals emitted from adjacent clusters would be inseparable and erroneous sequence reads would be produced. On the other hand, for the purpose of maximizing read throughput it is desirable to increase the cluster density. There is an optimal cluster density. In current practice the optical cluster density is achieved by carefully controlling the PCR product concentration in the clustering solution. The process is time consuming and subjects to measurement instrument and human handling errors. By comparison, in the present method, cluster density is controlled by probe density or surface primer to probe ratio which are fixed during substrate surface preparation by the substrate manufacturer. As result, for the cluster preparation at user's site, as long as the user makes the PCR product concentration beyond a threshold the resulted cluster density will always stay near a fixed value.

In some embodiments, multiple probes 822 of distinct sequences are used. This arrangement is particularly useful when multiple samples are sequenced in parallel. Target amplification is applied on each sample with a unique pair of common primer 1 (801) and common primer 2 (802). The common primers 2 (802) for different samples comprise different tags 805 of distinct sequences. Each unique tag 805 is paired with a unique probe 822 through a unique guide 821. The design considerations of the multiple tags, probes, and guides must include the minimization of cross-hybridization among the sequences. In some embodiments, the number of distinct probes is at least 1, 2, 4, 8, 12, 16, 32, 48, 64, 96, or more. In some embodiments, the surface density of each distinct probe is substantially the same for all probes. In some embodiments, the surface densities of different probes are different. In some embodiments, the surface densities of a selected group of probes are set at predetermined values while the surface densities of the rest of the probes are made substantially equal. In some embodiments, the surface density ratio of surface primer 1 (823) (or surface primer 2 (824)) to the combined probes 822 is at least 1,000, 10,000, 100,000, 1,000,000, 10,000,000, 100,000,000, or greater. In some embodiments, common primer 1 (801) comprises at least one barcode section. In some embodiment, the priming segments of common primer 2 (802) comprises at least one barcode section. The combination of the barcodes in the primers is used to identify the origin of the sample in sequence reads. In an exemplary embodiment of using the multi-probe containing substrate in cluster preparation for multi-sample parallel sequencing, a solution mixture of all involving guides 821 to the substrate 826 is applied to form guide/probe pairs. Any extra guides 821 are then washed away. Then, a solution mixture of tag 815 containing PCR products 810 of all samples is applied to the substrate to complete tag/guide/probe co-hybridization. Ligation, denaturation, and cluster formation are conducted as described above. As result, the number of clusters attributed to each sample is directly related to the number of available sample specific probes on the substrate surface and has little to do the PCR product concentration of the sample, as long as the concentration is above a threshold value. By comparison, the current state of the art cluster preparation methods for multiple sample parallel sequencing requires precision sample quantity normalization for all samples involved and precisely controlled total PCR product concentration. The self-limiting feature of the present methods provide significant advantages over the current method in terms of ease operation, result consistency and overall process robustness.

Polymerase Selection

In some embodiments of the present invention, the amplified products are formed via polymerase chain reaction using one or more DNA polymerases. In some embodiments, the polymerase can be a thermo stable polymerase. In some embodiments, the polymerase can be a hot-start polymerase. In some embodiments, the polymerase can be a high fidelity polymerase. In some embodiments, the polymerase can be a recombinant polymerase. In some embodiments, the polymerase can be a commercially available product such as Platinum® Taq DNA Polymerase (Life Technologies, Grand Island, N.Y.), AccuPrime™ Taq DNA Polymerase (Life Technologies, Grand Island, N.Y.), AmpliTaq Gold® DNA Polymerase (Life Technologies, Grand Island, N.Y.), Taq DNA Polymerase (New England Biolabs, Ipswich, Mass.), OneTaq® DNA Polymerase (New England Biolabs, Ipswich, Mass.), Deep Vent™ DNA Polymerase (New England Biolabs, Ipswich, Mass.), Phusion® Hot Start Flex DNA Polymerase (New England Biolabs, Ipswich, Mass.), Q5® High-Fidelity DNA Polymerase (New England Biolabs, Ipswich, Mass.), PfuTurbo Cx Hotstart DNA Polymerase (Agilent, Santa Clara, Calif.), PfuUltra II Fusion HS DNA Polymerase (Agilent, Santa Clara, Calif.), KAPA HiFi PCR Kits (KAPA Biosystems, Wilmington, Mass.).

In some embodiments of the present invention, one or more hot-start polymerases are advantageously used to minimize potential off-target amplification and primer-dimer formation.

In some embodiments, a new class of thermo-stable high-fidelity polymerases that lacks both strand-displacement activity and 5' to 3' nuclease activity is advantageously used. The lack of strand displacement and 5' to 3' nuclease activity benefits multiplex amplification applications in which two or more target regions are in tandem or in positional proximity. By using these polymerases, primers binding to the middle of the tandem regions will not be displaced or degraded. Commercial products of this new class of thermo-stable high-fidelity polymerases include, but are not limited to, Phusion® Hot Start Flex DNA Polymerase (New England Biolabs, Ipswich, Mass.) and Q5® High-Fidelity DNA Polymerase (New England Biolabs, Ipswich, Mass.).

Reaction Conditions

Reaction conditions are generally governed by polymerases involved, primer thermodynamic properties, target sequence properties, and multiplexity of a multiplex PCR. A relay PCR run includes two functionally different reaction phases, which may require different reaction conditions. The specific reaction conditions for specific applications can be determined by those who are skilled in the art by following specific considerations below, examples at the end of this description, and teachings and references throughout of this specification.

Phase 1 function of a relay PCR is to produce common segment flanked specific target sequences. Corresponding reaction conditions should be designed to achieve the objectives of producing the highest possible yields for on-target replications, minimizing off-target template replications, and minimizing primer-dimer formation. As described in FIG. 3 through FIG. 5, the phase 1 reaction consists of cycle 1 and cycle 2 reactions. In FIG. 6, the phase 1 reaction comprises cycle 1 reaction. Each cycle contains three thermo steps including denaturing, annealing, and extension. The annealing conditions of cycle 1 and cycle 2 require critical considerations. The following principles are used to guide the considerations. The probability of primer-dimer formation increases as the number of specific primers increases (see U. Landegren et al. (1997) "Locked on target: strategies for future gene diagnostics" Ann. Med., 29: 585-590). On the other hand, based on chemical reaction thermodynamics and kinetics (see I. Tinoco et al. (1995) "Physical Chemistry: Principles and Applications in Biological Sciences" Prentice Hall College Div; 3rd edition), the equilibrium product concentrations and the rates of primer-primer as well as on-target primer-template hybridization interactions decrease as the concentrations of the primers decrease. Additionally, based on nucleic hybridization thermodynamic principles (see J. SantaLucia Jr. et al. (2004) "The thermodynamics of DNA structural motifs" Annu. Rev. Biophys. Biomol. Struct. 33:415-440), hybridization stability increases as hybridization temperature decreases and complementary sequence length increases. In general, as the plexity of an amplification reaction increases and/or as the number of specific primers increases, concentration of each individual primer should be decreased to reduce the probability of primer-dimer formation; at the same time the primer concentrations should not be decreased so dramatically that the desired interactions between the primers and templates are not reduced. In such cases where the concentration of the primers are reduced, the annealing time should be increased to compensate for the reduced interaction rate between the primers and the templates. High annealing temperature is generally preferred for obtaining high primer specificity and for minimizing undesirable primer-primer hybridization. The high annealing temperature is also preferred to avoid a net degradation of the primer during a long annealing period when the selected polymerase has a high 3' to 5' nuclease activity. The optimal annealing temperature is generally expected to be found close to the peak polymerase activity temperature within a 10° C. range. The peak polymerase activity temperature can be obtained from corresponding polymerase suppliers.

Exemplary reaction conditions of the present invention are provided in Example I through IV of this description. For high plexity amplification applications, optimal reaction conditions vary significantly from previously known conditions. Target specific primer concentrations are 0.001 nM or lower, 0.01 nM or lower, 0.1 nM or lower, 1 nM or lower, 2 nM or lower, 3 nM or lower, 4 nM or lower or 5 nM or lower. In certain embodiments of the present invention the target specific primer concentrations are from about 0.0001 nM to about 10 nM or from about 0.0001 nM to about 5 nM or from about 0.0001 nM to about 4 nM or from about 0.0001 nM to about 3 nM or from about 0.0001 nM to about 2 nM or from about 0.0001 nm to about 1 nM or from about 0.0001 nm to about 0.1 nM or from about 0.0001 nm to about 0.01 nM or from about 0.0001 nm to about 0.001 nM, or from about 0.001 nM to about 10 nM or from about 0.001 nM to about 5 nM or from about 0.001 nM to about 4 nM or from about 0.001 nM to about 3 nM or from about 0.001 nM to about 2 nM or from about 0.001 nm to about 1 nM or from about 0.001 nm to about 0.1 nM or from about 0.001 nm to about 0.01 nM, or from about 0.01 nM to about 10 nM or from about 0.01 nM to about 5 nM or from about 0.01 nM to about 4 nM or from about 0.01 nM to about 3 nM or from about 0.01 nM to about 2 nM or from about 0.01 nM to about 1 nM or from about 0.01 nM to about 0.1 nM, or from about 0.1 nM to about 10 nM or from about 0.1 nM to about 5 nM or from about 0.1 nM to about 4 nM or from about 0.1 nM to about 3 nM or from about 0.1 nM to about 2 nM or from about 0.1 nM to about 1 nM, or from about 1 nM to about 10 nM or from about 1 nM to about 5 nM or from about 1 nM to about 4 nM or from about 1 nM to about 3 nM or from about 1 nM to about 2 nM. The annealing time may be greater than 5 minutes, greater than 10 minutes, greater than 20 minutes, greater than 30 minutes, greater than 40 minutes, greater than 50 minutes, greater than 60 minutes, greater than 70 minutes, greater than 80 minutes, greater than 90 minutes, greater than 100 minutes, greater than 110 minutes, greater than 120 minutes greater than 130 minutes, greater than 140 minutes, greater than 150 minutes, greater than 160 minutes, greater than 170 minutes, greater than 180 minutes greater than 190 minutes, greater than 200 minutes, greater than 210 minutes, greater than 220 minutes, greater than 230 minutes, greater than 240 minutes. The annealing time may be from about 5 minutes to about 500 minutes, or from about 5 minutes to 400 minutes or from about 5 minutes to about 300 minutes or from about 5 minutes to about 250 minutes or from about 5 minutes to about 200 minutes or from about 5 minutes to about 150 minutes or from about 5 minutes to about 100 minutes or from about 5 minutes to about 50 minutes, or from about 10 minutes to about 500 minutes, or from about 10 minutes to 400 minutes or from about 10 minutes to about 300 minutes or from about 10 minutes to about 250 minutes or from about 10 minutes to about 200 minutes or from about 10 minutes to about 150 minutes or from about 10 minutes to about 100 minutes or from about 10 minutes to about 50 minutes, or from about 20 minutes to about 500 minutes, or from about 20 minutes to 400 minutes or from about 20 minutes to about 300 minutes or from about 20 minutes to about 250 minutes or from about 20 minutes to about 200 minutes or from about 20 minutes to about 150 minutes or from about 20 minutes to about 100 minutes or from about 20 minutes to about 50 minutes, or from about 30 minutes to about 500 minutes, or from about 30 minutes to 400 minutes or from about 30 minutes to about 300 minutes or from about 30 minutes to about 250 minutes or from about 30 minutes to about 200 minutes or from about 30 minutes to about 150 minutes or from about 30 minutes to about 100 minutes or from about 30 minutes to about 50 minutes or from about 40 minutes to about 500 minutes, or from about 40 minutes to 400 minutes or from about 40 minutes to about 300 minutes or from about 40 minutes to about 250 minutes or from about 40 minutes to about 200 minutes or from about 40 minutes to about 150 minutes or from about 40 minutes to about 100 minutes or from about 40 minutes to about 50 minutes, from about 50 minutes to about 500 minutes, or from about 50 minutes to about 400 minutes or from about 50 minutes to about 300 minutes or from about 50 minutes to about 250 minutes or from about 50 minutes to about 200 minutes or from about 50 minutes to about 150 minutes or from about 50 minutes to about 100 minutes or from about 60 minutes to about 500 minutes, or from about 60 minutes to 400 minutes or from about 60 minutes to about 300 minutes or from about 60 minutes to about 250 minutes or from about 60 minutes to about 200 minutes or from about 60 minutes to about 150 minutes or from about 60 minutes to about 100 minutes. High annealing temperatures are preferred. The annealing temperature may be greater than 50° C., or greater than 60° C., or greater than 65° C., or greater than 70° C., or greater than 75° C., or greater than 80° C., or greater than 85° C., or greater than 90° C. The annealing temperature may be from about 50° C. to about 95° C., or from about 50° C. to about 90° C., from about 50° C. to about 85° C., from about 50° C. to about 80° C., from about 50° C. to about 75° C., from about 50° C. to about 70° C., from about 50° C. to about 65° C., from about 50° C. to about 60° C., or from about 55° C. to about 95° C., or from about 55° C. to about 90° C., from about 55° C. to about 85° C., from about 55° C. to about 80° C., from about 55° C. to about 75° C., from about 55° C. to about 70° C., from about 55° C. to about 65° C., from about 55° C. to about 60° C., or from about 60° C. to about 95° C., or from about 60° C. to about 90° C., from about 60° C. to about 85° C., from about 60° C. to about 80° C., from about 60° C. to about 75° C., from about 60° C. to about 70° C., from about 60° C. to about 65° C., or from about 65° C. to about 95° C., or from about 65° C. to about 90° C., from about 65° C. to about 85° C., from about 65° C. to about 80° C., from about 65° C. to about 75° C., from about 65° C. to about 70° C., or from about 70° C. to about 95° C., or from about 70° C. to about 90° C., from about 70° C. to about 85° C., from about 70° C. to about 80° C., from about 70° C. to about 75° C., from about 75° C. to about 95° C., from about 75° C. to about 90° C., from about 75° C. to about 85° C., or from about 75° C. to about 80° C., or from about 80° C. to about 95° C., from about 80° C. to about 90° C., from about 80° C. to about 85° C., or from about 85° C. to about 95° C., from about 85° C. to about 90° C., or from about 90° C. to about 95° C. By comparison, in the previously known conditions target specific primer concentrations are 10 nM to 400 nM; annealing time is between 10 sec and 2 min; and low annealing temperatures are recommended (see Henegariu et al. (1997) "Multiplex PCR: Critical Parameters and Step-by-Step Protocol" BioTechniques 23: 504-511; J. Brownie et al. (1997), in "the elimination of primer-dimer accumulation in PCR" Nucleic Acids Res. 25: 3235-3241; and K. E. Varley et al. (2008) "Nested Patch PCR enables highly multiplexed mutation discovery in candidate Genes" Genome Res. 18:1844-1850; B. Frey et al. (2013) "Methods and amplification of target nucleic acids using a multi-primer approach" US Patent Application Publication US 2013/00045894 A1).

In some embodiments, the concentrations of all specific primers are substantially the same. In some embodiments, the concentrations of different specific primers are different. In some embodiments, the concentrations of a selected number of primers are prepared at predetermined levels and targeted at predetermined section of sample sequences for control purposes and/or for any other desired purposes. In some embodiments, the concentration of a common primer is substantially higher than the concentration of corresponding specific primer. In some embodiments, the concentration of a common primer is at least 50 nM, 100 nM, 200 nM, 500 nM, 1,000 nM, 2,000 nM, 5,000 nM, or higher. The concentration of the common primer may be from about from about 10 nM to about 5000 nM or from about 10 nM to about 1000 nM or from about 10 nM to about 500 nM or from about 10 nM to about 250 nM or from about 10 nM to about 100M or from about 25 nm to about 5000 nM, or from about 25 nM to about 1000 nM or from about 25 nM to about 500 nM or from about 25 nM to about 250 nM or from about 25 nM to about 125 nM or from about 25 nM to about 100 nM or from about 25 nm to about 50 nM or from about 50 nM to about 5000 nM or from about 50 nM to about 1000 nM or from about 50 nM to about 500 nM or from about 50 nM to about 250 nM or from about 50 nM to about 100 nM. In some embodiments, the molar concentration ratio of a common primer to a corresponding specific primer may be at least 10, 20, 50, 100, 200, 500, 1,000, 2,000, 5,000, 10,000, 20,000, 50,000, 500,000 or greater. The ratio of the molar concentration ratio of a common primer to a corresponding specific primer may be between 10 to 5,000,000, or from 10 to 500,000, or from 10 to 50,000 or from 10 to 5,000 or from 10 to 500 or from 10 to 50, or from 50 to 5,000,000 or from 50 to 500,000 or from 50 to 50,000 or from 50 to 5,000 or from 50 to 500, or from 500 to 5,000,000 or from 500 to 500,000 or from 500 to 50,000 or from 500 to 5,000. In some embodiments, the concentration of a specific primer is at most 50 nM, 20 nM, 10 nM, 5 nM, 2 nM, 1 nM, 0.5 nM, 0.2 nM, 0.1 nM, 0.05 nM, 0.02 nM, 0.01 nM, 0.001 nM, or lower.

In some embodiments, annealing temperatures of cycle 1 and cycle 2 are selected to balance 3' to 5' nuclease activity and polymerase activity of the polymerase used. In some embodiments, annealing temperatures of cycle 1 and cycle 2 are selected so that combined result of nuclease activity and polymerase activity of the polymerase used does not cause substantial degradation of specific primers during the annealing period.

In some embodiments of using omega primers and polymerases containing 3' to 5' exonuclease activities, phase I annealing steps consist of two stages of stage 1 and stage 2. The stage 1 temperature is close to or at polymerase extension temperature while the stage 2 temperature is lower than that of stage 1. Stage 1 has a longer time or duration than that of stage 2. Each omega primer is designed such that 5p arm is of sufficient length that at the stage 1 temperature the 5p arm sequence forms a stable hybridization with the corresponding template sequence while 3p arm is sufficiently short that at the stage 1 temperature the 3p arm remains largely in free form (unbound). This condition is designed to minimize 3' exonuclease digestion of the omega primer during the long stage 1 annealing time which is designed so that the template sequence hybridized with the primer at a high ratio. The length of the 3p arm is designed in such a way that at the stage 2 temperature the 3p arm hybridizes to the template.

Reaction conditions for cycle 1 and cycle 2 extension steps and phase 2 thermo cycles may be set using general PCR conditions as found in the product instructions of corresponding polymerase suppliers. In some embodiments, when pluralities of target sequences of high GC contents are involved, extension times may be extended. In some embodiments, the extension time is at least 15 seconds, 30 seconds, 60 seconds, 90 seconds, 120 seconds, or more. Exemplary reaction conditions are provided in the Examples of this description.

In some embodiments, spike-in controls are added into the sample in which multiplex PCR is performed. In one exemplary embodiment, the spike-in controls are chemically synthesized nucleic acids of known sequences. In another exemplary embodiment, the spike-in controls are obtained by extracted biological nucleic acids of known sequences. In another embodiment, the spike-in controls are mixed chemically synthesized nucleic acids and extracted biological nucleic acids of known sequences. The sequences of the spike-in controls may be selected from double stranded nucleic acid sequences, single stranded nucleic acid sequences, sequences containing 3' and 5' ends matching to 3' ends of common primers and being able to be amplified by the common primers, and sequences containing 3' and 5' ends that do not match to 3' ends of common primers but match to corresponding specific primers and can be replicated by the specific primers. In some embodiments, spike-in controls include a plurality of nucleic acid sequences of different GC contents. In one embodiment, the GC contents vary from 15% to 85% or from 15% to 80% or from 15% to 75% or from 15% to 70% or from 15% to 65% or from 15% to 60% or from 20% to 85% or from 20% to 80% or from 20% to 75% or from 20% to 70% or from 20% to 65% or from 20% to 60% or from 25% to 85% or from 15% to 80% or from 25% to 75% or from 25% to 70% or from 25% to 65% or from 25% to 60%. The actual GC content range of the spike-in controls for specific applications can be decided by one skilled in the art of specific applications. In some embodiments, quantitative analysis of amplification product from samples containing spike-in controls is used to optimize reaction conditions. In some embodiments, the quantitative analysis of amplification product from samples containing spike-in controls is used for quality control. In some embodiments, the quantitative analysis of amplification product from samples containing spike-in controls is used to perform quantitative normalization.

Primer Fabrication

In some embodiments, primers may be made by conventional chemical synthesis (L. J. McBride et al. (1983) "An investigation of several deoxynucleoside phosphoramidites useful for synthesizing deoxyoligonucleotides" Tetrahedron Letters, 24:245 248). In some other embodiments, primers are made by chemical synthesis on microarrays (X. Zhou et al. (2004) "Microfluidic PicoArray synthesis of oligodeoxynucleotides and simultaneously assembling of multiple DNA sequences" Nucleic Acids Res. 32:5409-5417; X. Gao et al. "Method and apparatus for chemical and biochemical reactions using photo-generated reagents". U.S. Pat. No. 6,426,184; Gao, X., Zhang, H., Yu, P., LeProust, E., Pellois, J. P. Xiang, Q., Zhou, X. "Linkers and co-coupling agents for optimization of oligonucleotide synthesis and purification on solid supports". U.S. Pat. No. 7,211,654, AU2002305061; Gao, X., Zhou, X., Cai, S.-Y, You, Q., Zhang, X. "Array oligomer synthesis and use" WO2004/039953). The synthesis on microarrays has the advantage of low per sequence cost and is particularly advantageous in high multiplex PCR applications wherein at least 10, 50, 100, 500, 1,000, 5,000, 10,000, 50,000, or 100,000 primer sequences are required. Microarray synthesized oligonucleotide mixtures under the product name of OligoMix™ are commercial available from LC Sciences (Houston, Tex.).

Figure 9:
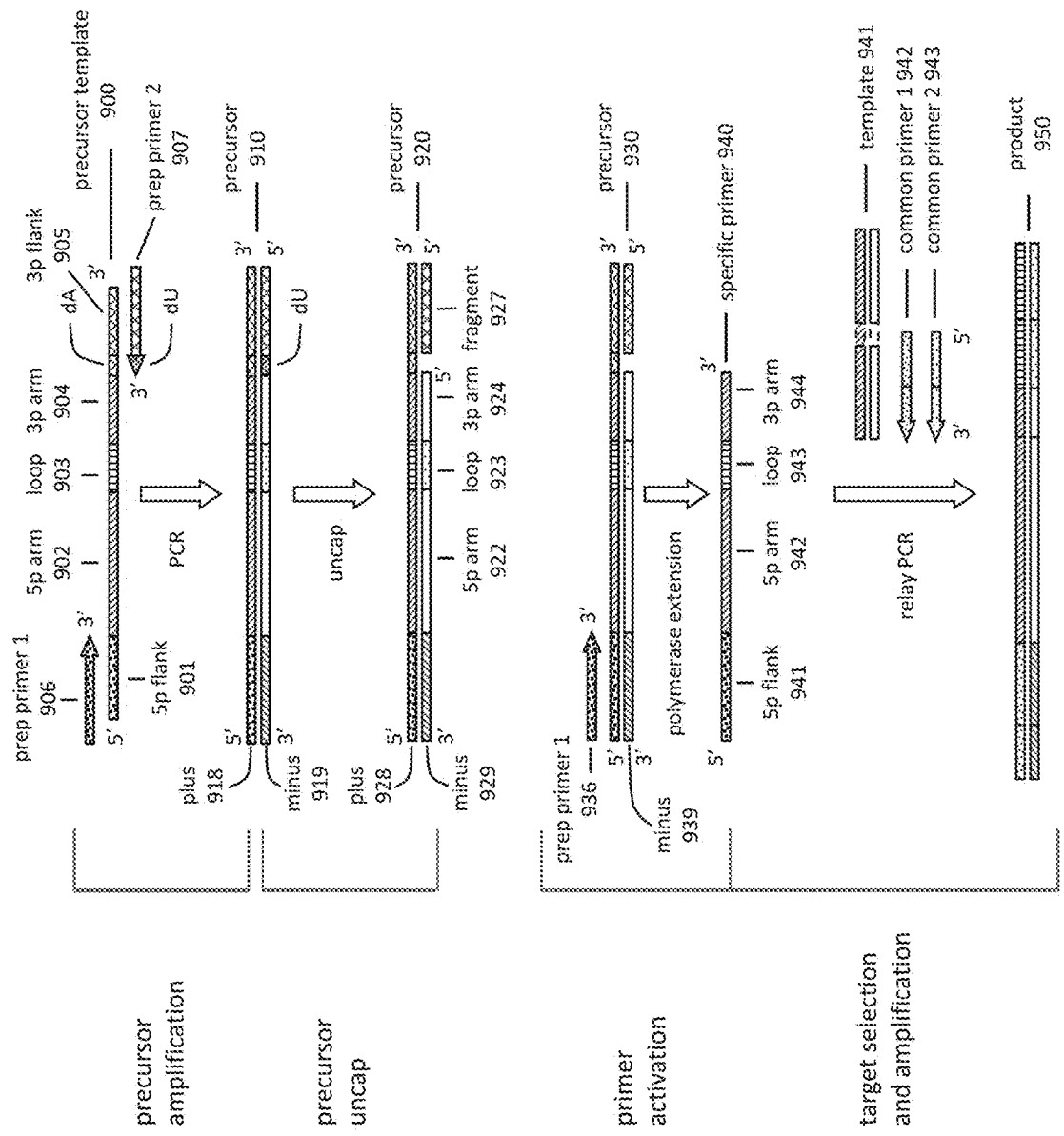
FIG. 9 illustrates an exemplary embodiment of producing specific primers involving precursor amplification and activation.

In some embodiments, synthetic oligonucleotides are amplified before being used as PCR primers. Amplification is preferred when chemical synthesis scale is low, such as the case of chemical synthesis on microarrays. FIG. 9 illustrates an exemplary embodiment of producing specific primers by amplification. Primer precursor templates 900 are chemically synthesized using either the convention method of the above microarray method. Each primer precursor template 900 is an oligonucleotide comprising a number of functional segments including 5p flank 901, 5p arm 902, loop 903, 3p arm 904, and 3p flank 905. At the 5' end of 3p flank segment 905 is a dA (deoxyadenosine) nucleotide. For illustration purpose, the primer precursor template 900 shown in FIG. 9 is designed for preparing omega primers. However, the template design can be made for preparing regular primers as well by simply replacing the section between 5p flank 901 and 3p flank 905 with regular primer segments (e.g. specific segment 341 and common segment 342 of FIG. 3). Two preparation primers, prep primer 1 (906) and prep primer 2 (907) are used for PCR amplification. The sequence of prep primer 1 (906) is substantially the same as that of 5p flank 901. The sequence of prep primer 2 (907) is substantially complementary to that of 3p flank 905. Additionally, the 3' end of prep primer 2 (907) is a dU (deoxyuridine) nucleotide. Although only one primer precursor template 900 is drawn in FIG. 9, the amplification is intended for simultaneous amplification of multiple primer precursor templates 900 to produce the specific primers for multiple target selection and library amplification. All individual primer precursor templates 900 have the same pair of 5p flank and 3p flank segments but have a specific primer section in the middle. The use the dU containing primer requires PCR polymerases to have the ability to read through uracils. Acceptable polymerases include but are not limited to Hot Start Taq DNA Polymerase from NEB (Ipswich, Mass.) and PfuTurbo Cx Hotstart DNA Polymerase from Agilent (Santa Clara, Calif.). Measures should be taken to minimize sequence bias and to avoid PCR product cross hybridization during the PCR amplification of the mixed templates. Hot start polymerases are preferred. Melting temperatures of prep primer 1 906 as well as prep primer 2 907 are preferably 5° C. or more above the highest extension temperature suggested by the polymerase manufacture so that both PCR annealing and extension temperatures can be maximized. Low PCR cycle numbers are preferred. In some embodiments, the cycle number is at most 25, 24, 23, 22, 21, 20, 19, 18, 17, 16, 15, or lower. At the completion of precursor amplification, double stranded precursor 910 is produced.

The next step is to uncap the precursor, in which the dU in the minus strand 919 of precursor 910 is digested in a UDG/EDA (uracil-DNA glycosylase/ethylene diamine) solution. Alternatively, dU may be digested using USER™ (Uracil-Specific Excision Reagent) Enzyme from NEB (Ipswich, Mass.). In some embodiments, a purification process is applied after the digestion to remove the digestion enzymes and/or to change buffer compositions. The purification methods include but are not limited to normalization beads from Axygen Biosciences (Union City, Calif.), PCR purification columns from Qiagen (Valencia, Calif.), and gel cut purification. In the digested precursor 920, 5' end of 3p arm 924 of the minus strand 929 is uncapped. Although FIG. 9 depicts the fragment 927 as being hybridized to the plus strand 928 of precursor 920, in some embodiments the fragment 927 is dissociated from the plus strand 928 either during digestion or during purification.

The lower portion of FIG. 9 illustrates how to activate the digested precursors into specific primers and how to integrate the activation process with target selection and amplification processes. The three functionally distinct processes, primer activation, target selection, and amplification may be carried out in a single tube. An exemplary starting reaction mixture comprises the digested precursors 930, prep primer 1 (936), templates 941, common primer 1 (942), common primer 2 (943), one or more DNA polymerases, and dNTP containing PCR buffer. The digested precursors 930 are the same as the digested precursors 920 and the prep primer 1 (936) is the same as primer 1 906. Suitable concentrations of the digested precursors 930 and the prep primer 1 (936) are similar to that of specific primers and common primers which have been described in section "Reaction conditions". Other components are used to carry out relay PCR in a similar fashion as described above and their suitable concentrations have been describe in section "Reaction conditions". The reaction is carried out on a PCR machine. In the first cycle, prep primer 1 (936) anneals with minus strands 939 and then is extended to form activated specific primers 940 that have extendable 3p arms. Starting from the second cycle the reaction proceeds as a relay PCR process in the same fashions as describe in previous sections and as illustrated in FIGS. 3, 4, 5 and 6. One aspect of this method is the in situ production of active specific primers. The advantage of the method is the simplicity of the process and the minimum number of steps involved.

Figure 10:
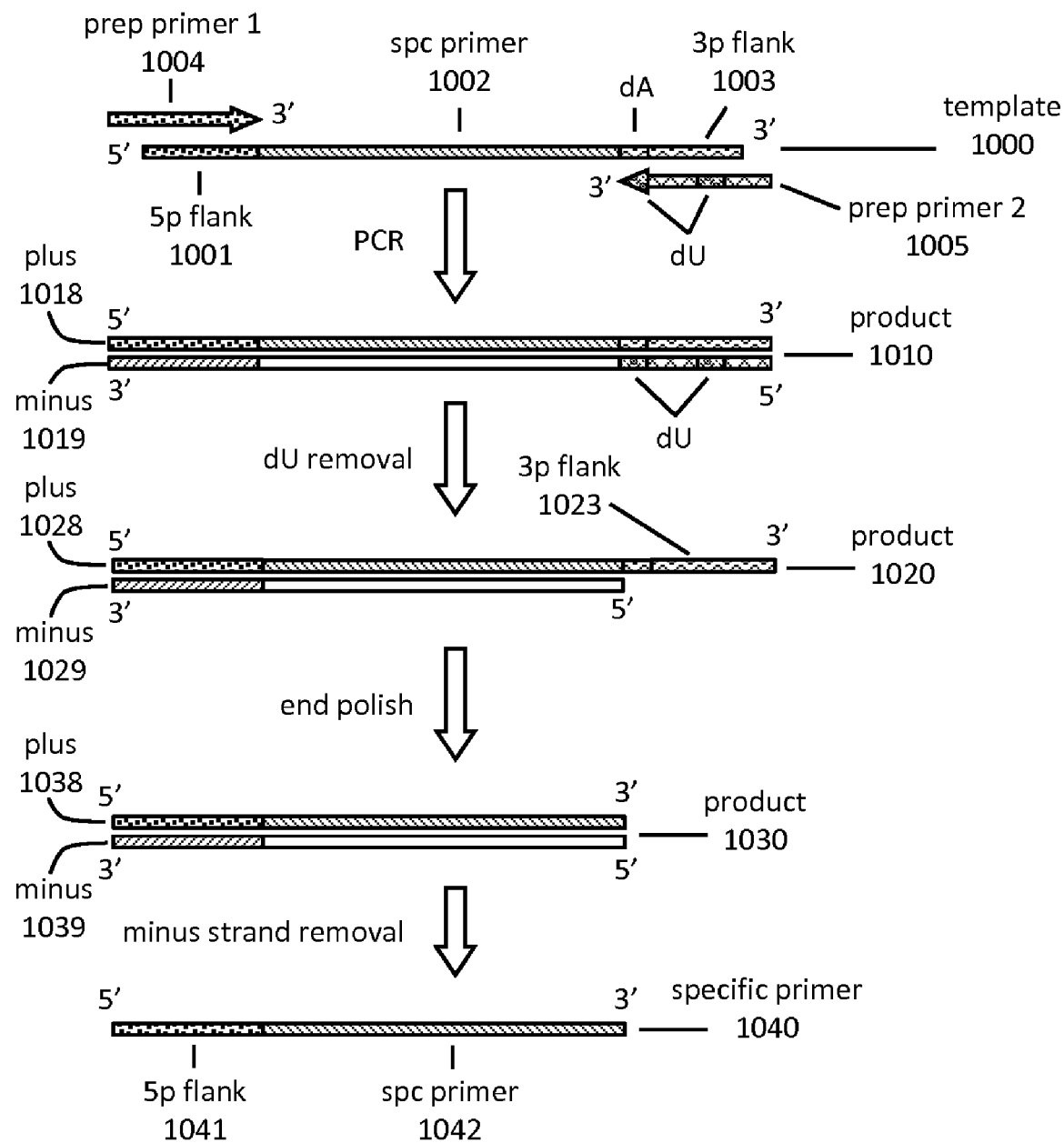
FIG. 10 illustrates an exemplary embodiment of producing specific primers involving PCR amplification and cap removal by dU digestion.

FIG. 10 illustrates another exemplary embodiment of producing specific primers by amplification. A PCR template 1000 comprises spc primer segment 1002 for specific primer, 5p flank segment 1001, and 3p flank 1003. At the 5' end of 3p flank segment 1003 is a dA (deoxyadenosine) nucleotide. The spc primer segment 1002 can be the sequence of a regular specific primer, an omega specific primer, or any nucleotide sequence. Two preparation primers, prep primer 1 (1004) and prep primer 2 (1005) are used for PCR amplification. The prep primer 1 (1004) comprises a 3' section of which the sequence is substantially the same as that of 5p flank 1001. The prep primer 2 (1005) comprises a 3' section of which the sequence is substantially complementary to that of 3p flank 1003. The prep primer 2 (1005) further comprises a dU (deoxyuridine) at its 3' terminal. In some embodiments, it is preferred to have one or more dUs incorporated in to mid-section of prep primer 2 (1005). In some embodiments, multiple PCR templates 1000 are included in the process with each template comprising distinct spc primer segment 1002 but identical 5p flank segment 1001 and identical 3p flank segment 1003. Suitable PCR conditions have been described above relating to the process of FIG. 9. At the completion of PCR amplification, double stranded product 1010 is produced.

The next step is to remove dUs in the minus strand 1019 of the double stranded PCR product 1010. In some embodiments, dUs are removed or digested in a UDG (uracil-DNA glycosylase) solution to remove uracile base and then in EDA (ethylene diamine) solution to scissor nucleotide backbone. In some embodiments, dUs are digested using USER™ (Uracil-Specific Excision Reagent) Enzyme from NEB (Ipswich, Mass.). Both digestion processes produce minus strand 1029 with preferred phosphorylated 5' terminals. In some embodiments, a purification process is applied after the digestion to remove the digestion enzymes and/or to change buffer compositions. The purification methods include but not limited to normalization beads from Axygen Biosciences (Union City, Calif.), PCR purification columns from Qiagen (Valencia, Calif.), and gel cut purification. In some preferred embodiments, one or more dUs having been incorporated into mid-section of prep primer 2 (1005), remaining fragments of prep primer 2 are too short to stay on plus strand 1028 and a single stranded 3p flank 1023 is obtained.

The next step is to end polish product 1020 by removing the single stranded 3p flank 1023. The requirements for the end polish process are to produce a blunt ended double stranded product 1030 with the 3' end of the plus strand 1038 to be the same as the 3' end of spc primer 1002 and to keep the phosphorylated 5' terminal of minus strand 1039 intact. In an exemplary embodiment, the end polish is performed using T4 DNA polymerase from NEB (Ipswich, Mass.). T4 DNA polymerase has a 3' to 5' exonuclease activity and does not have a 5' to 3' exonuclease function. The plus strand 1038 in the end polish product 1030 has a hydroxyl 3' terminal and can be used as an active specific primer in relay PCR. The efficiency of the specific primer can be improved by removing the counter strand of the active primer. The final step is to remove the minus strand 1039. In some embodiments, the minus strand 1039 is removed enzymatically. In an exemplary embodiment, Lambda exonuclease from NEB (Ipswich, Mass.) is used to digest the minus strand 1039. The final product for this fabrication process is single stranded specific primer 1040.

Figure 11:
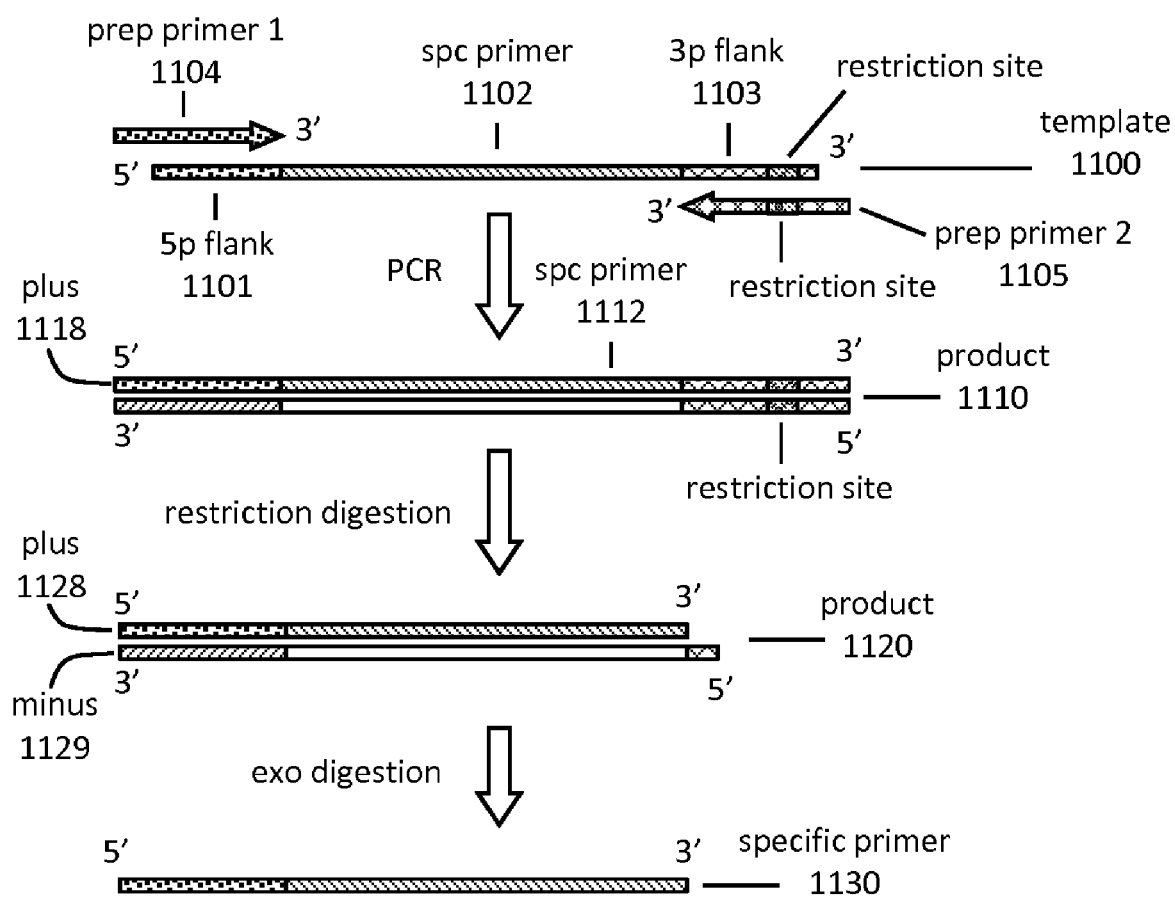
FIG. 11 illustrates an exemplary embodiment of producing specific primers involving PCR amplification and cap removal by restriction digestion.

FIG. 11 illustrates another embodiment of producing specific primers by amplification. A PCR template 1100 comprises spc primer segment 1102 for specific primer, 5p flank segment 1101, and 3p flank 1103. In some embodiments, the 3p flank segment 1103 comprises one or more restriction sites to be recognized by one or more restriction enzymes. The spc primer segment 1102 can be the sequence of a regular specific primer, an omega specific primer, or any nucleotide sequence. Two preparation primers, prep primer 1 (1104) and prep primer 2 (1105) are used for PCR amplification. The prep primer 1 (1104) comprises a 3' section of which the sequence is substantially the same as that of 5p flank 1101. The prep primer 2 (1105) comprises a 3' section of which the sequence is substantially complementary to that of 3p flank 1103. The prep primer 2 (1105) further comprises one or more restriction sites. In some embodiments, multiple PCR templates 1100 are included in the process with each template comprising distinct spc primer segment 1102 but identical 5p flank segment 1101 and identical 3p flank segment 1103. As compared to the PCR reactions of FIG. 9 and FIG. 10, the PCR components of FIG. 11 do not require dU, therefore the PCR polymerases used in the method do not require the ability to read through uracils. Suitable polymerases have been described in above "Polymerase selection" section. Measures should be taken to minimize sequence bias and to avoid PCR product cross hybridization during the PCR amplification of the mixed templates. Hot start polymerases are preferred. Prep primer 1 (1104) as well as prep primer 2 (1105) are preferably designed in such a way that PCR annealing and extension temperatures can be used at the highest possible levels. Later sections of this disclosure will provide detailed descriptions on primer designs. Low PCR cycle numbers are preferred. In some embodiments, the cycle number is at most 25, 24, 23, 22, 21, 20, 19, 18, 17, 16, 15, or lower. At the completion of precursor amplification, double stranded product 1110 is produced.

The next step is restriction digestion. This step is to remove 3p flank 1103 from plus strand 1118 of the double stranded PCR product 1110 so as to expose the 3' end of spc primer segment. In some embodiments, one or more restriction enzymes are used to carry out the digestion. In some embodiments, type IIS restriction enzymes (A. Pingoud et al. (2001) "Structure and function of type II restriction endonucleases" Nucleic Acids Res. 29 3705-3727) are utilized. In some embodiments, restriction enzymes are obtained from commercial suppliers, such as NEB (Ipswich, Mass.). Exemplary restriction enzymes include but are not limited to BspQI, SapI, BsaI-HF, BpuEI, BfuAI, AcuI, and BtsII from NEB (Ipswich, Mass.). In some embodiments, one of the considerations in the design of the template 1100, prep primer 1, and prep primer 2 is to confine the recognition site sequence in 3p flank 1103 and prep primer 2 and avoid the recognition site sequence in any other sections of the template 1100 and in prep primer 1 1104. In preferred embodiments, in the digestion product 1120, 3' end of the plus strand 1128 is the same as the 3' end of spc primer 1112. In preferred embodiments, in the digestion product 1120, 5' terminal of minus strand 1129 is phosphorylated and 3' terminal of plus strand 1128 is a hydroxyl group.

The plus strand 1128 of the digestion product 1120 has a hydroxyl 3' terminal and can be used as an active specific primer in relay PCR. The efficiency of the specific primer can be improved by removing the counter strand of the active primer. The final step is to remove the minus strand 1129. In some embodiments, the minus strand 1129 is removed enzymatically. In an exemplary embodiment, Lambda exonuclease from NEB (Ipswich, Mass.) is used to digest the minus strand 1129. The final product for this fabrication process is single stranded specific primer 1130.

Primer and Target Sequence Design

In certain embodiments the form of specific primers consists of two functionally different sections, as shown in FIG. 3. The 3' section is target specific segment and 5' section is common segment. In some embodiments, the omega form of the specific primers consists of three functionally different sections as shown in FIGS. 4A and 4B. The 3p arm is the first target specific segment; the loop section is a common segment; and 5p arm is the second target specific segment. In some embodiments, as shown in FIGS. 3, 4A, 4B, and 5, the common primers consist of two sections. The 3' section is a common segment and 5' section is a tail segment.

In some embodiments, one pair of common primers is used. A pair normally consists of common primer 1 and common primer 2 where common primers 1 and 2 consist of common segments 1 and 2 and tail segments 1 and 2, respectively. In embodiments using a regular form of specific primers, each pair of specific primers should contain a first specific primer consisting of the common segment 1 and a first target specific segment and a second specific primer consisting of the common segment 2 and a second target specific segment. In embodiments using the omega form of the specific primers, each pair of specific primers should contain a first specific primer consisting of the common segment 1, a first 3p arm, and a first 5p arm and a second specific primer consisting of the common segment 2, a second 3p arm, and a second 5p arm.

In some embodiments, two or more pairs of common primers may be used. Then, a corresponding set of pairs of specific primers are used with each pair of the common primers having a corresponding set of specific primers. The composition and relationship among each set of the common primers and specific primers are the same as described in the above paragraph.

In general, common segment sequences of specific primers and common primers are designed to exhibit the following characteristics: (i) they should have no substantial hybridization to any expected or suspected sequences in the samples of interest; (ii) they should have no substantial hybridization to themselves or to each other; and (iii) they should have no stable secondary structure. Additionally, 3' ends of the common primers should produce substantially stable hybridization. This is generally achieved by having an adequate GC contents at the 3' ends. The length and GC contents of the common segments of the common primers should be designed to have melting temperatures no less than the phase 2 thermo cycle annealing temperature.

In some embodiments, the present invention is used to prepare samples for massive parallel sequencing applications. The tail segments of the common primers are designed to accommodate clonal emulsion amplification, clonal bridge amplification, and/or any other reactions involved in sequencing template preparation processes (E. R. Mardis (2008) "Next-Generation DNA Sequencing Methods" Annu. Rev. Genomics Hum. Genet. 9:387-402). In some embodiments, the tail segments of the common primers contain DNA barcode.

In general, the sequence of the target specific segment of a regular form specific primer is substantially identical or complementary to a selected portion of a target sequence of interest. The sequence is selected to exhibit the following characteristics: (i) it should have minimal hybridization to any other portions of expected or suspected sequences in the samples of interest; (ii) it should have no substantial hybridization to other specific primers, to common primers, and to itself; (iii) 3' end of the primer should produce substantially stable hybridization with template; (iv) it should be sufficiently long so as to form substantially stable hybridization with corresponding template at corresponding annealing condition; and (v) the specific primer as whole (including specific and common segments) should have no stable secondary structure.

The principles of selecting the sequences of 3p and 5p arms of omega specific primers are similar to that for regular form specific primers depicted in the above paragraph. Following additional considerations are directed towards the formation of omega forms. (i) Loop should have minimal hybridization to any portions of expected or suspected sequences in the samples of interest. (ii) The lengths of 3p arm and 5p arm should be sufficiently long so that simultaneous hybridizations of both 3p arm and 5p arm to corresponding template are substantially stable at corresponding annealing condition. These structures are formed by hybridization interactions between primer and template sequences and they can be designed with theoretical calculations by those of skilled in the art (see J. SantaLucia Jr. et al. (2004) "The thermodynamics of DNA structural motifs" Annu. Rev. Biophys. Biomol. Struct. 33:415-440).

In some embodiments, specific and/or common primers contain modified nucleotides for performance improvement and/or specific applications. In an exemplary embodiment, 3' ends of the primers are made of phosphorothioate modified nucleotides. In one aspect, the phosphorothioate modified nucleotides inhibit exonuclease degradation. In some embodiments, the number of phosphorothioate modified nucleotides at 3' is at least 1, 2, 3, or more.

Computation Methods

Figure 12:
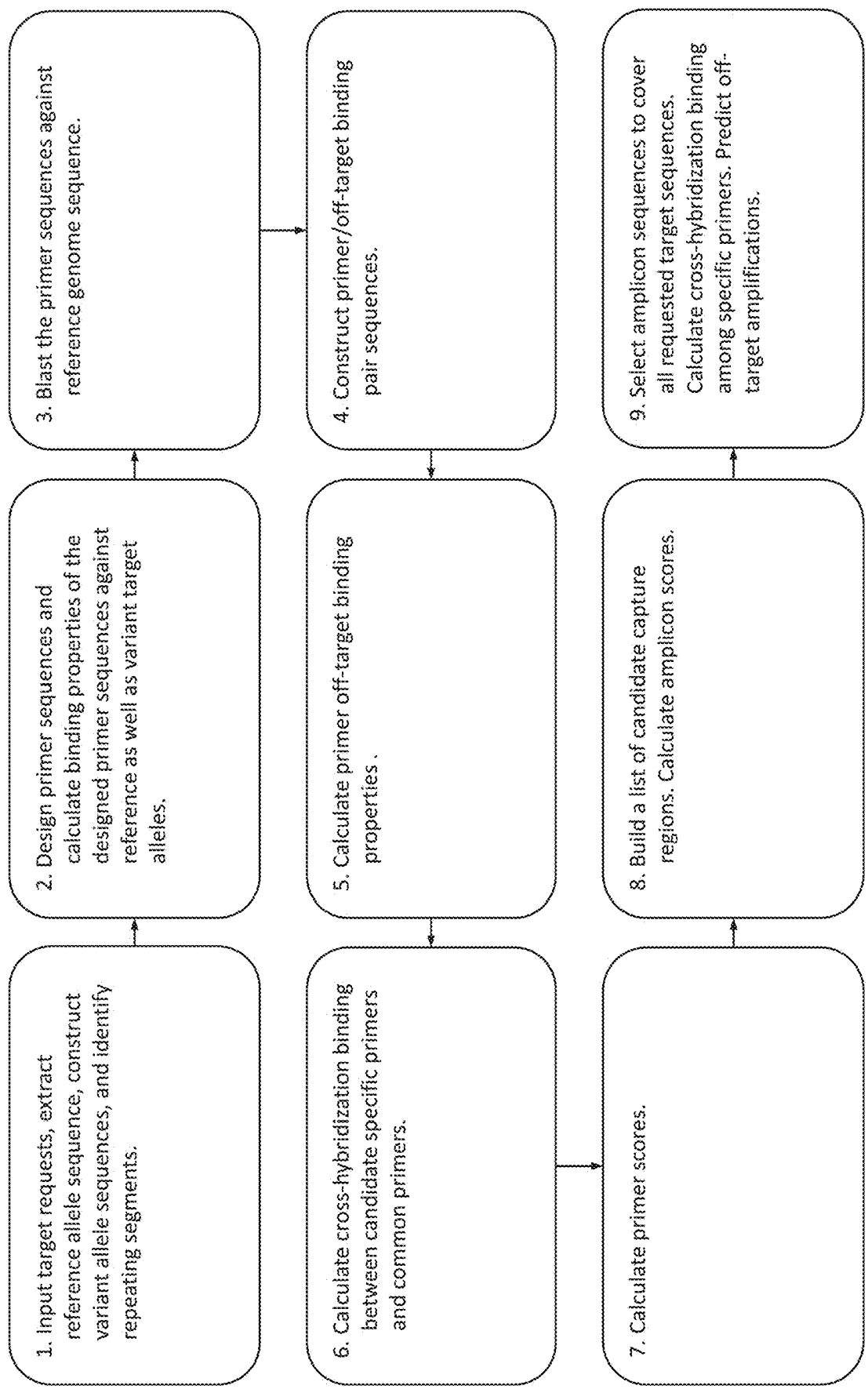
FIG. 12 shows a computation flow chart for primer design.

This disclosure describes a rigorous PCR primer design method. One aspect of the method is the use of rigorous thermodynamic calculations to quantitatively predict primer performances including on-target primer/target binding coefficient, priming efficiency, off-target extension probability, and primer-dimer formation probability. The quantitative aspect of the disclosed method is a significant improvement over the state of art primer design methods and/or tools which are largely qualitative methods using empirically formulated scores to decide primer selections (A. Untergasser et al. (2012) "Primer3-new capabilities and interfaces" Nucleic Acids Res. 40:e115). Another aspect of the method is the design of variant tolerant primers to achieve robust performance on samples from general populations. FIG. 12 depicts a flowchart of the disclosed computation process. In the following description, human genome related sequences are mostly used as examples. However, the disclosed method can be used to design primers for any species including artificial target sequences. This section of the specification involves bioinformatics and thermodynamics. The disclosed methods can be utilized to design PCR primers by those who are skilled in the art.

Step 1 of the primer design process is to prepare primer binding template sequences. The input data are user defined target regions including database version, chromosome number, start and end positions of the target regions. The input data may also include user supplied sequence variations in the target regions. In a preferred embodiment, a user provides sequence variations of individual specimens or patients. In some embodiments, when the sequence variations from individual specimens are not available, a user may provide combined sequence variations. In some embodiments, a user may choose an alternative target sequence input format by directly providing individual target sequences.

Figure 13:
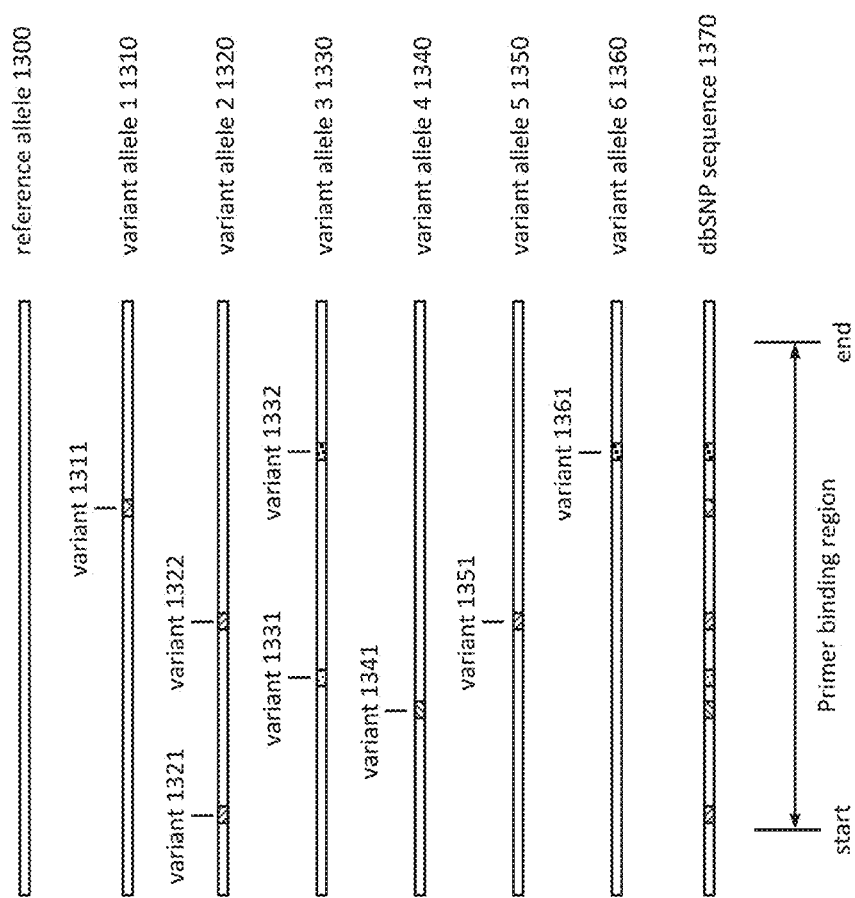
FIG. 13 illustrates an assembly of variant alleles in a genomic region.

Based on the input data of target information, primer binding template sequences for specific primer design are extracted from reference sequence database. The region of each primer binding template sequence exceeds the corresponding target region by extending both ends of the target region so that sufficient room is available to place the primers for capturing the entire target region. In some embodiments, the extension length is at least 50, 75, 100, 125, 150, 200, 250, or more. In some embodiments, where specific primers are used for preparing libraries for high-throughput sequencing use, the extension length is selected to be approximate to the read length of the sequencing run. The reference sequence database can be chosen from various public and private sources. Exemplary reference databases include Genome Reference Consortium GRCh37 and GRCh38 for human genome, GRCm38 for mouse genome, and CRCz10 for zebra fish genome. In a preferred embodiment, reference sequence databases with repeating sequences soft-masked may be used. The soft-masking converts repeating sequences into lower case letters while maintaining the rest of sequences in upper case letters. The extracted reference sequence is shown in FIG. 13 as reference allele 1300.

In some embodiments, when primers are designed for large populations, it is preferred to include variant sequences in the primer binding template regions whenever the variant data is available. Variant databases may be obtained either from public or private sources. A preferred type of variant database comprises variants of individual specimens. An even more preferred type of variant database comprises haplotype variants of individual specimens. In this regard, the 1000 Genomes Project has produced and released a haplotype variant database of human genome (G. McVean et al. (2012) "An integrated map of genetic variation from 1,092 human genomes" Nature, 491, 56-69). Alternatively, when variant database of individual specimens is not available, a variant database of combined specimens can be used. In this regard, dbSNP build 138 available from UCSC Genome Browser for human SNP database is a combined variant database.

Variant sequences in the primer binding template region are extracted from the best available variant database. In an exemplary embodiment, the variant sequences in the regions of interest are extracted from Human 1000 Genome database using VCF tools. The extracted data comprises haplotype data of more than 1,000 individuals. In some embodiments, the extracted data is compiled into a list of unique haplotypes with allele frequencies above a predetermined threshold value. In some embodiments, the predetermined threshold value is at most 10%, 5%, 1%, 0.5%, or lower. In some embodiments, the compiled haplotype data is formatted into variant alleles 1310, 1320, 1330, 1340, 1350, and 1360 that are aligned to the reference allele 1300 of the primer binding templates as shown in FIG. 13. These variant alleles are useful in the design of specific primer sequences that satisfies the requirement of certain percentage of success in a given population. In another exemplary embodiment, the variant sequences in the regions of interest are extracted from a dbSNP by direct reading from fasta files. The extracted dbSNP sequence 1370 is aligned to reference allele 1300. In some embodiments, when user supplied variant sequences are present, the variant sequences are compiled in a similar fashion as described above.

Next, the reference primer binding template sequences are profiled. This is to identify any sequence features that will require special considerations during the determination of start and end positions of individual amplicons. In some embodiments, the profiling includes the identification of masked repeating sequences and homologous sections. The locations of the masked repeating sequences within individual reference primer binding template sequences are extracted and compiled in a data table for later use. The homologous sections within as well as across individual reference primer binding template sequences are identified by alignment. In some embodiments, the alignment is performed using alignment tools such as BLAST from NIH. In some embodiments, the length of the homologous sections to be identified is at least 50, 75, 100, 150, 200, 250, 300, 400, 500, or more. In some embodiments, the length of the homologous sections to be identified is at least the average length of the captured regions. In some embodiments, the average length of the captured regions is predetermined by the primer designer based on specific application requirements. The locations of the homologous sections within individual reference primer binding template sequences are compiled in a target data table for later use.

Step 2 of the primer design process is to design primer sequences and to calculate primer binding properties against reference as well as variant target alleles. Primer sequences are derived from rigorous thermodynamic calculations under the guidance of a predetermined set of parameters. In some embodiments, the sequences of binding sections of each specific primer are determined by the sequence of corresponding reference allele 1300. In some embodiments, the sequences of binding sections of some specific primers are determined by the sequence of certain variant alleles (e.g. 1310, 1320, 1330, 1340, 1350, or 1360, FIG. 13) of interest. The disclosed method includes a number of principle calculations that can be used individually or in combination to design regular primers, omega primers, any other forms of primers, and/or hybridization probes.

In an exemplary embodiment, a regular specific primer is designed. As described in previous sections relating to FIG. 3, a regular specific primer comprises a specific segment 341 and a common segment 342. The common segment is a given sequence in this exemplary embodiment. Below is described how to design the sequence of the specific segment and how to evaluate its priming performance: 1) fix 3' position of the primer at a predetermined location of the reference primer binding template; 2) determine the strand of the template; 3) determine a suitable length of the specific segment that would produce a sufficient fraction of template being hybridized by the primer, under the predetermined conditions of template concentration, primer concentration, buffer salt (including e.g. Na+ and Mg++) concentrations, and annealing temperature; 4) starting with a predetermined minimum length, extract the complementary sequence of the template with the given strand, the given starting position, and the given length (in some embodiments, the minimum length is at most 20 nucleotides, 15 nucleotides, 10 nucleotides, or less); 5) append the extracted sequence to the 3' end of the common segment to form the initial trial sequence; 6) calculate the binding free energy $\Delta G$ between the trial sequence and the template sequence. In some embodiments, the binding free energy is calculated using nearest neighborhood method (see J. SantaLucia Jr. et al. (2004) "The thermodynamics of DNA structural motifs" Annu. Rev. Biophys. Biomol. Struct. 33:415-440). In some embodiments the binding free energy is calculated using a computation package such as UNAFold (N. Markham and M. Zuker (2008) UNAFold: software for nucleic acid folding and hybridization. In Keith, J. M., editor, Bioinformatics, Volume II. Structure, Function and Applications, number 453 in Methods in Molecular Biology, chapter 1, pages 3-31. Humana Press, Totowa, N.J. ISBN 978-1-60327-428-9.). From the free energy $\Delta G$, template association fraction $f_a$ (Equation 7) is derived from hybridization equilibrium equation (Equations 1 and 5), mass balance equations (Equations 2, 3, and 4), and thermodynamic equilibrium constant equation (Equation 6).

$$C_t + C_p \overset{K_a}{\Leftrightarrow} C_c \qquad \text{Equation 1}$$

$$C_c = f_a C_{t_0} \qquad \text{Equation 2}$$

$$C_t = (1 - f_a) C_{t_0} \qquad \text{Equation 3}$$

$$C_p = C_{p_0} - f_a C_{t_0} \qquad \text{Equation 4}$$

$$K_a = \frac{C_c}{C_t C_p} = \frac{f_a}{(1 - f_a)(C_{p_0} - f_a C_{t_0})} \qquad \text{Equation 5}$$

$$K_a = e^{\frac{-\Delta G}{RT}} \qquad \text{Equation 6}$$

$$f_a \approx \frac{1}{\frac{1}{C_{p_0} K_a} + 1} = \frac{1}{\frac{1}{C_{p_0} e^{\frac{-\Delta G}{RT}}} + 1} \qquad \text{Equation 7}$$

In the equations, $C_t$, $C_p$, and $C_c$ are template, primer, and primer-template complex concentrations, respectively, at equilibrium state; $C_{t0}$ and $C_{p0}$ are the initial template and primer concentrations, respectively; $K_a$ is equilibrium constant; T is annealing temperature; and R is ideal gas constant. Equation 7 is derived from Equations 5 and 6 assuming that initial template concentration $C_{t0}$ is significantly less than initial primer concentration $C_{p0}$. In some embodiments, one may choose to derive a precise solution of $f_a$ simply by solving the second order equation of Equation 5.

The $f_a$ value obtained from Equation 7 may be compared with a predetermined threshold template association fraction $f_{a,thr}$. In some embodiments, $f_{a,thr}$ is at least 0.90, 0.91, 0.92, 0.93, 0.94, 0.95, 0.97, 0.98, 0.99, or more. In some embodiments, $f_{a,thr}$ is at from about 0.90 to 0.99, 0.91 to 0.99, 0.92 to 0.99, 0.93 to 0.99, 0.94 to 0.99, 0.95 to 0.99, 0.97 to 0.99, 0.98 to 0.99. If $f_a$ is less than $f_{a,thr}$ the length of the specific segment may be increased by 1 or by a predetermined incremental number and the above calculations is repeated until $f_a$ is above $f_{a,thr}$. The resulting sequence is a candidate primer subjected to further evaluation.

The disclosed method makes a significant improvement over state of art method and/or tool for primer length determination. In the disclosed method the primer length is determined based on the calculated fraction of template being hybridized by the primer at actual annealing or reaction temperature and reaction compositions. Priming efficiency of the primer is proportional to the calculated quantity. In comparison, the state of art primer design methods and tools determine the length of a primer based on primer Tm, which is a nucleic acid quality property that is unrelated to actual reaction temperature. In a thermodynamic calculation (J. SantaLucia Jr. et al. (2004) "The thermodynamics of DNA structural motifs" Annu. Rev. Biophys. Biomol. Struct. 33:415-440), Tm relates to enthalpy and entropy. Tm does not have a monotonic relationship with free energy, which relates to enthalpy, entropy, and temperature, and Tm does not give a prediction for template association fraction $f_a$. The empirical rules of using annealing temperature 5° C. below or 3° C. above primer Tm in the state of art primer design methods does not warrant a sufficient or predictable primer-template binding.

Calculations to evaluate the priming performance of the candidate primer are then performed. In some embodiments, the evaluation includes primer binding to variant alleles, primer 3' end binding stability, and folding impact to primer binding. The hybridization between the reference allele derived candidate primer and a variant allele forms a duplex containing one or more non-Watson-Crick motifs or mismatches that usually lead to the increase of binding free energy and therefore the decrease of template association fraction (see Equation 7). In some embodiments, wherein individual variant alleles are available, binding free energies $\Delta G$ between the candidate primer and all individual available variant alleles are calculated using the above described methods and tools, which include the thermodynamic calculation of nucleic acid duplex containing mismatches. Then calculate the corresponding template association fraction $f_a$ values using Equation 7. Pick the lowest $f_a$ value as the worst case scenario template association fraction $f_{a,min}$ of the candidate primer. In some embodiments, where only a combined variant sequence (e.g. the one from dbSNP) is available, the worst case scenario template association fraction $f_{a,min}$ is calculated against the combined variant sequence using the same method as that for individual variant alleles.

This disclosed method includes a consideration in thermodynamic calculations relating to the effect of enzymes on nucleic acid binding. In common practices of performing PCR using commercially supplied polymerases, the primer annealing temperatures is normally set at manufacture suggest levels. The annealing temperatures for most polymerases are suggested to be 5° C. below primer Tm. However, the annealing temperatures for a new class of polymerases, including Phusion polymerase, and Q5 polymerase (both are offered by NEB, Ipswich, Mass.), are suggested to be 3° C. above primer Tm. This disclosed method takes the effect of polymerase and associated proteins on binding into account of thermodynamic calculations. In some embodiments, the effect of polymerase and associated proteins on binding is counted as an equivalent salt. In an exemplary embodiment, an additional 75 mM is added to the salt concentration in thermodynamic calculation of free energy in a reaction mixture involving Phusion polymerase. In some embodiments, the equivalent salt concentration of polymerase and associated proteins is derived by curve fitting of experimental PCR product yields measured under a matrix of conditions. The variables of conditions include primer specific segment length and annealing temperature. In some embodiments, the experimental PCR is relay PCR. In some embodiments, the effect of polymerase on binding is measured using UV melting curve method (J. SantaLucia (1998) "A unified view of polymer, dumbbell, and oligonucleotide DNA nearest-neighbor thermodynamics" Proc. Natl. Acad. Sci., 95, 1460-1465).

In some embodiments, the calculation for primer 3' end binding stability is carried out with the thermodynamic calculations of binding free energies between the candidate primer and reference as well as variant allele templates. In some embodiments, the primer-template binding free energy with primer 3' end binding the template is calculated using regular nearest neighbor thermodynamics. Name the free energy $\Delta G_{close}$ for primer 3' end close or 3' end binding to corresponding template. Then, calculate the free energy by sequentially removing nearest neighbors from stacking energy terms (see page 418-419 of J. SantaLucia Jr. et al. (2004) "The thermodynamics of DNA structural motifs" Annu. Rev. Biophys. Biomol. Struct. 33:415-440) for a predetermined number of bases starting from 3' end of the primer or until a minimum free energy is reached. In some embodiments, the predetermined number of bases is at least 1, 2, 3, or more. Name the free energy $\Delta G_{open,i}$ for opening at base i. Equation 8 shows the equilibrium reaction between the binding states of primer 3' open at base i and primer 3' closed. $\Delta\Delta G_i$ is the free energy difference between the two binding states. A primer is reactive in an extension reaction only when its 3' end binds to corresponding template. The fraction of a primer-template complex having primer 3' closed is shown in Equation 12, which is derived from binding equilibrium equation (Equations 8 and 9), mass balance equation (Equations 10), and thermodynamic equilibrium constant equation (Equation 11).

$$C_{open,i} \xrightleftharpoons[]{\Delta\Delta G_i = \Delta G_{close} - \Delta G_{open,i}, K_{close,i}} C_{close} \quad \text{Equation 8}$$

$$K_{close,i} = \frac{C_{close}}{C_{open,i}} \quad \text{Equation 9}$$

$$C_c = C_{close} + \sum C_{open,i} = C_{close}\left(1 + \sum \frac{1}{K_{close,i}}\right) \quad \text{Equation 10}$$

$$K_{close,i} = e^{\frac{-\Delta\Delta G_i}{RT}} \quad \text{Equation 11}$$

$$f_{close} = \frac{C_{close}}{C_c} = \frac{1}{1 + \sum \frac{1}{close,i}} = \frac{1}{1 + \sum e^{\frac{\Delta\Delta G_i}{RT}}} \quad \text{Equation 12}$$

In the equations, $C_{open,i}$ and $C_{closed}$ are the equilibrium concentrations of primer-template complex with primer 3' end open at base i and with primer 3' end close, respectively; $C_c$ is primer-template complex concentration expressed in Equation 2; $K_{closed,i}$ is equilibrium constant of the binding states of primer 3' open at base i and primer 3' close; T is annealing temperature; and R is ideal gas constant.

In some embodiments, one or more polymerases involved have 3' to 5' exonuclease activity and one or more mismatches at primer 3' end may be removed during annealing time. The mismatches can be present when the PCR sample contains one or more variant alleles. In some embodiments, where the polymerase used has 3' to 5' exonuclease activity, the primer 3' end binding stability is measured by the fraction of primer-template complex having at most 1, 2, 3, or more nucleotides open at primer 3' end. The exact formulations for the calculation can be derived by those skilled in the art of thermodynamics and by following the teaching of this disclosure. The exact length of allowed opening can be determined experimentally for specific polymerases and specific annealing conditions including annealing time.

The disclosed method makes a significant improvement over state of art methods and/tools for the prediction of primer 3' end binding stability. The disclosed method provides a quantitative prediction for the fraction of primer 3' end binding to its template at actual reaction condition. In comparison, the state of art primer design methods and tools provide empirical scores that penalize primer sequences involving long steams of A and T at 3' end. In this aspect, the state of art methods are qualitative and do not provides a quantitative prediction for the primer performance.

Figure 14:
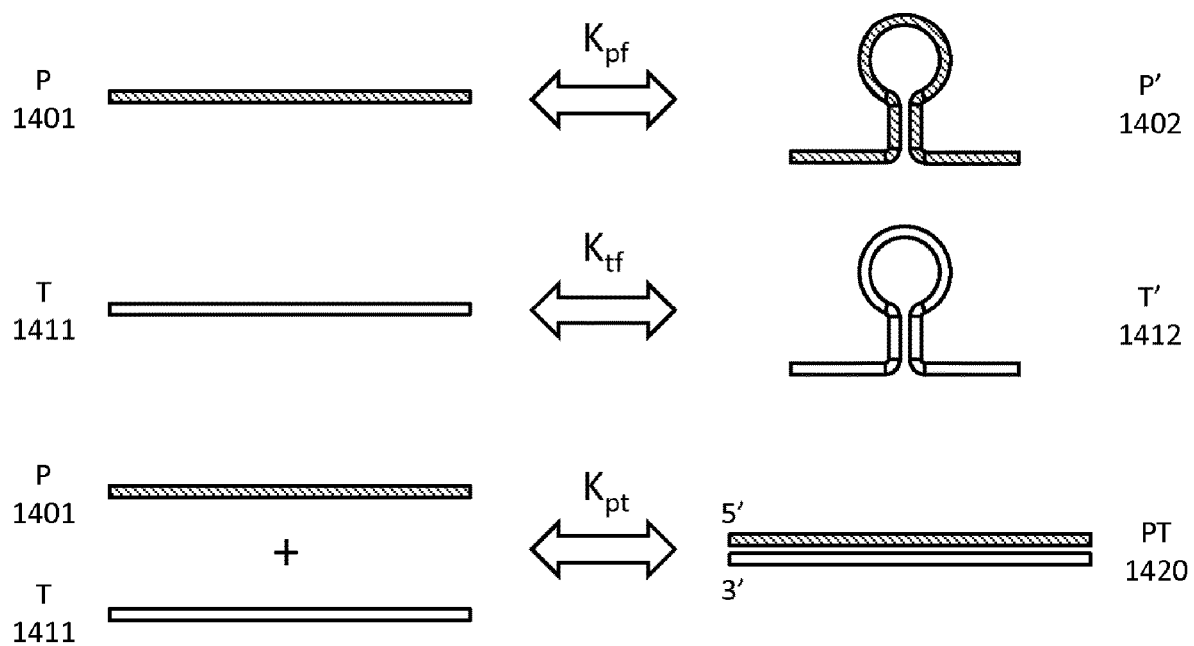
FIG. 14 illustrates simultaneous equilibrium reactions of intramolecular folding and intermolecular hybridization.

FIG. 14 illustrates how primer and template folding impact primer-template binding. The figure shows three parallel reactions including relaxed primer P 1401 turning to a folded structure P' 1402, relaxed template T 1402 turning to a folded structure T' 1412, and primer P 1401 and template T 1402 hybridizing into primer-template complex PT 1420. $K_{pf}$, $K_{bf}$ and $K_{pt}$ are equilibrium constants of folding and hybridization reactions, respectively. At equilibrium, the three reactions are expressed in Equations 13, 14, and 15. Mass balances are expressed in Equations 16 and 17. Thermodynamic equilibrium constants of the three reactions are expressed in Equations 18, 19, and 20.

$$K_{pf} = \frac{C_{p'}}{C_p} \quad \text{Equation 13}$$

$$K_{tf} = \frac{C_{t'}}{C_t} \quad \text{Equation 14}$$

$$K_{pt} = \frac{C_{pt}}{C_p C_t} \quad \text{Equation 15}$$

$$C_{p_0} = C_p + C_{p'} + C_{pt} \quad \text{Equation 16}$$

$$C_{t_0} = C_t + C_{t'} + C_{pt} \quad \text{Equation 17}$$

$$K_{pf} = e^{\frac{-\Delta G_{pf}}{RT}} \quad \text{Equation 18}$$

$$K_{tf} = e^{\frac{-\Delta G_{ft}}{RT}} \quad \text{Equation 19}$$

$$K_{pt} = e^{\frac{-\Delta G_{pt}}{RT}} \quad \text{Equation 20}$$

In the equations, $C_p$, $C_t$, $C_{p'}$ and $C_{t'}$ are the equilibrium concentrations of the primer and template in relaxed and folded states, respectively; $C_{pt}$ is the equilibrium concentrations of the hybridization product; $C_{p0}$ and $C_{t0}$ are the starting concentrations of primer and template, respectively; $\Delta G_{pf}$ is the folding free energy of primer within the specific segment; $\Delta G_{tf}$ is the folding free energy of template within the priming segment; T is annealing temperature; and R is ideal gas constant. In some embodiments, the folding free energies are calculated using nearest neighborhood method (see J. Santa Lucia Jr. et al. (2004) "The thermodynamics of DNA structural motifs" Annu. Rev. Biophys. Biomol. Struct. 33:415-440). In some embodiments the folding free energy is calculated using a computation package such as UNAFold (N. Markham and M. Zuker (2008) UNAFold: software for nucleic acid folding and hybridization. In Keith, J. M., editor, Bioinformatics, Volume II. Structure, Function and Applications, number 453 in Methods in Molecular Biology, chapter 1, pages 3-31. Humana Press, Totowa, N.J. ISBN 978-1-60327-428-9.). In most application cases, starting primer concentration is significantly higher than starting template concentration and the hybridization product concentration is always less than starting template concentration, as shown in Equation 20. Combine Equations 13 through 17 and apply condition Equation 21 we obtain $f_{a,fold}$ of Equation 22 showing the fraction of the template being hybridized by the primer in the presence of competing primer and template folding reactions.

$$C_{p_0} \gg C_{t_0} > C_{pt} \quad \text{Equation 21}$$

$$f_{a,fold} = \frac{C_{pt}}{C_{t_0}} \approx \frac{1}{\frac{(K_{pf}+1)(K_{tf}+1)}{K_{pt}C_{p_0}}+1} \quad \text{Equation 22}$$

The disclosed method makes a significant improvement over state of art methods and/tools for the prediction of folding impact on primer-template binding. The disclosed method provides a quantitative prediction for the fraction of a template being hybridized by a primer in the presence of competing primer and template folding reactions. In comparison, the state of art primer design methods and tools provide empirical scores that penalize primer sequences having stable folding (negative folding free energy). In this aspect, the state of art methods are qualitative and do not provides a quantitative prediction for the primer performance.

In some embodiments, the calculations of Equations 13 through 22 are performed on reference as well as all available variant alleles. Pick the lowest $f_{a,fold}$ value as the worst case scenario template association fraction of the candidate primer. The performance of a primer is predicted by the worst case scenario priming efficiency which is obtained by multiplying the lowest $f_{a,fold}$ of Equation 22 with the lowest $f_{close}$ of Equation 12. In some embodiments, where saving computation time is desired, Equation 22 is applied to reference alleles, Equation 7 and Equation 12 are applied to reference as well as variant alleles. The performance of a primer is predicted by the combination of $f_{a,fold}$, the reference template associate fraction $f_{a,ref}$, the worst case scenario template associate fraction $f_{a,min}$, and the worst case scenario fraction of primer 3' close $f_{close,min}$, is estimated according to Equation 23. This completes the design and performance prediction of a regular primer.

$$f_{prm} = \frac{f_{a,min}}{f_{a,ref}} f_{close,min} f_{a,fold} \quad \text{Equation 23}$$

Repeat the design and performance prediction for the next primer by moving the 3' position of the primer to another predetermined location on the reference primer binding template until the process is completed for all predetermined locations. In some embodiments, the predetermined locations are arranged in a tiling pattern. In some embodiments, the tiling increment is 1, 2, 3, 4, or more nucleotides on a reference primer binding template. In some embodiments, the tiling is formed on both plus and minus strands of the reference primer binding template. In some embodiments, a primer designed at a predetermined location comprises a common segment complementary to the common segment of a predetermined common primer (common primer 1 or common primer 2). In some embodiments, two sets of primers are designed with each set covering all the predetermined locations but one set comprising a common segment complementary to the common segment of common primer 1 and the other set comprising a common segment complementary to the common segment of common primer 2.

As described earlier, an omega primer comprises a 5p arm, a loop, and a 3p arm. The loop sequences are substantially determined by the 3' sections of corresponding common primers and are provided as a part of predetermined parameters. In some embodiments, the 5p arm of the primer functions as an anchor to provide a stable binding to the template sequence while 3p arm checks for specificity of the binding and brings the loop into the extension product. In an exemplary embodiment, the primer design begins from 3p arm. Similar to the design of a regular primer, the 3' position of the primer is fixed at a predetermined location of the reference primer binding template and the initial trail length of the 3p arm is set at a predetermined value. In some embodiments, the predetermined initial trail length is 5, 6, 7, 8, 9 or more. For computation purpose, assume that an omega primer already binds to its template through 5p arm. The proper length of the 3p arm that is just enough to overcome the positive free energy of the loop and to bind to its template with a sufficient binding coefficient is the desired outcome. For convenience, binding of the 3p arm to the template is labeled as the close of the 3p arm. The equilibrium reaction of 3p arm open and closed is shown in Equation 24, which is a first order reaction. Equation 25 shows the free energy of the primer-template complex with 3p arm open. The terminal free energy $\Delta G_{terminal}$ relates to dangle motifs at 5p arm 3' end. $\Delta G_{5pArm,stack}$ is the nearest neighbor stacking free energy of 5p arm. Equation 26 shows the free energy of the primer-template complex with 3p arm close. $\Delta G_{loop}$ is the loop free energy. $\Delta G_{3pArm,stack}$ is the nearest neighbor stacking free energy of 3p arm. Equation 27 shows the fee energy difference between states of 3p arm close and 3p arm open. The free energy calculations for all motifs involved in Equations 25, 26, and 27 are described in detail by SantaLucia (J. SantaLucia Jr. et al. (2004) "The thermodynamics of DNA structural motifs" Annu. Rev. Biophys. Biomol. Struct. 33:415-440). Equation 28 expresses the equilibrium condition of the reaction shown by Equation 24. Equation 29 is a mass balances equation. Equation 30 is the thermodynamic equilibrium constant of the reaction shown by Equations 24.

$$C_{3pArm,open} \xrightleftharpoons[]{\Delta\Delta G = \Delta G_{3pArm,close} - \Delta G_{3pArm,open}} C_{3pArm,close} \quad \text{Equation 24}$$

$$\Delta G_{3pArm,open} = \Delta G_{terminal} + \Delta G_{5pArm,stack} \quad \text{Equation 25}$$

-continued $$\Delta G_{3pArm,close} = \Delta G_{loop} + \Delta G_{3pArm,stack} + \Delta G_{5pArm,stack} \quad \text{Equation 26}$$

$$\Delta\Delta G = \Delta G_{3pArm,close} - \Delta G_{3pArm,open} = \quad \text{Equation 27}$$
$$\Delta G_{loop} + \Delta G_{3pArm,stack} - \Delta G_{terminal}$$

$$K_{3pArm,close} = \frac{C_{3pArm,close}}{C_{3pArm,open}} \quad \text{Equation 28}$$

$$C_{pt} = C_{3pArm,open} + C_{3pArm,close} \quad \text{Equation 29}$$

$$K_{3pArm,close} = e^{\frac{-\Delta\Delta G}{RT}} \quad \text{Equation 30}$$

$$f_{3pArm,close} = \frac{C_{3pArm,close}}{C_{pt}} = \frac{1}{\frac{1}{K_{3pArm,close}} + 1} = \frac{1}{e^{\frac{\Delta\Delta G}{RT}} + 1} \quad \text{Equation 31}$$

In the equations, $C_{pt}$, $C_{3pArm,close}$, and $C_{3pArm,open}$ are the concentrations of primer-template complex, primer-template complex with 3p arm close, and primer-template complex with 3p arm open; T is annealing temperature; and R is ideal gas constant. By combining Equations 28, 29, and 30, Equation 31 is derived which shows the fraction of omega primer having 3p arm binding to the template.

The $f_{3pArm,close}$ value obtained from Equation 31 is then compared with a predetermined threshold value $f_{3pArm,close,thr}$. In some embodiments, $f_{3pArm,close,thr}$ is at least 0.90, 0.91, 0.92, 0.93, 0.94, 0.95, 0.97, 0.98, 0.99, or more. In some embodiments, $f_{a,thr}$ is at from about 0.90 to 0.99, 0.91 to 0.99, 0.92 to 0.99, 0.93 to 0.99, 0.94 to 0.99, 0.95 to 0.99, 0.97 to 0.99, 0.98 to 0.99. If $f_{3pArm,close}$ is less than $f_{3pArm,close,thr}$ increase the 3p arm length by 1 or by a predetermined incremental number and repeat the above calculations until $f_{3pArm,close}$ is above $f_{3pArm,close,thr}$.

Next, the length of 5p arm is determined. For demonstration purpose, a bulge loop (shown in FIG. 1C as 122) is used in our omega primer. In the omega structure of the bulge loop the position of 3' end of 5p arm is set immediately next to 5' end of 3p arm. For computation purpose, the 5p arm is treated as an isolated binding sequence. The length of the 5p arm is derived in a similar to that for regular primer specific segment. The derived 5p arm meets the requirement of producing a predetermined threshold template association fraction. In some embodiments, the threshold value is at least 0.90, 0.91, 0.92, 0.93, 0.94, 0.95, 0.97, 0.98, 0.99, or more. In some embodiments, $f_{a,thr}$ is f at from about 0.90 to 0.99, 0.91 to 0.99, 0.92 to 0.99, 0.93 to 0.99, 0.94 to 0.99, 0.95 to 0.99, 0.97 to 0.99, 0.98 to 0.99. By having derived the sequences of 5p arm and 3p arm plus the predetermined loop sequence, we have a complete candidate omega primer sequence that subjects to further evaluation.

A significant aspect of this disclosure is the design of variant tolerant primers to achieve robust performance on samples from general populations. In an exemplary embodiment, the design is applied to an omega primer. The 3p arm of the variant tolerant omega primer is derived in the same way as described above. The 5p arm of the variant tolerant omega primer is derived by carrying out iterative calculations of Equations 1 through 7 against variant alleles with incremental 5p arm lengths until the threshold template association fraction requirement is met. This forces the length of 5p arm to increase so as to maintain a sufficient binding to the templates even when one or more variants are present in the priming region. In some embodiments, a predetermined maximum length is used in the computation to confine the 5p arm length within a limit. In some embodiments, the predetermined maximum length is at least 40, 50, 60 or more. In some embodiments, the variants included in the calculations are limited to SNP variants. The frequency of SNP variants in general populations is by far the highest among all types of variants. The SNP tolerant primer design can significantly expand the accessible regions for primer placement in genome sequences. In some embodiments, the principle of variant tolerant primers is applied in the design of regular or any other types of primers or probes.

The predictions of omega primers performance are similar to that described above for regular primers. In some embodiments, the prediction of 3' end binding stability of an omega primer is performed using Equations 8 through 12. This produces the worst case scenario fraction of primer 3' close $f_{3pClose,min}$. In some embodiments, the prediction of the folding impact on 5p arm binding to template is performed using Equations 13 through 22. This produces the template association fraction of binding to 5p arm in the presence of folding competition $f_{a,5pArm,fold}$. In some embodiments, the template association fraction of template binding with a whole omega primer $f_{a,omega}$ is calculated using Equations 1 through 7. In some embodiments, the prediction of folding impact on template binding with a whole omega primer $f_{a,omega,fold}$ is performed using Equations 13 through 22.

Figure 15:
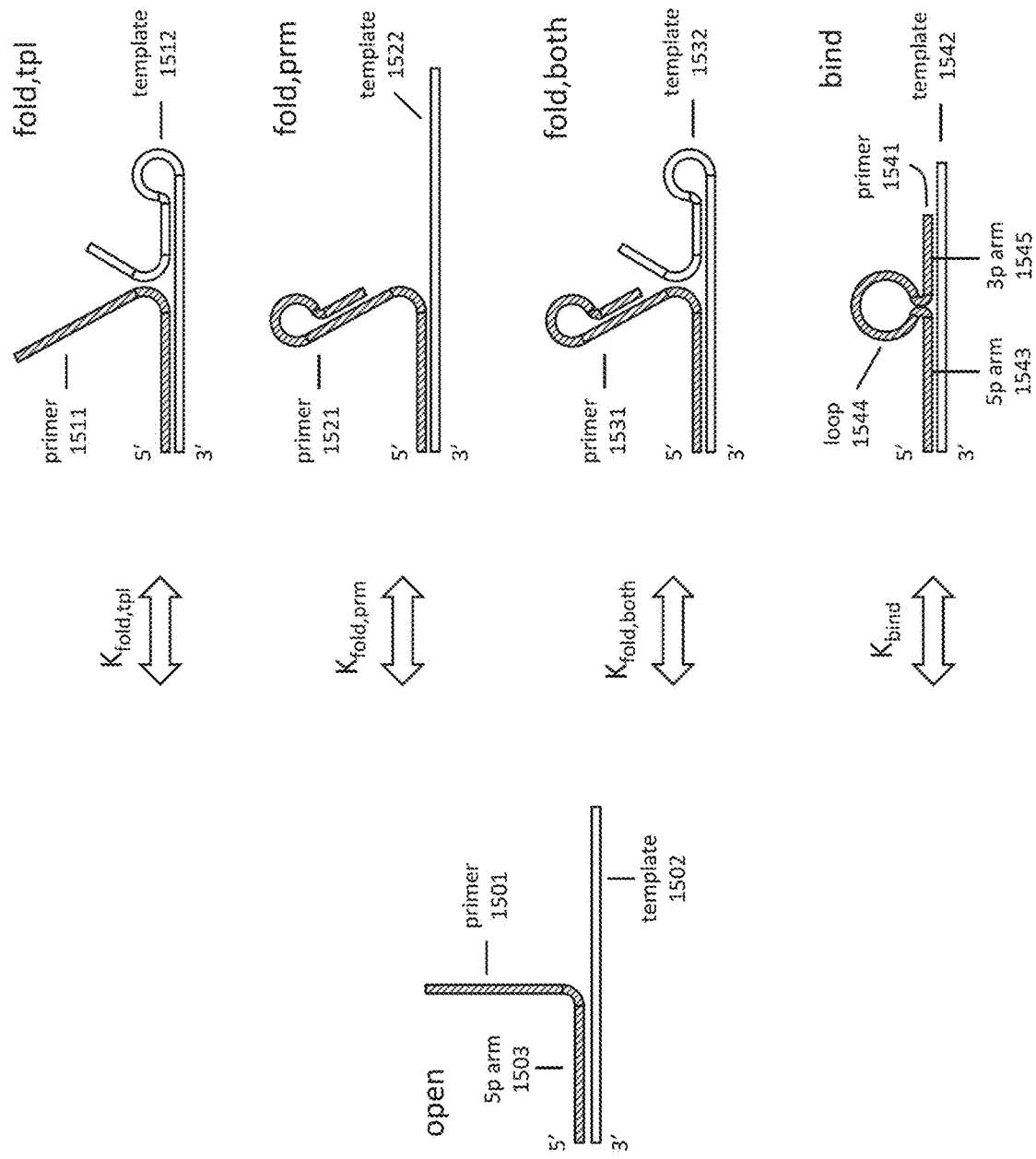
FIG. 15 illustrates simultaneous equilibrium reactions of intra-strand folding and inter-strand hybridization involved in binding between an omega primer and a template.

In some embodiments, additional considerations are given to the prediction of the folding impact on 3p arm binding. FIG. 15 schematically illustrates competitive folding reactions with the 3p arm binding to template. In this exemplary illustration, an omega primer 1501 having its 5p arm 1503 bound to template 1502 is in equilibrium with 4 metastable states of template 1512 being folded, primer 1521 being folded, both primer 1531 and template 1532 being folded, and the desirable form of the 3p arm 1545 binding to template 1542. These reactions are expressed in 4 independent equilibrium equations of Equations 32 through 35. Mass balance is expressed in Equation 36. Thermodynamic equilibrium constants are provided in Equations 37 through 40.

$$K_{fold,tpl} = \frac{C_{fold,tpl}}{C_{open}} \quad \text{Equation 32}$$

$$K_{fold,prm} = \frac{C_{fold,prm}}{C_{open}} \quad \text{Equation 33}$$

$$K_{fold,both} = \frac{C_{fold,both}}{C_{open}} \quad \text{Equation 34}$$

$$K_{bind} = \frac{C_{bind}}{C_{open}} \quad \text{Equation 35}$$

$$C_{pt} = C_{open} + C_{fold,tpl} + C_{fold,prm} + C_{fold,both} + C_{bind} \quad \text{Equation 36}$$

$$K_{fold,tpl} = e^{\frac{-\Delta G_{fold,tpl}}{RT}} \quad \text{Equation 37}$$

$$K_{fold,prm} = e^{\frac{-\Delta G_{fold,prm}}{RT}} \quad \text{Equation 38}$$

$$K_{fold,both} = e^{\frac{-(\Delta G_{fold,tpl}+\Delta G_{fold,prm})}{RT}} \quad \text{Equation 39}$$

$$K_{bind} = e^{\frac{-\Delta\Delta G_{3pArmClose}}{RT}} \quad \text{Equation 40}$$

$$f_{3pArmClose,fold} = \quad \text{Equation 41}$$
$$\frac{C_{bind}}{C_{pt}} = \frac{K_{bind}}{1 + K_{bind} + K_{fold,tpl} + K_{fold,prm} + K_{fold,both}}$$

In the equations, $C_{pt}$, $C_{open}$, $C_{fold,tpl}$, $C_{fold,prm}$, $C_{fold,both}$, and $C_{bind}$ are the concentrations of primer-template complex of all states with the 5p arm binding to template, primer-template complex of open state with primer and template in unfolded states, primer-template complex with template being folded, primer-template complex with primer being folded, primer-template complex with both template and primer being folded, primer-template complex with 3p arm binding to template; $\Delta\Delta G_{3pArmClose}$ is the free energy difference between the states of 3p arm closed and 3p arm open while 5p arm remains bound to template which value is provided in Equation 27; T is annealing temperature; and R is ideal gas constant. Combining Equations 32 through 36, derives Equation 41 which shows the fraction of omega primer having 3p arm binding to the template in the presence of competing primer and template folding reactions.

In an exemplary embodiment, the performance of an omega primer is predicted by the combination of the template associate fraction of the worst case scenario variant template binding with 5p arm $f_{a,5pArm,min}$, the template associate fraction of reference template binding with 5p arm $f_{a,5pArm,ref}$, the worst case scenario fraction of primer 3' close $f_{3pClose,min}$, the template association fraction of reference allele template binding to 5p arm in the presence of folding competition $f_{a,5pArm,fold}$, and the fraction of omega primer having 3p arm binding to the template in the presence of competing primer and template folding reactions $f_{3pArmClose,fold}$. Equation 42 shows an exemplary performance prediction for an omega primer.

$$f_{prm} = \frac{f_{a,5pArm,min}}{f_{a,5pArm,ref}} f_{3pClose,min} f_{a,5pArm,fold} f_{3pArmClose,fold} \quad \text{Equation 42}$$

In some embodiments, the template association fractions relating to 5p arm binding ($f_{a,5pArm,min}$, $f_{a,5pArm,ref}$, and $f_{a,5pArm,fold}$) can be replaced by the corresponding template association fractions relating to whole omega primer binding, depending on the considerations of computation time, calculation precision, specific designed functions of 5p arm, 3p arm, and loop segments, and specific applications. The calculations of the template association fractions relating to whole omega primer binding have been described above.

The design and performance prediction for the next omega primer may be repeated by moving the 3' position of the primer to another predetermined location on the reference primer binding template until the process is completed for all predetermined locations in fashion as describe above for regular primers.

In some embodiments, wherein the fabrication of the specific primers involves PCR amplification, the prediction of the primer performance includes the amplification efficiencies of PCR templates 900, 1000 and 1100 of the primers (regular, omega, and any other types). In some embodiments, template folding in template flanking segments 901, 905, 1001, 1003, 1101, and 1103 are calculated for the impact to priming efficiencies in PCR reactions. In some embodiments, the calculations are carried out using Equations 13 through 22.

Steps 3 to 5 of the primer design process searches for primer off-target locations and provides quantitative predictions for the primer extension efficiencies at the off-target locations. In step 3, all candidate primers are aligned to a reference genome database or any sequence database that substantially represents a complete DNA sequence set involved in the samples on which the candidate primers are going to be applied. In some embodiments, the alignment is carried out by using BLAST or one or more of BLAST derivatives. For convenience, the alignment results are labeled as hits. Remove the one-target hits from the total hits. An on-target hit is the sequence site that a primer is designed to bind. The remaining hits are the off-target hits. Save the alignment locations, aligned part of query sequence, and aligned part of subject sequence for off-target binding coefficient calculation uses. Primer sequences are the query sequences of the alignment and database sequences are the subject sequences. In some embodiments, BLASTN us used. In some embodiments, BLAST is set up in such a way that mismatches and gaps are allowed. In some embodiments, default values of BLAST gapopen, gapextend, penalty, and award are used. In some embodiments, BLAST is set up in such a way that mismatches and gaps are allowed. In some embodiments, a reasonably small BLAST word_size is used to ensure the sensitivity of the off-target search. In some embodiments, BLAST word_size is set at 6, 7, 8, 9, 10, 11, 12, 13, 14, 15 or more. The selection of the word_size is based on the balance of computation time, available computer memory, and the desired sensitivity of the alignment search. BLAST is the most popular and basic alignment tool and its use is familiar by those skilled in the art of bioinformatics.

In some embodiments, wherein an off-target search is performed for omega primers, added alignment operations are desired in addition to the alignment of original whole omega primer sequence. The added alignment captures any off-target sites that may hybridize with the omega primer and form stable loop structures. Being a local alignment tool, BLAST may miss this type of sites due to large gaps involved. In some embodiments, the added alignment is formed by aligning the combined 5p arm and 3p arm sequences against the sequence database of interest. In the alignment result when the aligned part of query sequence includes the junction of 5p arm and 3p arm, insert the corresponding loop sequence into the junction of the aligned part of query sequence to produce a restored query sequence and insert a gap of the same loop length into the junction corresponding site of the aligned part of subject sequence to produce an aligned subject sequence. Then compile the alignment results by removing redundant alignment hits between the results of whole omega primer alignment and combined 5p arm and 3p arm sequence alignment. In some embodiments, the added alignment is performed by doing pairwise alignments using a global alignment tool on the sequence pairs of whole omega primer sequences and expanded regions of corresponding BLAST hits. In some embodiments, the global alignment tool is written based on Needleman-Wunsch algorithm (S. Needleman el al. (1970) "A general method applicable to the search for similarities in the amino acid sequence of two proteins" Journal of Molecular Biology 48, 443-53). The alignment result would already have the proper gaps.

Step 4 of the primer design is to construct primer/off-target binding pair sequences ready for the binding coefficient calculation. The paired sequences are constructed by expanding the aligned part of query as well as subject sequences at both ends by a predetermined number of nucleotides. In some embodiments, the predetermined number is 0, 1, 2, 3 or more. The purpose of expanding the aligned parts is to produce overhangs at both ends of the binding pair sequences so that the following binding calculations can be done more accurately by including the overhang stacking energies (J. SantaLucia Jr. et al. (2004) "The thermodynamics of DNA structural motifs" Annu. Rev. Biophys. Biomol. Struct. 33:415-440).

Step 5 of the primer design is to calculate the primer/off-target binding properties. The binding free energies between primers and off-target sequences are calculated using the same methods described above for primer binding to on-target template. From the free energies we obtain the binding coefficient on off-target sequences using Equations 1 through 7 at specific primer annealing condition. Another important off-target binding property is the distance between the end of the binding regions and 3' end of the primers also known as the distance overhang length. When the overhang length is below a threshold length, the off-target primer is considered extendable. In some embodiments, the threshold length is determined by the polymerase used. In some embodiments, when the polymerase does not have 3' to 5' exonuclease activity, the threshold length is 0. In some embodiments, when the polymerase has 3' to 5' exonuclease activity, the threshold length is at least 0, 1, 2, 3 nucleotides, or more. In some embodiments, the full set of primer/off-target binding properties, including location, binding coefficient, and extendibility, are saved for further use when the binding coefficient exceeds a threshold binding coefficient value. In some embodiments, the threshold binding coefficient value for an extendable off-target binding is 0.05, 0.01, 0.005, or less. In some embodiments, the threshold binding coefficient value for a non-extendable off-target binding is 0.75, 0.5, 0.25, 0.1 or less. The threshold binding coefficient values are determined by the required primer specificity, computation time, computer memory size, and computer storage size.

Step 6 of the primer design is to calculate cross-hybridization binding between candidate specific primers and common primers. In some embodiments, the common primers are aligned against all candidate primers. Then the alignment results are used to calculate binding coefficients in the same way as described in Step 5. In some embodiments, the cross-hybridization free energies are calculated using a computation package such as UNAFold (N. Markham and M. Zuker (2008) UNAFold: software for nucleic acid folding and hybridization. In Keith, J. M., editor, Bioinformatics, Volume II. Structure, Function and Applications, number 453 in Methods in Molecular Biology, chapter 1, pages 3-31. Humana Press, Totowa, N.J. ISBN 978-1-60327-428-9). For most applications, the concentration of each specific primer is significantly less than that of the common primer and the binding coefficient is the fraction of a specific primer binding hybridized by a common primer. The primer extendibility for both specific primers and for common primers should be examined. If an extendible primer is found, further examine if the extension product can be amplified by one or both common primers. An extension product is amplifiable if it is produced by a common primer extending from the specific segment of a regular primer or from 3p arm segment of an omega primer. Record the binding coefficient, extendibility, and amplifiability of a candidate primer when the binding coefficient exceeds a threshold binding coefficient value. In some embodiments, the threshold binding coefficient value for a non-extendable cross-hybridization binding is 0.25, 0.2, 0.1 or less. In some embodiments, the threshold binding coefficient value for an extendable but not amplifiable cross-hybridization binding is 0.2, 0.1, 0.05, or less. In some embodiments, the threshold binding coefficient value for an extendable and amplifiable cross-hybridization binding is $10^{-5}$, $10^{-6}$, $10^{-7}$, $10^{-8}$, or less. The threshold binding coefficient values for non-amplifiable cross-hybridization binding are determined by the considerations of keeping a reasonably high fraction of the specific primer available for specific priming use. The threshold binding coefficient value for amplifiable cross-hybridization binding is determined by the concentration ratio between specific primer and relay PCR template. The objective is to keep the level of primer-dimer product below the level of template amplification product. As an illustrative example, assuming the template concentration is 1 fM and the specific primer concentration is 10 pM; a binding coefficient of $10^{-5}$ for an amplifiable cross-hybridization binding would produce about 0.1 fM of primer-primer extension product that would be amplified in parallel with the template. At end, about 10% of the PCR product would be primer-primer dimer. The calculation on the cross-hybridization binding among specific primers is performed in Step 9 of the computation process when individual candidate specific primers are actually picked.

Step 7 of the primer design is to calculate the scores of all candidate primers. In some embodiments, in addition to the quantitatively calculated priming efficiency derived in Step 2, we use several quality scores to guide the final primer selection from the candidate primer pool. In an exemplary embodiment, the quality scores are formulated to favor GC content of the primer between 0.4 and 0.6, to discourage primer length beyond 90, to favor high ratio of primer lengths obtained on reference allele versus on the worst case scenario variant allele, to discourage off-target binding, and to discourage cross-hybridization binding between specific primers and common primers. The calculations of the previous steps have already generated the required parameters needed for the score calculations. The already calculated parameters include the primer length, primer length against reference allele template, the primer length against worst case scenario variant allele template, the binding coefficients for the extendable and the non-extendable off-target binding, and binding coefficients for the non-extendable, extendable but not amplifiable, and amplifiable cross-hybridization binding between candidate specific primers and common primers. Score formulations using linear, non-linear, proportional, reverse-proportional, and certain types of distribution curves which are familiar to those skilled in the art of process control, automation, and conventional PCR primer design. In an exemplary embodiment, all scores have a maximum value of 1 and minimum value of 0, 1 being the best and 0 being the worst. Combine all individual scores into a single score according to Equation 43 to represent the overall quality of the primer.

$$S_{prm} = \Pi S_i^{w_i}$$
Equation 43

In the equation, $S_i$ is an individual score, including that of GC content, primer length, primer length ratio of reference allele versus the worst case scenario variant allele, off-target binding, and cross-hybridization binding between specific primers and common primers. In the equation, $w_i$ is the weighing factor of score $S_i$. The weighing factor is an empirically determined number that is used to adjust the relative importance of an individual score in the determination of overall quality score. The weighing factor usually has a minimum value of 0.

Step 8 of the primer design is to build a list of candidate capture regions. The list comprises start and end locations of the capture regions with each candidate capture region having specific primer 1 and specific primer 2. The candidate capture regions serve the purpose of providing full coverage of the requested target regions with abundant combinations of specific primer 1 and specific primer 2 so that final selections of the capture regions can be made by picking the best possible combinations of specific primer 1 and specific primer 2. "Candidate capture region" and "capture region" are used interchangeably. In some embodiments, the capture regions are arranged in a tiling pattern. In some embodiments, the lengths of the capture regions are predetermined. In some embodiments, the predetermined region lengths are decided based on applications. In an exemplary embodiment, the captured sequences are used in high-throughput sequencing. The lengths of the capture regions are determined based on sequencing read length. The sequencing read length is the number of nucleotides that a sequencing instrument reports from a single reading pass. As an illustrative example, a sequencing run includes two passes with each pass having a read length of 150 nt (nucleotide). The two passes read target sequences from two opposite ends. The total sequenced length would be 300 nt. Then, for the purpose of reading the whole capture region and yet having some overlapping between two reading passes, 280 nucleotide can be selected as the maximum capture region length. It is useful to maintain some flexibility on the region length for choosing the best possible specific primers. 140 nucleotides was selected as the minimum capture region length. The ability to handle situations of a long repeat masked section exceeding the maximum capture region length is also useful. A repeat masked sequence can often have a very large number of occurrences in a genome and is often masked out from primer design. In order to fully cover all requested target regions, the maximum capture region length is expanded when the tiling process runs into a repeat masked region. For illustrative purpose, we set the expanded maximum capture region length at 600.

In some embodiments, the tiling process for a target starts by picking up the left most (or the lowest location) candidate specific primer 1 of plus strand and then pick a candidate specific primer 2 of minus strand located a minimum capture region length upstream. Make sure at least a portion of requested target region is between the two specific primers. A candidate amplicon will be produced from PCR amplification of the candidate captured sequence. The quality score of the candidate amplicon is the product of the quality scores of the two specific primers. In some embodiments, other quality scores are calculated including but not limited to GC content, folding free energy, and the length of the candidate capture region. The formulation of the scores may be derived by following the teaching of Step 7 above. The overall quality score of the amplicon is calculated the same as Equation 43. Add the start and end locations of the capture regions, the information of specific primer 1, the information of specific primer 2 and the amplicon score to the list of the candidate capture regions. Repeat the above process with an increment of capture region length until the maximum capture region length is reached. In some embodiments, the increment is 1, 2, 3, 4, or more. Then start from the next left most candidate specific primer 1 of plus strand and repeat the above process until the tiling reaches to the right most available candidate specific primer. In some embodiment, additional rounds of tiling are performed by starting with the left most candidate specific primer 2 of plus strand, specific primer 1 of minus strand, and specific primer 2 of minus strand, each matched by the other specific primer of the opposite strand.

Step 9 of the primer design is to select amplicon sequences to cover all requested target sequences. In this section of the computation, final selections of amplicons including corresponding specific primers are made among all available candidate amplicons on the list of the candidate capture regions. In some embodiments, final amplicons are selected in a tiling fashion. In some embodiments, the tiling process is applied to one target sequence at a time.

In some embodiment, the tiling selection for a target sequence starts from the group of candidate amplicons that cover the starting position of the target sequence. Among the group, calculate cross-hybridization binding between the paired candidate specific primers and each candidate specific primer to itself in the same way as described in Step 6 above. Calculate the scores for the cross-hybridization binding in the same way as described in Step 7 above.

Next, predict the capture of off-target sequences by the candidate specific primers. This is done by looking up at the primer/off-target binding property data of Step 5 and deciding if any measurable off-target sequences can be captured by the candidate specific primers. When two specific primers both have extendable off-target binding sites on the same contig sequence, have 3' ends facing each other, are located in opposite strands, and are sufficiently close to each other, they would produce an off-target sequence. The considerations include a single specific primer having two or more off-target binding sites. In some embodiments, the off-target capture is considered only when the distance between the off-target binding sites is below a threshold distance. In some embodiments, the threshold distance is at most 100,000, 10,000, 1000, or less. The relative concentration of the off-target product is predicted from the product of the binding coefficients of the two off-target binding sites. An off-target score for the candidate amplicon (which is associated with the candidate specific primers) is calculated based on the relative concentration of the off-target product. In some embodiments, the off-target score is formulated as inversely proportional to the relative concentration of the off-target product, with the score ranging from 0 to 1.

Revise the quality score of the corresponding amplicon by multiplying the original quality score by the cross-hybridization binding score and the off-target score. Then, pick the amplicon that has the highest quality score as the first tile. If the selected amplicon covers the end position of the target sequence, the selection is complete for the target sequence. If the selected amplicon does not cover the end position of the target sequence, proceed to the next tile.

In a preferred embodiment, adjacent tiles overlap for certain length at the junction. In some embodiments, the overlap length is at least 1, 2, 5, 10, 15 or more nucleotides. In some embodiments, a minimum overlap length and a maximum overlap length are predefined as a part of input parameters. In some embodiments, the minimum overlap length is at least 1, 2, 5 or more nucleotides. In some embodiments, the maximum overlap length is at least 10, 20, 30, or more nucleotides. In some embodiments, in order to avoid the interference of capture reactions (Cycle 1 and Cycle 2 of FIGS. 3, 4A, 4B, and 5) between adjacent tiles, relay PCR reactions of adjacent tiles are performed in separate PCR tubes. In some embodiments, two PCR tubes are used for the capture and amplification of a complete set of target sequences with each tube containing the specific primers for every other member of the tiles. Save the primer information of the first tile amplicon to tube 1 primer list. The second tile is selected from the group of candidate amplicons that have capture region start position in the range of the first tile capture region end position minus the maximum overlap length and minus the minimum overlap length. From the group, pick the second tile amplicon in the same way as describe above for the first tile. Save the primer information of the second tile amplicon to tube 2 primer list. If the selected amplicon covers the end position of the target sequence, the selection is complete for the target sequence. If the selected amplicon does not cover the end position of the target sequence, proceed to the next tile and until the end of the target sequence is reached.

When primers are already present in tube 1 or 2, the pre-existing primers need to be included in the calculation of specific primer cross-hybridization binding and off-target capture. For example, if the above process is continued for the third tile, the newly selected primers would be placed in tube 1. The calculations for both specific primer cross-hybridization binding and for off-target capture would include the binding between the paired new specific primers, each new specific primer to itself, and each new specific primer to each one of the primers already in tube 1.

In some embodiments, special considerations are given to tile selections on target sequences containing long homologous sections. As described above, the long homologous sections have been identified in Step 1 and the information is available in a target data table. In some embodiments, amplicons are selected based on one copy of the homologous sections and the corresponding specific primers are used for all the homologous sections. This avoids the potential problems of duplicating and/or conflicting primer selections from essentially the same target sequences but at different locations.

Obviously many modifications and variations of the disclosed computation method are possible in the light of the above teachings. For example, in some embodiments, low quality primers are removed along the way so as to reduce computation times for later steps.

Applications

In addition to the aforementioned target enrichment for massive parallel sequencing use, the present invention may be advantageously used in various other applications. In some embodiments, omega primers in combination with Relay PCR are advantageously used in real-time PCR. A pair of specific primers and a pair of common primers are used in each reaction. During a thermal cycling process, in the first two cycles specific Omega primers pick up a target section with high specificity and efficiency. In the remaining cycles common primers take over for the amplification of the target. The advantage of this approach is that one pair of well characterized common primers are used in amplification cycles no matter what target sequences are. Measurement dependence over target sequence variation is expected to be reduced over conventional real-time PCR in which specific primers are responsible for all amplification cycles. Amplification yield differences due to different specific primer designs are exponentially amplified in the conventional method. By using relay PCR, amplification yield differences due to different specific primer designs are eliminated. In some embodiments, regular specific primers in combination with Relay PCR are used in real-time PCR.

In some embodiments, relay PCR is used to prepare samples for array detection uses. A plurality of specific primers and a pair of common primers are used in each relay PCR reaction. In some embodiments, at least one common primer is attached with a fluorescence dye, including but not limited to Cy3, Cy5, Alexa 3, Alexa 5, FTIC, and FAM (add more here). In some embodiments, at least one common primer is attached with a conjugation ligand, including but not limited to biotin, NHS, NH2, and CHO. The fluorescence dyes and the ligands are hereafter called labels. One or more labels may be attached to one or more nucleotides of a primer molecule. A label attached primer is called labeled primer. In some embodiments, a pair of common primers consists of one unlabeled primer and one labeled primer. In some embodiments, the concentration of the labeled primer is higher than that of the unlabeled primer. The molar concentration ratio of the labeled and unlabeled primers is at least 1, 2, 5, 10, or greater. In some embodiments, two rounds of PCR reactions are used to produce labeled target samples. In the first round, a relay PCR is performed. A plurality of specific primers and one pair of unlabeled common primers are used. The first round PCR product is optionally purified to remove residual primers and enzymes and to retain the double stranded PCR product. The second round is a single-strand PCR reaction, involving one labeled common primer and an aliquot of first round PCR product or purified first round PCR product. In some embodiments, the aliquot is at least 1/1000, 1/500, 1/200, 1/100, 1/50, 1/20, 1/10 or more of the total volume of the first round PCR product.

In some embodiments, the composition includes one or more target specific primer pairs that can amplify a short tandem repeat, single nucleotide polymorphism, gene, exon, coding region, exome, or portion thereof. In some embodiments, templates are cDNAs that are synthesized from RNA samples.

Thus, in some embodiments, an oligonucleotide primer comprising a 3p arm having a 3' end and a 5' end, a loop section and a 5p arm having a 3' end and a 5' end, wherein the 5p arm hybridizes to a DNA template and wherein the 3p arm hybridizes to the DNA template and provides sequence specificity for polymerase extension and wherein the loop section is located between the 5p arm and the 3p arm and does not bind the DNA template is provided. In some embodiments, the DNA template is substantially complementary to the 5p arm and the 3p arm. In some embodiments, the 5p arm is from 10 to 100 nucleotides in length, such as 25 to 60 nucleotides, and/or the 3p arm is from 6 to 60 nucleotides in length, such as from ten to 20 nucleotides, and/or the loop section is from 12 to 50 nucleotides in length, such as from 15 to 40 nucleotides. In some embodiments, the 5' end of the 3p arm and the 3' end of the 5p arm are adjacent each other when bound to the DNA template. In some embodiments, the 5p arm has higher binding energy than the 3p arm when hybridized to the DNA template (such as two or three times higher). In some embodiments, the primer comprises a bulge loop, hairpin loop and/or internal loop.

In some embodiments, this disclosure provides a hybridization structure for assay use comprising a probe and a target wherein the hybridization structure has one or more single stranded loops and two or more duplex segments wherein each loop is located between the duplex segments. In some embodiments, the single stranded loop is in the probe and comprises one or more non-nucleotide moieties. In some embodiments, the probe comprises a spacer. In some embodiments, the hybridization structure is used for polymerase extension. In some embodiments, the hybridization structure is used for hybridization detection. In some embodiments, the loop contains 12 to 50 nucleotides.

In some embodiments, methods for amplifying a target nucleic acid are provided. In some embodiments, the method comprises providing a first specific primer, a first common primer, a second common primer, a flanked target fragment, a polymerase and nucleotides; performing a target selection comprising one cycle of a first thermocycling routine comprising an denaturation step, annealing step and an extension step; and, performing amplification comprising two or more cycles of a second thermocycling routine comprising an denaturation step, annealing step and an extension step thereby amplifying the target nucleic acid. In some embodiments, the method comprises providing a first specific primer, a second specific primer, a first common primer, a second common primer, a target nucleic acid, a polymerase and nucleotides; performing a target selection comprising two cycles of a first thermocycling routine comprising an denaturation step, annealing step and an extension step; and, performing amplification comprising two or more cycles of a second thermocycling routine comprising an denaturation step, annealing step and an extension step thereby amplifying the target nucleic acid. In some embodiments of these methods, the first specific primer has a 3' end and a 5' end wherein the 3' end contains a first sequence specific segment and the 5' end contains a first common segment, and/or the second specific primer has a 3' end and a 5' end wherein the 3' end contains a second sequence specific segment and the 5' end contains a second common segment, and/or the concentration of the first and second specific primers is 500 fold less than that of the first and second common primer, and/or the concentration of the first and second specific primers is from about 0.0001 nM to about 5 nM, and/or the concentration of the first and second common primers is from about 200 nM to about 5000 nM, and/or the concentration of the first and second specific primers is less than 1 nM, and/or the concentration of the first and second common primers is more than 200 nM, and/or the first specific primer is an omega primer and wherein the second specific primer is an omega primer, and/or the annealing time for the first thermocycling routine is from about 30 minute to about 4 hours, and/or the annealing temperature for the first thermocycling routine is from about 60° C. to about 75° C., and/or the annealing temperature for the first thermocycling routine is from about 60° C. to about 72° C., and/or the annealing temperature for the first thermocycling routine is from about 65° C. to about 72° C., and/or the second thermocycling routine has from 10-50 cycles such as 20-40 cycles, and/or the annealing temperature is within 10° C. of the peak polymerase activity of the polymerase, and/or the polymerase is a polymerase without strand-displacement activity and 5' to 3' nuclease activity, and/or the polymerase is selected from the group consisting of Phusion Hot Start Flex DNA polymerase and Q5® Hot Start High-Fidelity DNA Polymerase.

In some embodiments, methods for amplifying two or more different target nucleic acids are provided. In some embodiments, such methods comprise providing a set of specific primer pairs wherein each pair comprises a first specific primer and a second specific primer and is designed for a specific target nucleic acid, a first common primer, a second common primer and a set of target nucleic acids, a polymerase and nucleotides; performing two cycles of a first thermocycling routine comprising an denaturation step, annealing step and an extension step; and performing two or more cycles of a second thermocycling routine comprising an denaturation step, annealing step and an extension step thereby amplifying the target nucleic acid. In some such embodiments, the concentration of the first and second specific primers is 500 fold less than that of the first and second common primer, and/or the concentration of the first and second specific primers is from about 0.0001 nM to about 5 nM, and/or the concentration of the first and second common primers is from about 200 nM to about 5000 nM, and/or the concentration of the first and second specific primers is less than 1 nM, and/or the concentration of the first and second common primers is more than 500 nM, and/or the annealing time for the first thermocycling routine is from about 30 minute to about 4 hours, and/or the first and second specific primers are an omega primers or the first and second specific primers are regular specific primers.

In some embodiments, methods for purifying PCR products are provided. In some embodiments, the methods comprise adding, to a mixture of PCR reaction components comprising target sequences, a first common primer and a second common primer, DNA fragments, polymerase, PCR buffer solution wherein the target sequences are flanked with priming segments that are either identical or complementary to the first common primer and the second common primer, the fragments do not contain priming segments, and the second common primer comprises a priming segment, a modifier segment and a tag segment; probe grafted beads wherein the probe has a sequence that is substantially complementary to that of tag segment and facilitates the capture of the PCR product by the beads through hybridization. In some embodiments of such methods, the modifier segment is selected from the group consisting of one or more C3 alkyl spacers, one or more ethylene glycol spacers, one or more photo-cleavable spacers, one or more 1',2'-dideoxyribose, one or more deoxyuridines or combinations thereof. In some embodiments, the tag segment comprises at least one binding moiety. In some embodiments, the binding moiety may be biotin. In some embodiments, the tag segment may comprise an oligonucleotide and a binding moiety. In some embodiments, the binding moiety may be attached to the 5' end of the tag segment oligonucleotide.

In some embodiments, methods for generating surface clusters are provided. In some embodiments, such methods may comprise amplifying a target sequence with a first common primer and a second common primer wherein the first common primer comprising a priming segment and the second common primer comprising a priming segment, modifier segment and tag segment to produce a PCR product containing a single-stranded tag wherein the PCR product comprises the first strand and the second strand wherein the second strand is connected to the single-stranded tag; providing a substrate wherein the substrate comprises a probe, a first surface primer and a second surface primer; applying the PCR product and a guide to the substrate thereby hybridizing the PCR product, the guide and the probe to produce a PCR product/guide/probe complex on the substrate surface; ligating the PCR product and the probe thereby linking the PCR product; washing the substrate thereby removing the first strand of the PCR product; and, extending the first surface primer and the second surface primer thereby forming surface clusters. In some such embodiments, a probe, a first surface primer, and a second surface primer are attached to the substrate. In some embodiments, the probe, a first surface primer, and a second surface prime further comprise a spacer through which the probe, the first surface primer, and the second surface prime may be connected to the substrate surface.

In some embodiments of the methods described herein, the common primer may have a tail segment and a common segment; and/or the specific primer has a specific segment and a common segment. In some embodiments, the primer described herein may have a common segment and a specific segment, wherein the specific segment is comprised of the 3p arm and 5p arm and wherein the loop is comprised of the common segment.

In some embodiments, methods for designing a PCR primer are provided. In some embodiments, such methods may comprise determining a primer length to produce a sufficient template association coefficient; determining primer 3' end binding coefficient; determining template association coefficient in the presence of folding effect; and, determining priming efficiency by combining association coefficient of variant alleles.

A better understanding of the present invention and of its many advantages will be had from the following examples, given by way of illustration.

EXAMPLES

Example I

Comparison of Regular and Relay PCR

Lambda DNA (from NEB, Ipswich, Mass.) was used as template, two regular specific primers and two common primers were used. Phusion Hot Start Flex polymerase Master Mix (from NEB, Ipswich, Mass.) was used. The compositions of individual reaction mixtures are listed below. The reaction in tube 1 is a regular PCR. The reactions in tube 2 and tube 3 are relay PCR of utilizing different specific primer concentrations.

TABLE 1

Reaction mixture compositions

| | Units | Tube 1 | Tube 2 | Tube 3 |
|---|---|---|---|---|
| Specific Primer (lambdaPrm1, lambdaPrm2) | nM (per primer) | 500 | 5 | 0.5 |
| Common primer (comPrm1, comPrm2) | nM (per primer) | | 500 | 500 |
| Template-LambdaDNA | fM | 10 | 10 | 10 |
| Phusion Hot Start Flex 2X Master Mix | X | 1 | 1 | 1 |
| Total volume | µL | 25 | 25 | 25 |

Thermo cycling reactions were performed on Thermal Cycler DNA Engine Tetrad (from Bio-Rad, Hercules, Calif.). Regular PCR for tube 1 was conducted using temperature program is shown below.

TABLE 2

PCR temperature program

| | Step | Temp (° C.) | Time |
|---|---|---|---|
| Activation | 1 | 98 | 30 sec |
| Denaturatoin | 2 | 98 | 15 sec |
| Annealing | 3 | 60 | 30 sec |
| Extension | 4 | 72 | 30 sec |
| GOTO 2 for 1 time | 5 | | |
| Denaturatoin | 6 | 98 | 15 sec |
| Extension | 7 | 72 | 30 sec |
| GOTO 6 for 25 times | 8 | | |
| Extension | 9 | 72 | 10 min |
| Hold | 10 | 4 | Forever |

Relay PCRs for tubes 2 and 3 were conducted using the temperature program shown below.

TABLE 3

Relay PCR temperature program

| | Step | Temp (° C.) | Time |
|---|---|---|---|
| Activation | 1 | 98 | 30 sec |
| Denaturatoin | 2 | 98 | 15 sec |
| Annealing specific primers | 3 | 60 | 1 hr |
| Extension | 4 | 72 | 30 sec |
| GOTO 2 for 1 time | 5 | | |
| Denaturatoin | 6 | 98 | 15 sec |
| Initial common primer anealing | 7 | 60 | 30 sec |
| Extension | 8 | 72 | 30 sec |

TABLE 3-continued

Relay PCR temperature program

| | Step | Temp (° C.) | Time |
|---|---|---|---|
| GOTO 6 for 1 time | 9 | | |
| Denaturatoin | 10 | 98 | 15 sec |
| Extension | 11 | 72 | 30 sec |
| GOTO 10 for 25 times | 12 | | |
| Extension | 13 | 72 | 10 min |
| Hold | 14 | 4 | Forever |

Specific and common primer sequences are list below. All oligonucleotide sequences of this and all following experiments were provided by LC Sciences, Houston, Tex. Unless explicitly described, all oligonucleotide sequences are synthesized using conventional synthesis method on CPG (controlled pore glass) substrates (L. J. McBride et al. (1983) "An investigation of several deoxynucleoside phosphoramidites useful for synthesizing deoxyoligonucleotides" Tetrahedron Letters, 24:245 248).

TABLE 4

Primer sequence list

| Primer Name | Primer Sequence 5' to 3' |
|---|---|
| lambdaPrm1 | GTTCAGAGTTCTACAGTCCGACGATCATACTCCCGA CAATCCCCAC SEQ ID NO: 1 |
| lambdaPrm2 | CCTTGGCACCCGAGAATTCCAGTATGTCGCAGGTAA AAAGTGC SEQ ID NO: 2 |
| comPrm1 | AATGATACGGCGACCACCGAGATCTACACGTTCAGA GTTCTACAGTCCGA SEQ ID NO: 3 |
| comPrm2 | CAAGCAGAAGACGGCATACGAGATACATCGGTGACT GGAGTTCCTTGGCACCCGAGAATTCCA SEQ ID NO: 4 |

Figure 16:
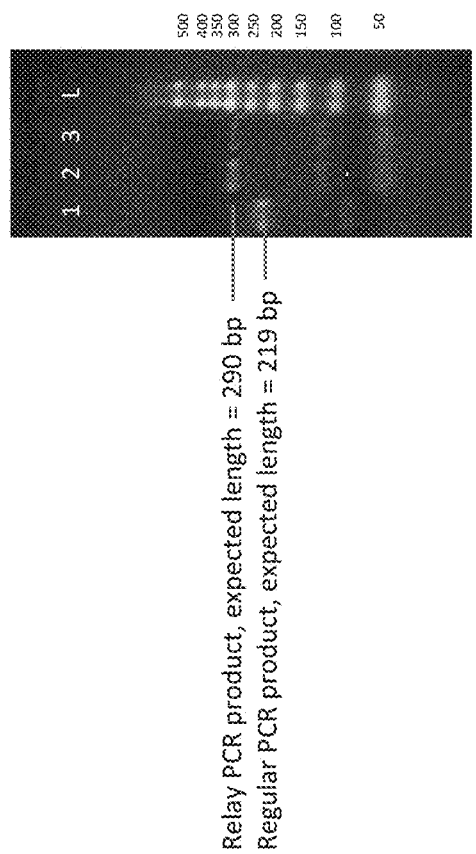
FIG. 16 shows agarose gel electrophoresis images of example regular PCR and relay PCR products on a Lambda DNA sample.

PCR products were analyzed using 3% agarose gel electrophoresis. The agarose gel was prepared by dissolving 1.2 g of agarose in 40 ml 1×TAE and casted into a gel slab according to the instruction of agarose manufacture (Grand Island, N.Y.). A 12×7-mm comb was used to create sample loading wells. For gel loading, 1 μL PCR product solution from each PCR product tube (of 25 μL) was mixed with 1 μL 6× Blue Gel Loading buffer and 4 μL TAE in a PCR tube. The mixtures were thoroughly mixed, spun down, and loaded into the gel loading wells. Electrophoresis was conducted at 70V for 1 hr 20 min. The gel slab was stained by using SYBR Gold by following manufacture instruction (Grand Island, N.Y.). FIG. 16 shows an agarose gel electrophoresis image of the experiment. Lanes 1 through 3 are the products in tube 1 through 3. Lane L is 50 bp ladder run. In all three tubes, PCR products of expected sizes were obtained.

The regular PCR in tube 1 included two specific primers and the expected product size is 219 bp. In this reaction, a regular concentration of 500 nM was used for both primers. An annealing time of 30 sec was sufficient to have produced the expected product and at expected amount as shown in lane 1 of FIG. 16. The annealing temperature of 60° C. in the first two cycles was determined by the Tms of target specific sections of the specific primers. In the remaining cycles, combined annealing-extension steps at 72° C. were used. The temperature was determined by the Tms of the whole specific primers.

The relay PCRs in tubes 2 and 3 involved two specific primers and two common primers. The expected product size is 290 bp. Low concentrations of 5 nM and 0.5 nM were used for specific primers in tube 2 and tube 3, respectively. A long extended annealing time of 1 hr was used in the first two cycles to allow hybridizations between the low concentration specific primers and corresponding templates. The annealing temperature of 60° C. in the first two cycles was determined by the Tms of target specific sections of the specific primers. Cycles 3 and 4 are designed to add common primer flanks to the cycle 1 and cycle 2 produced target sequences. The annealing temperature of 60° C. in cycles 3 and 4 was determined by the Tms of common segments of the common primers. In the remaining cycles, combined annealing-extension steps at 72° C. were used. The temperature was determined by the Tms of the whole common primers. In this reaction, a regular concentration of 500 nM was used for the common primers. Short annealing time of 30 sec was used for the amplification cycles from cycle 3 till the last cycle. Expected products at expected amount were observed in the gel image as shown in lanes 2 and 3 of FIG. 14.

Control experiments were performed. The first control experiment involves the two common primers (comPrm1 and comPrm2) at 500 nM each, lambda DNA at 10 fM, and Phusion Hot Start Flex polymerase Master Mix (from NEB, Ipswich, Mass.). The second control experiment involves the two specific primers (lambdaPrm1 and lambdaPrm2) at 50 nM each, the two common primers (comPrm1 and comPrm2) at 500 nM each, without lambda DNA, and Phusion Hot Start Flex polymerase Master Mix (from NEB, Ipswich, Mass.). Both control experiments were carried out using the relay PCR temperature program shown above. No product was observed in either reaction.

Example II

Relay PCR Using Omega Primer for Amplification of Human Genomic DNA

Human DNA was used as template, two regular specific primers and two common primers were used. Phusion Hot Start Flex polymerase Master Mix (from NEB, Ipswich, Mass.) was used. Six pairs of specific primers were used to individually amplify six target sequences. A pair of common primers was used in combination with each pair of the specific primers. Total six amplification reactions plus one no-specific primer control were conducted in six tubes. The compositions of the reaction mixtures are listed below.

TABLE 5

Reaction mixture compositions

| | Units | Tube 1-6 | Tube 7 |
|---|---|---|---|
| Specific Primer (specPrm1, specPrm2) | nM (per primer) | 1 | |
| Common primer (comPrm1, comPrm2) | nM (per primer) | 500 | 500 |
| Template - human gDNA | fM | 2 | 2 |
| Phusion Hot Start Flex 2X Master Mix | X | 1 | 1 |
| Total volume | μL | 25 | 25 |

Thermo cycling reactions were performed on Thermal Cycler DNA Engine Tetrad (from Bio-Rad, Hercules, Calif.) using the temperature program shown below.

TABLE 6

Relay PCR temperature program

| Step | | Temp (° C.) | Time |
|---|---|---|---|
| Activation | 1 | 98 | 5 min |
| Denature | 2 | 98 | 15 sec |
| Specific primer annealing | 3 | 65 | 120 min |
| Extension 1 | 4 | 68 | 120 sec |
| Extension 2 | 5 | 72 | 120 sec |
| GOTO 2 for 1 time | 6 | | |
| Denature | 7 | 98 | 15 sec |
| Initiatial common primer anealing | 8 | 60 | 30 sec |
| Extension 1 | 9 | 68 | 120 sec |
| Extension 2 | 10 | 72 | 120 sec |
| GOTO 7 for 1 time | 11 | | |
| Denature | 12 | 98 | 15 sec |
| Extension 1 | 13 | 68 | 120 sec |
| Extension 2 | 14 | 72 | 120 sec |
| GOTO 12 for 25 times | 15 | | |
| Extension | 16 | 72 | 10 min |
| Hold | 17 | 4 | Forever |

Specific primer sequence information is listed below.

TABLE 7

Specific primer sequence information

| index | prmName | rxtTube | tgtChr | tgtStrand | prmStrand | tgtStart/End | tgtLength | ampliconLength |
|---|---|---|---|---|---|---|---|---|
| 1 | TP53_31_59_tile03_O1 | 1 | chr17 | + | − | 7578615 | | |
| 2 | TP53_31_59_tile03_O2 | 1 | chr17 | + | + | 7578439 | 176 | 293 |
| 3 | TP53_31_59_tile01_O1 | 2 | chr17 | + | − | 7578353 | | |
| 4 | TP53_31_59_tile01_O2 | 2 | chr17 | + | + | 7578162 | 191 | 308 |
| 5 | PIK3CA12_tile01_O1 | 3 | chr3 | + | − | 178938982 | | |
| 6 | PIK3CA12_tile01_O2 | 3 | chr3 | + | + | 178938809 | 173 | 290 |
| 7 | KRAS1_tile01_O1 | 4 | chr12 | − | + | 25378405 | | |
| 8 | KRAS1_tile01_O2 | 4 | chr12 | − | − | 25378595 | 190 | 307 |
| 9 | APC1_tile01_O1 | 5 | chr5 | − | + | 112173871 | | |
| 10 | APC1_tile01_O2 | 5 | chr5 | − | − | 112174042 | 171 | 288 |
| 11 | APC2_tile01_O1 | 6 | chr5 | − | + | 112174557 | | |
| 12 | APC2_tile01_O2 | 6 | chr5 | − | − | 112174730 | 173 | 290 |

TABLE 8

Primer sequence list

| index | prmSeq |
|---|---|
| 1 | CGCATGTTTGTTTCTTTGCTGCCGTCTTCCAGGTTCAGAGTTCTACAGTCCGACGATCTTGCTTTATCTGTTCACTTGTG SEQ ID NO: 5 |
| 2 | ACAACCTCCGTCATGTGCTGTGACTGCTCCTTGGCACCCGAGAATTCCATGTAGATGGCCATGGC SEQ ID NO: 6 |
| 3 | GCGATGGTGAGCAGCTGGGGCTGGGTTCAGAGTTCTACAGTCCGACGATCAGAGACGACAGGGC SEQ ID NO: 7 |
| 4 | CCCTTAACCCCTCCTCCCAGAGACCCCACCTTGGCACCCGAGAATTCCAGTTGCAAACCAGACCT SEQ ID NO: 8 |
| 5 | GGGCTTCTAAACAACTCTGCCCCACTGCAGGTTCAGAGTTCTACAGTCCGACGATCTGAAAAGAGTCTCAAACACAAAC SEQ ID NO: 9 |
| 6 | CTTTTAGATCTGAGATGCACAATAAAACAGTTAGCCAGAGGTTCCTTGGCACCCGAGAATTCCATGGCCTGCTTTTGG SEQ ID NO: 10 |
| 7 | CCAAAAGCAGTACCATGGACACTGGATTAAGAAGCAATGGTTCAGAGTTCTACAGTCCGACGATCCCCTCTCAAGAGACAAAAACA SEQ ID NO: 11 |
| 8 | AACAGTAGACACAAAACAGGCTCAGGACTTAGCAACCTTGGCACCCGAGAATTCCAGAAGTTATGGAATTCCTTTTATTGAAACA SEQ ID NO: 12 |

TABLE 8-continued

Primer sequence list

| index | prmSeq |
|---|---|
| 9 | AGATAGAAGTTTGGAGAGAGAACGCGGAATTGGTCTAGTTCAGAGTTCTACAGTCCGACGATCGGCAACTACCATCCAGC SEQ ID NO: 13 |
| 10 | GGGCAGCAGAGCTTCTTCTAAGTGCATTTCTCTCACCTTGGCACCCGAGAATTCCATCTGTCACACAATGTAATTCAGT SEQ ID NO: 14 |
| 11 | CCTGTTTATACTGAGAGCACTGATGATAAACACCTCAAGTTGTTCAGAGTTCTACAGTCCGACGATCCCAACCACATTTTGGACAG SEQ ID NO: 15 |
| 12 | GTTGGTCTCTCTTCTTCTTCATGCTGTTCTTCTTCAGAGTACCTTGGCACCCGAGAATTCCAACGTTCACTATAATTGGTAGGC SEQ ID NO: 16 |

The common primers that were used were the same as that of Experiment I. PCR products were analyzed using the same agarose gel electrophoresis method as that of Experiment I. FIG. 16 shows the gel image. Lane 1 through lane 6 shows the products from the six individual PCR reactions. Lane 7 shows the result of no-specific primer control run. Lane L is a DNA ladder showing the sizes (in base pair or bp) of corresponding markers. In all six tubes, PCR products of expected sizes were obtained. The following table shows the relative signals of product bands in the gel image. The standard deviation of the relative signals is 0.191. The gel signal values were extracted from the gel image using Array-Pro® analyzer software (from MediaCybernetics, Rockville, Md.). The relative signals are derived by dividing signals by signal median. No detectable PCR product is observed in the no-specific primer experiment of lane 7.

TABLE 9

Relative signals of product bands

| rxtTube | TgtName | Signal (mean) | Relative Signal |
|---|---|---|---|
| 1 | TP53-T3 | 9,049 | 0.68 |
| 2 | TP53-T1 | 13,948 | 1.04 |
| 3 | PIK3CA12-T1 | 16,866 | 1.26 |
| 4 | KRAS1-T1 | 11,912 | 0.89 |

TABLE 9-continued

Relative signals of product bands

| rxtTube | TgtName | Signal (mean) | Relative Signal |
|---|---|---|---|
| 5 | APC1-T1 | 13,707 | 1.02 |
| 6 | APC2-T1 | 13,094 | 0.98 |

Example III

Multiplex PCR to Amplify all Six Targets of Experiment II in a Single Tube

The same six pairs of omega primers and one pair of common primers as that of Experiment II were used. The composition of the reaction mixtures is shown below.

TABLE 10

Reaction mixture compositions

| | Units | Tube 1 |
|---|---|---|
| Specific Primer (12 primers) | nM (per primer) | 1 |
| Common primer (comPrm1, comPrm2) | nM (per primer) | 500 |
| Template - human gDNA | fM | 2 |
| Phusion Hot Start Flex 2X Master Mix | X | 1 |
| Total volume | µL | 25 |

Thermo cycling reactions were performed on Thermal Cycler DNA Engine Tetrad (from Bio-Rad, Hercules, Calif.) using the temperature program shown below.

TABLE 11

Relay PCR temperature program

| | Step | Temp (° C.) | Time |
|---|---|---|---|
| Activation | 1 | 98 | 5 min |
| Denature | 2 | 98 | 15 sec |
| Specific primer annealing | 3 | 65 | 120 min |
| Extension 1 | 4 | 68 | 60 sec |
| Extension 2 | 5 | 72 | 60 sec |
| GOTO 2 for 1 time | 6 | | |
| Denature | 7 | 98 | 15 sec |
| Initiatial common primer anealing | 8 | 60 | 30 sec |
| Extension 1 | 9 | 68 | 60 sec |
| Extension 2 | 10 | 72 | 60 sec |
| GOTO 7 for 1 time | 11 | | |
| Denature | 12 | 98 | 15 sec |
| Extension 1 | 13 | 68 | 60 sec |
| Extension 2 | 14 | 72 | 60 sec |
| GOTO 12 for 25 times | 15 | | |
| Extension | 16 | 72 | 10 min |
| Hold | 17 | 4 | Forever |

PCR products were analyzed using the same agarose gel electrophoresis method as that of Experiment I. FIG. 18A shows the gel image. Lane 1 shows the product of the multiplex PCR. Lane L is a DNA ladder showing the sizes (in base pair or bp) of corresponding markers. The size distribution of the PCR product is in the expected size range of 288 to 308 bp. The multiplex PCR product was also analyzed by parallel sequencing using HiSeq 2000 (from Illumina, San Diego, Calif.). All six expected amplicons produced sequencing reads. The following table shows the read number distribution of individual amplicons of the target sequences. In the table, read fraction is calculated by dividing the read number of each target sequence by the total number of reads. Relative read fraction is calculated by dividing the read fraction by median value of the read fraction. All 6 amplicons had read number above 20% of median read numbers. The standard deviation of the relative read fraction is 0.512. FIG. 18B shows a scatter plot of the sequencing read number distribution of the 6 expected amplicons.

TABLE 12

Sequencing derived read number distribution of individual amplicons

| rxtTube | TgtName | Read Number | Read Fraction | Relative Read Fraction |
|---|---|---|---|---|
| 1 | TP53-T3 | 152,832 | 0.12 | 0.86 |
| 2 | TP53-T1 | 211,454 | 0.16 | 1.14 |
| 3 | PIK3CA12-T1 | 354,681 | 0.28 | 2.00 |
| 4 | KRAS1-T1 | 135,307 | 0.10 | 0.71 |
| 5 | APC1-T1 | 271,654 | 0.21 | 1.50 |
| 6 | APC2-T1 | 134,248 | 0.10 | 0.71 |

Example IV

Multiplex PCR Using Omega Primers to Amplify 44 Targets in a Single Tube

A multiplex relay PCR using omega primer in a single tube was performed to capture and amplify 44 targets in human genomic DNA. The amplicon distribution in the PCR product was obtained by sequencing using HiSeq 2000 (from Illumina, San Diego, Calif.) sequencer. 88 omega primers were designed to capture 44 specific target regions of human genome according to the disclosed primer design and computation methods. Genome assembly version GRCh37/hg19 was used in the used in the target/primer design. The information of the captured regions is listed in the following table. In the table, we call the capture region including 3p arm segments of omega primers as "probe" (prb). The last two columns of the table list the indexes of paired primers. The omega specific primer sequences were designed according to the design methods of this disclosure and the common primers were the same as those of Experiment I.

TABLE 13

List of the captured regions

| index | prbIndex | ampliconID | geneName | chr | prbStart | prbEnd | prm1Idx | prm2Idx |
|---|---|---|---|---|---|---|---|---|
| 1 | prb_2 | ERBB4_3_4_chr2_212530002_175_140509-1_t2 | ERBB4_3_4 | chr2 | 212530002 | 212530176 | prm_3 | prm_4 |
| 2 | prb_6 | ERBB4_9_chr2_212589687_190_140509-1_t2 | ERBB4_9 | chr2 | 212589687 | 212589876 | prm_11 | prm_12 |
| 3 | prb_8 | ERBB4_11_chr2_212812087_198_140509-1_t2 | ERBB4_11 | chr2 | 212812087 | 212812284 | prm_15 | prm_16 |
| 4 | prb_10 | VHL3_5_chr3_10188197_183_140509-1_t2 | VHL3_5 | chr3 | 10188197 | 10188379 | prm_19 | prm_20 |
| 5 | prb_11 | VHL6_8_chr3_10191403_171_140509-1_t2 | VHL6_8 | chr3 | 10191403 | 10191573 | prm_21 | prm_22 |
| 6 | prb_15 | PIK3CA4_11_chr3_178936054_189_140503-1_t2 | PIK3CA4_11 | chr3 | 178936054 | 178936242 | prm_29 | prm_30 |

TABLE 13-continued

List of the captured regions

| index | prbIndex | ampliconID | geneName | chr | prbStart | prbEnd | prm1Idx | prm2Idx |
|---|---|---|---|---|---|---|---|---|
| 7 | prb_16 | PIK3CA12_chr3_178938706_188_140503-1_t2 | PIK3CA12 | chr3 | 178938706 | 178938893 | prm_31 | prm_32 |
| 8 | prb_18 | PIK3CA13_20_chr3_178952024_175_140503-1_t2 | PIK3CA13_20 | chr3 | 178952024 | 178952198 | prm_35 | prm_36 |
| 9 | prb_20 | APC2_chr5_112174500_190_140503-1_t2 | APC2 | chr5 | 112174500 | 112174689 | prm_39 | prm_40 |
| 10 | prb_22 | APC3_42_chr5_112175257_185_140503-1_t2 | APC3_42 | chr5 | 112175257 | 112175441 | prm_43 | prm_44 |
| 11 | prb_24 | APC3_42_chr5_112175519_186_140503-1_t2 | APC3_42 | chr5 | 112175519 | 112175704 | prm_47 | prm_48 |
| 12 | prb_26 | APC3_42_chr5_112175778_187_140503-1_t2 | APC3_42 | chr5 | 112175778 | 112175964 | prm_51 | prm_52 |
| 13 | prb_28 | EGFR1_chr7_55211035_171_140503-1_t2 | EGFR1 | chr7 | 55211035 | 55211205 | prm_55 | prm_56 |
| 14 | prb_29 | EGFR2_chr7_55221780_171_140503-1_t2 | EGFR2 | chr7 | 55221780 | 55221950 | prm_57 | prm_58 |
| 15 | prb_30 | EGFR3_chr7_55232965_170_140503-1_t2 | EGFR3 | chr7 | 55232965 | 55233134 | prm_59 | prm_60 |
| 16 | prb_31 | EGFR4_chr7_55241618_180_140503-1_t2 | EGFR4 | chr7 | 55241618 | 55241797 | prm_61 | prm_62 |
| 17 | prb_32 | EGFR9_chr7_55242352_190_140503-1_t2 | EGFR9 | chr7 | 55242352 | 55242541 | prm_63 | prm_64 |
| 18 | prb_33 | EGFR44_chr7_55248978_177_140503-1_t2 | EGFR44 | chr7 | 55248978 | 55249154 | prm_65 | prm_66 |
| 19 | prb_34 | EGFR54_chr7_55259367_173_140503-1_t2 | EGFR54 | chr7 | 55259367 | 55259539 | prm_67 | prm_68 |
| 20 | prb_37 | PTEN3_chr10_89685268_190_140503-1_t2 | PTEN3 | chr10 | 89685268 | 89685457 | prm_73 | prm_74 |
| 21 | prb_38 | PTEN4_chr10_89711829_184_140503-1_t2 | PTEN4 | chr10 | 89711829 | 89712012 | prm_75 | prm_76 |
| 22 | prb_40 | PTEN7_chr10_89717703_187_140503-1_t2 | PTEN7 | chr10 | 89717703 | 89717889 | prm_79 | prm_80 |
| 23 | prb_43 | ATM2_chr11_108119751_197_140509-1_t2 | ATM2 | chr11 | 108119751 | 1081199475 | prm_85 | prm_86 |
| 24 | prb_44 | ATM3_chr11_108123509_218_140509-1_t2 | ATM3 | chr11 | 108123509 | 108123726 | prm_87 | prm_88 |
| 25 | prb_47 | ATM7_chr11_108170341_193_140509-1_t2 | ATM7 | chr11 | 108170341 | 108170533 | prm_93 | prm_94 |
| 26 | prb_49 | ATM10_chr11_108173612_206_140509-1_t2 | ATM10 | chr11 | 108173612 | 108173817 | prm_97 | prm_98 |
| 27 | prb_53 | ATM15_chr11_108205687_168_140509-1_t2 | ATM15 | chr11 | 108205687 | 108205854 | prm_105 | prm_106 |
| 28 | prb_54 | ATM16_chr11_108206455_168_140509-1_t2 | ATM16 | chr11 | 108206455 | 108206622 | prm_107 | prm_108 |
| 29 | prb_56 | ATM18_chr11_108225561_176_140509-1_t2 | ATM18 | chr11 | 108225561 | 108225736 | prm_111 | prm_112 |
| 30 | prb_57 | ATM19_chr11_108236033_185_140509-1_t2 | ATM19 | chr11 | 108236033 | 108236217 | prm_113 | prm_114 |
| 31 | prb_61 | FLT3_1_chr13_28592542_171_140509-1_t2 | FLT3_1 | chr13 | 28592542 | 28592712 | prm_121 | prm_122 |
| 32 | prb_62 | FLT3_13_chr13_28602179_187_140509-1_t2 | FLT3_13 | chr13 | 28602179 | 28602365 | prm_123 | prm_124 |
| 33 | prb_64 | FLT3_22_chr13_28610028_170_140509-1_t2 | FLT3_22 | chr13 | 28610028 | 28610197 | prm_127 | prm_128 |
| 34 | prb_66 | BRCA2_chr13_32907302_179_140509-1_t2 | BRCA2 | chr13 | 32907302 | 32907480 | prm_131 | prm_132 |
| 35 | prb_69 | BRCA2_chr13_32912508_181_140509-1_t2 | BRCA2 | chr13 | 32912508 | 32912688 | prm_137 | prm_138 |
| 36 | prb_70 | BRCA2_chr13_32920892_196_140509-1_t2 | BRCA2 | chr13 | 32920892 | 32921087 | prm_139 | prm_140 |
| 37 | prb_74 | BRCA2_chr13_32954042_188_140509-1_t2 | BRCA2 | chr13 | 32954042 | 32954229 | prm_147 | prm_148 |
| 38 | prb_75 | BRCA2_chr13_32970885_203_140509-1_t2 | BRCA2 | chr13 | 32970885 | 32971087 | prm_149 | prm_150 |
| 39 | prb_76 | BRCA2_chr13_32972487_199_140509-1_t2 | BRCA2 | chr13 | 32972487 | 32972685 | prm_151 | prm_152 |
| 40 | prb_82 | TP53_60_chr17_7579298_187_140503-1_t2 | TP53_60 | chr17 | 7579298 | 7579484 | prm_163 | prm_164 |
| 41 | prb_85 | ERBB2_4_chr17_37880908_176_140509-1_t2 | ERBB2_4 | chr17 | 37880908 | 37881083 | prm_169 | prm_170 |
| 42 | prb_86 | ERBB2_13_chr17_37881235_220_140509-1_t2 | ERBB2_13 | chr17 | 37881235 | 37881454 | prm_171 | prm_172 |
| 43 | prb_87 | BRCA1_chr17_41243526_181_140509-1_t2 | BRCA1 | chr17 | 41243526 | 41243706 | prm_173 | prm_174 |
| 44 | prb_92 | BRCA1_chr17_41267714_178_140509-1_t2 | BRCA1 | chr17 | 41267714 | 41267891 | prm_183 | prm_184 |

The composition of the reaction mixtures is shown below.

TABLE 14

Reaction mixture compositions

| | Units | Tube A | Tube B | Tube C |
|---|---|---|---|---|
| Specific Primer (88 primers) | nM (per primer) | 1 | 0.2 | 0.04 |
| Common primer (comPrm1, comPrm2) | nM (per primer) | 500 | 500 | 500 |
| Template - human gDNA | fM | 2 | 2 | 2 |
| Phusion Hot Start Flex 2X Master Mix | X | 1 | 1 | 1 |
| Total volume | µL | 25 | 25 | 25 |

Thermo cycling reactions were performed on Thermal Cycler DNA Engine Tetrad (from Bio-Rad, Hercules, Calif.) using the temperature program shown below.

TABLE 15

Relay PCR temperature program

| | Step | Temp (° C.) | Time |
|---|---|---|---|
| Activation | 1 | 98 | 5 min |
| Denature | 2 | 98 | 15 sec |
| Specific primer annealing | 3 | 65 | 120 min |
| Extension 1 | 4 | 68 | 60 sec |
| Extension 2 | 5 | 72 | 60 sec |
| GOTO 2 for 1 time | 6 | | |
| Denature | 7 | 98 | 15 sec |
| Initiatial common primer anealing | 8 | 60 | 30 sec |
| Extension 1 | 9 | 68 | 60 sec |
| Extension 2 | 10 | 72 | 60 sec |
| GOTO 7 for 1 time | 11 | | |
| Denature | 12 | 98 | 15 sec |
| Extension 1 | 13 | 68 | 60 sec |
| Extension 2 | 14 | 72 | 60 sec |
| GOTO 12 for 25 times | 15 | | |
| Extension | 16 | 72 | 10 min |
| Hold | 17 | 4 | Forever |

The multiplex PCR products were analyzed by parallel sequencing using HiSeq 2000 (from Illumina, San Diego, Calif.). FIG. 19 shows the sequencing measurement results of amplicon read number distributions. Figures A, B, and C plot the results obtained by using specific omega primer concentrations of 1 nM, 0.2 nM, and 0.04 nM per primer, respectively. All 44 designed target regions produced amplicons as observed in the sequencing result. More than 95% the amplicons had read number above 20% of median read numbers in PCR products from all three specific omega primer concentrations.

Example V

Relay PCR and Annealing Time

An experiment was conducted to reveal the relay PCR yield dependence on phase I specific primer annealing time at specific primer concentrations of 5 nM and 1 nM, respectively. The composition of the reaction mixtures is shown below.

TABLE 16

Reaction mixture compositions

| | Units | Tubes 1-5 | Tubes 6-10 |
|---|---|---|---|
| Specific Primer (APC1_R1, APC1_R2) | nM (per primer) | 5 | 1 |
| Common primer (comPrm1, comPrm2) | nM (per primer) | 500 | 500 |
| Template—human gDNA | fM | 2 | 2 |
| Phusion Hot Start Flex 2X Master Mix | X | 1 | 1 |
| Total volume | µL | 25 | 25 |
| Specific primer annealing time | min | 10-240 | 10-240 |

Specific primer sequences are list below. Common primers were the same as those of Example I.

TABLE 17

List of primer sequences

| Primer Name | Primer Sequence 5' to 3' |
|---|---|
| APC1_R1 | GTTCAGAGTTCTACAGTCCGACGATCGAGAG AACGCGGAATTGGTCTAGGCA SEQ ID NO: 17 |
| APC1_R2 | CCTTGGCACCCGAGAATTCCAAGTGGTAGAC CCAGAACTTCTGTCTTCCT SEQ ID NO: 18 |

Thermo cycling reactions were performed on Thermal Cycler DNA Engine Tetrad (from Bio-Rad, Hercules, Calif.) using the temperature program shown below.

TABLE 18

Relay PCR temperature program

| Step | | Temp (° C.) | Time | |
|---|---|---|---|---|
| Activation | 1 | 98 | 5 | min |
| Denature | 2 | 98 | 15 | sec |
| Specific primer annealing | 3 | 65 | 10, 30, 60, 120, 240 | min |
| Extension | 4 | 72 | 30 | sec |
| GOTO 2 for 1 time | 5 | | | |
| Denature | 6 | 98 | 15 | sec |
| Initiatial common primer anealing | 7 | 60 | 30 | sec |
| Extension | 8 | 72 | 30 | sec |
| GOTO 6 for 1 time | 9 | | | |
| Denature | 10 | 98 | 15 | sec |
| Extension | 11 | 72 | 30 | sec |
| GOTO 10 for 25 times | 12 | | | |
| Extension | 13 | 72 | 10 | min |
| Hold | 14 | 4 | Forever | |

PCR products were analyzed using the same agarose gel electrophoresis method as that of Experiment I. In all 10 tubes, PCR products of expected size (288 bp) were obtained. The following table shows the signals and relative signals of product bands extracted from the gel image. The gel signal values were extracted by using Array-Pro® analyzer software (from MediaCybernetics, Rockville, Md.). The relative signals are derived by dividing corresponding signals by the maximum signal within the same specific primer concentration. From the data, it is noted that at high specific primer concentration of 5 nM, relative signal rapidly reaches a high relative signal of 0.7 within a short specific primer annealing time of 10 min. However, at a low specific concentration of 1 nM, a significantly extended specific primer annealing time of 60 min or more is required to obtain a relative signal approaching 1.

TABLE 19

Product band signals

| Specific primer annealing time (min) | Signal (mean) | Relative Signal | Specific primer conc (nM) |
|---|---|---|---|
| 10 | 9,488 | 0.70 | 5 |
| 30 | 13,607 | 1.00 | 5 |
| 60 | 8,175 | 0.60 | 5 |
| 120 | 9,050 | 0.67 | 5 |
| 240 | 5,795 | 0.43 | 5 |
| 10 | 2 | 0.00 | 1 |
| 30 | 2,211 | 0.37 | 1 |
| 60 | 4,973 | 0.84 | 1 |
| 120 | 5,887 | 1.00 | 1 |
| 240 | 5,909 | 1.00 | 1 |

Example VI

Multiplex Relay PCR Using Microarray Synthesized Specific Primer Precursors

An experiment was conducted to practice multiplex relay PCR using microarray synthesized specific primer precursors. The method of this experiment has been described in the exemplary embodiment relating to FIG. 9 of this disclosure.

A group of 204 omega primer precursor sequences for capturing 102 specific target regions in human genome were designed according to the design methods of this disclosure. All omega primer precursor sequences have the same 5' and 3' flank segments for PCR amplification use. Following table lists two exemplary omega primer precursor sequences (2 out of 204) and two preparation primer sequences. As describe earlier in this disclosure, preparation primer prep-Prm2 has a dU at its 3' terminal. The 204 omega primer precursor sequences were synthesized using microarray synthesis method and the two preparation primers were synthesized using conventional oligonucleotide synthesis method. All 204 omega primer precursor sequences were synthesized in parallel and provided by the manufacture LC Sciences (Houston, Tex.) in a mixture form and in a single tube.

TABLE 20

List of primer sequences

| Sequence Name | Sequence 5' to 3' |
|---|---|
| MPL1_2_tile01_prm1_tube1 | GAGCTTCGGTTCACGCAATGCCGAAGTCTGACC CTTTTTGTCTCCTAGCCGTTCAGAGTTCTACAG TCCGACGATCTGGATCTCCTTGGTAGTTGATCC GGTCCTAGGCA SEQ ID NO: 19 |
| MPL1_2_tile01_prm2_tube1 | GAGCTTCGGTTCACGCAATGACGGAGATCTGGG GTCACAGAGCGACCTTGGCACCCGAGAATTCCA ACCAAGAATGCCTAGTTGATCCGGTCCTAGGCA SEQ ID NO: 20 |

TABLE 20-continued

List of primer sequences

| Sequence Name | Sequence 5' to 3' |
|---|---|
| prepPrm1 | GAGCTTCGGTTCACGCAATG SEQ ID NO: 21 |
| prepPrm2 | TGCCTAGGACCGGATCAAC/dU/ SEQ ID NO: 22 |

The omega primer precursor sequence mixture was first amplified by PCR using Taq hot start 2X master mix (from NEB, Ipswich, Mass.). The PCR reaction mixture composition is shown below.

TABLE 21

Reaction mixture compositions

| | Units | Tube 1 |
|---|---|---|
| Common primer (prepPrm1, prepPrm2) | nM (per primer) | 500 |
| Template-omega primer precursor mix | pM | 1 |
| Taq Hot Start 2X Master Mix | X | 1 |
| Total volume | µL | 25 |

Thermo cycling reactions were performed on Thermal Cycler DNA Engine Tetrad (from Bio-Rad, Hercules, Calif.). PCR temperature program is shown below.

TABLE 22

PCR temperature program

| | Step | Temp (° C.) | Time |
|---|---|---|---|
| Activation | 1 | 95 | 5 min |
| Denaturatoin | 2 | 95 | 30 sec |
| Annealing | 3 | 60 | 60 sec |
| Extension | 4 | 68 | 60 sec |
| GOTO 2 for 10 time | 5 | | |
| Extension | 6 | 72 | 10 min |
| Hold | 7 | 4 | Forever |

PCR products were analyzed using the same agarose gel electrophoresis method as that of Experiment I. FIG. 20A lane 1 shows the agarose gel electrophoresis image of the PCR product. PCR product of the expected size distribution of 95-130 bp with a median size of 110 bp was observed. The PCR product of the omega primer precursors was purified using PCR purification beats (Agencourt AMPure XP system from Beckman Coulter, Brea, Calif.) by following manufacture instruction. Concentration of the purified PCR product was measured by Bioanalyzer from Agilent (Santa Clara, Calif.).

Then, dU in the PCR product was removed using UDG/EDA process. A UDG digestion solution is prepared according to the following table. UDG and UDG buffer were purchased from NEB (Ipswich, Mass.). The solution was incubated at 37° C. for 60 minutes. Then, 2 µL 200 mM EDA (from Sigma-Aldrich, St. Louis, Mo.) was added into the solution and incubated at 37° C. for another 60 minutes.

TABLE 23

Reaction mixture composition

| | Units | Tube 1 |
|---|---|---|
| Total volume | µL | 10 |
| PCR product | µL | 8 |

TABLE 23-continued

Reaction mixture composition

| | Units | Tube 1 |
|---|---|---|
| UDG (5U/ul) | µL | 1 |
| UDG buffer, 10× | µL | 1 |

Relay PCR using the amplified and dU removed specific primer precursors was carried out using human genomic DNA as template and Phusion Hot Start Flex polymerase Master Mix (from NEB, Ipswich, Mass.) as polymerase. The compositions of individual reaction components are listed below. Reaction in tube 1 is a negative control without adding the specific primer precursor. Reaction in tube 2 is the test for the relay PCR.

TABLE 24

Reaction mixture composition

| | Units | Tube 1 | Tube 2 |
|---|---|---|---|
| Specific primer precursors | nM (total) | | 1.4 |
| prepPrm1 | nM | 200 | 200 |
| Common primers (comPrm1, comPrm2) | nM (per primer) | 500 | 500 |
| Template-Human gDNA | fM | 2 | 2 |
| Phusion Hot Start Flex 2X Master Mix | X | 1 | 1 |
| Total volume | µL | 25 | 25 |

Thermo cycling reactions were performed on Thermal Cycler DNA Engine Tetrad (from Bio-Rad, Hercules, Calif.). PCR temperature program is shown below.

TABLE 25

Relay PCR temperature program

| | Step | Temp (° C.) | Time |
|---|---|---|---|
| Activation | 1 | 98 | 5 min |
| Annealing | 2 | 68 | 1 min |
| Extension | 3 | 72 | 1 min |
| Denature | 4 | 98 | 15 sec |
| Annealing | 5 | 65 | 120 min |
| Extension | 6 | 72 | 30 sec |
| GOTO 4 for 1 time | 7 | | |
| Denature | 8 | 98 | 15 sec |
| Annealing | 9 | 60 | 30 sec |
| Extension | 10 | 72 | 30 sec |
| GOTO 8 for 1 time | 11 | | |
| Denature | 12 | 98 | 15 sec |
| Extension | 13 | 72 | 30 sec |
| GOTO 12 for 25 times | 14 | | |
| Extension | 15 | 72 | 10 min |
| Hold | 16 | 4 | Forever |

Products of the relay PCR were analyzed using the same agarose gel electrophoresis method as that of Experiment I. FIG. 20B shows the images of the PCR products. Lane L is a DNA ladder showing the sizes (in base pair or bp) of corresponding markers. Lane 1 shows the result of the negative control of tube 1. No PCR product is observed in the negative control (lower bands are due to unused primers). Lane 2 is loaded with the PCR product from tube 2. An expected PCR product size distribution of 295-399 bp with a median of 317 bp was observed.

Example VII

Multiplex Relay PCR Using Specific Primers Prepared by PCR Amplification

An experiment was conducted to practice multiplex relay PCR using specific primers prepared by PCR amplification. The method of this experiment has been described in the exemplary embodiment relating to FIG. 11 of this disclosure.

Omega primers for capturing a target region in human genome of genome assembly version GRCh37/hg19 were designed according to the design methods of this disclosure. The captured target region belongs to an exon region of APC1 gene in chromosome 5 and with starting position of 112,173,776 and ending position of 112,173,955. The following table lists the oligonucleotide sequences used in this experiment. Preparation primers prepPrm1 and prepPrm2 are designed to PCR amplify specific primer templates. A restriction recognition site GCTCTTC is embedded in prepPrm2 sequence to facilitate restriction cut of the PCR product by restriction nuclease BspQI. Specific primer templates APC1_chr5_112173790_p1 and APC1_chr5_112173944_p2 containing 5' as well as 3' flanking segments are designed to be PCR amplified by prepPrm1 and prepPrm2. The mid-section of the specific primer templates are designed as omega primers. Specific primers APC1_chr5_112173790_p1_no3pFlank and APC1_chr5_112173944_p2_no3pFlank have the same omega primer designs as that of APC1_chr5_112173790_p1 and APC1_chr5_112173944_p2 but do not have 3' flank segments. They are active specific primers and were used as references to be compared with specific primer template derived primers for capturing the target region in relay PCR reactions. Primers comPrm1 and comPrm2 were designed as common primers of relay PCR. The oligonucleotides in the following table were synthesized using conventional method and were provided by LC Sciences (Houston, Tex.).

TABLE 26

List of primer sequences

| Sequence Name | Sequence 5' to 3' |
| --- | --- |
| prepPrm1 | TTTTCGCGTTAGTATCCGACCGATCTACGTAGCG SEQ ID NO: 23 |
| prepPrm2 | TTTTGACCGTACTATCGAACCGTCGTACTAGCTC TTCGCGT SEQ ID NO: 24 |
| APC1_chr5_ 112173790_p1 | ATCCGACCGATCTACGTAGCGGGCAACATGACTG TCCTTTCACCATATTTGAATACTCGTTCAGAGTT CTACAGTCCGACGATCACAGTGTTACCCAGCACG CGAAGAGCTAGTACGACGG SEQ ID NO: 25 |
| APC1_chr5_ 112173944_p2 | ATCCGACCGATCTACGTAGCGGGTATGAATGGCT GACACTTCTTCCATGACTTTCCTTGGCACCCGAG AATTCCAGGCAATCTGGGCACGCGAAGAGCTAGT ACGACGG SEQ ID NO: 26 |
| APC1_chr5_ 112173790_ p1_no_p3 flank | TCCGACCGATCTACGTAGCGGGCAACATGACTGT CCTTTCACCATATTTGAATACTCGTTCAGAGTTC TACAGTCCGACGATCACAGTGTTACCCAGC SEQ ID NO: 27 |
| APC1_chr5_ 112173944_ p1_no_p3 flank | TCCGACCGATCTACGTAGCGGGTATGAATGGCTG ACACTTCTTCCATGACTTTCCTTGGCACCCGAGA ATTCCAGGCAATCTGGGC SEQ ID NO: 28 |
| comPrm1 | AATGATACGGCGACCACCGAGATCTACACATGAT GACACACGTTCAGAGTTCTACAGTCCGA SEQ ID NO: 29 |

TABLE 26-continued

List of primer sequences

| Sequence Name | Sequence 5' to 3' |
| --- | --- |
| comPrm2 | CAAGCAGAAGACGGCATACGAGATGAATGATAGT GACTGGAGTTCCTTGGCACCCGAGAATTCCA SEQ ID NO: 30 |

To amplify the specific primer templates, the two specific primer templates were mixed in equal concentration together with PCR components as shown in the table below. Hot start Phusion polymerase from (from NEB, Ipswich, Mass.) was used in this reaction.

TABLE 27

Reaction mixture composition

|  | Units | Tube 1 |
| --- | --- | --- |
| Preparation primer (prepPrm1, prepPrm2) | nM (per primer) | 500 |
| Template (APC1_chr5_112173790_p1) | fM | 20 |
| Template (APC1_chr5_112173944_p2) | fM | 20 |
| Hot Start Phusion Flex 2X Master Mix | X | 1 |
| Total volume | µL | 25 |

Thermo cycling reactions were performed on Thermal Cycler DNA Engine Tetrad (from Bio-Rad, Hercules, Calif.). PCR temperature program is shown below.

TABLE 28

PCR temperature program

|  | Step | Temp (° C.) | Time |
| --- | --- | --- | --- |
| Activation | 1 | 98 | 5 min |
| Denature | 2 | 98 | 15 sec |
| Annealing | 3 | 70 | 30 sec |
| Extension | 4 | 72 | 60 sec |
| GOTO 2 for 1 time | 5 |  |  |
| Denature | 6 | 98 | 15 sec |
| Annealing-Extension | 7 | 72 | 60 sec |
| GOTO 6 for 19 time | 8 |  |  |
| Extension | 9 | 72 | 10 min |
| Hold | 10 | 4 | Forever |

The PCR product was analyzed using the same agarose gel electrophoresis method as that of Experiment I. FIG. 21A lane 1 shows the gel image of the PCR products. The predicted sizes of the two PCR products are 153 bp and 141 bp, respectively, and the gel band positions agree with the prediction. The PCR product was purified using PCR purification beats (Agencourt AMPure XP system from Beckman Coulter, Brea, Calif.) by following manufacture instruction. The concentration of the purified PCR product was measured by NanoDrop spectrometer (from NanoDrop products, Wilmington, Del.).

Restriction enzyme digestion was then applied to the PCR product using the reaction compositions shown in the table below. Restriction enzyme BspQI along with 10× Cutsmart buffer was purchased from NEB (Ipswich, Mass.). The digestion reaction was carried out at the enzyme manufacture suggested condition of 50° C. for 30 minutes. The digestion product was then purified using PCR purification beats (Agencourt AMPure XP system from Beckman Coulter, Brea, Calif.) by following manufacture instruction. The purified digestion product was analyzed using the same agarose gel electrophoresis method as that of Experiment I. FIG. 21B lane 2 shows the gel image of the product. The predicted sizes of the two digestion products are 132 bp and 120 bp, respectively, and the gel band positions agree with the prediction. FIG. 21B lane 1 shows the original PCR product before restriction enzyme digestion.

TABLE 29

Reaction mixture composition

|  | Units | Tube 1 |
|---|---|---|
| Purified PCR product (30 ng/uL) | μL | 20 |
| 10x Cutsmart buffer (NEB) | μL | 2.5 |
| BspQI (NEB) | μL | 1 |
| H2O | μL | 1.5 |
| Total volume | μL | 25 |

The restriction enzyme digested product was then subject to Lambda exonuclease digestion to produce single strand specific primer sequences using the reaction compositions shown in the table below. Lambda exonuclease along with a 10× reaction buffer was purchased from NEB (Ipswich, Mass.). The digestion reaction was carried out at the enzyme manufacture suggested condition of 37° C. for 30 minutes. The digestion product was then purified using PCR purification beats (Agencourt AMPure XP system from Beckman Coulter, Brea, Calif.) by following manufacture instruction. We call the product enzymatically prepared specific primers.

TABLE 30

Reaction mixture composition

|  | Units | Tube 1 |
|---|---|---|
| Restriction digested product (20 ng/uL) | μL | 8 |
| 10X Lambda exonuclease reaction buffer | μL | 1 |
| Lambda exonuclease (1000 U/ml) | μL | 1 |
| Total volume | μL | 10 |

Relay PCR reactions using the enzymatically prepared specific primers was carried out using human genomic DNA as template and Phusion Hot Start Flex polymerase Master Mix (from NEB, Ipswich, Mass.) as polymerase. The compositions of individual reaction components are listed in the table below. Reaction in tube 1 is the positive control using reference specific primers APC1_chr5_112173790_p1_no3pFlank and APC1_chr5_112173944_p2_no3pFlank. Reaction in tube 2 is the test using enzymatically prepared specific primers. Reaction in tube 3 is a negative control without adding genomic DNA.

TABLE 31

Reaction mixture composition

|  | Units | Tube 1 | Tube 2 | Tube 3 |
|---|---|---|---|---|
| Specific primer (reference) | nM (per primer) | 1 |  |  |
| Specific primer (enzymatically prepared) | nM (per primer) |  | 1 | 1 |
| Common primers (comPrm1, comPrm2) | nM (per primer) | 500 | 500 | 500 |
| Template-Human gDNA | fM | 1 | 1 |  |
| Hot Start Phusion Flex 2X Master Mix | X | 1 | 1 | 1 |
| Total volume | μL | 25 | 25 | 25 |

Thermo cycling reactions were performed on Thermal Cycler DNA Engine Tetrad (from Bio-Rad, Hercules, Calif.). PCR temperature program is shown below.

TABLE 32

Relay PCR temperature program

|  | Step | Temp (° C.) | Time |
|---|---|---|---|
| Activation | 1 | 98 | 5 min |
| Denature | 2 | 98 | 15 sec |
| Anneal Omega primers | 3 | 65 | 120 min |
| Extension 1 | 4 | 68 | 60 sec |
| Extension 2 | 5 | 72 | 60 sec |
| GOTO 2 for 1 time | 6 |  |  |
| Denature | 7 | 98 | 15 sec |
| Initiate lib primer anealing | 8 | 60 | 30 sec |
| Extension 1 | 9 | 68 | 60 sec |
| Extension 2 | 10 | 72 | 60 sec |
| GOTO 7 for 1 time | 11 |  |  |
| Denature | 12 | 98 | 15 sec |
| Extension 1 | 13 | 68 | 60 sec |
| Extension 2 | 14 | 72 | 60 sec |
| GOTO 12 for 27 times | 15 |  |  |
| Extension | 16 | 72 | 10 min |
| Hold | 17 | 4 | Forever |

Products of the relay PCR were analyzed using the same agarose gel electrophoresis method as that of Experiment I. FIG. 21C shows the images of the PCR products. Lane L is a DNA ladder showing the sizes (in base pair or bp) of corresponding markers. Lane 1 shows the result of the positive control of tube 1 using conventionally synthesized reference specific primers. Lane 2 is the test from tube 2 using enzymatically prepared specific primers. The same product sizes around 300 bp are observed in the positive control of lane 1 and in the test of lane 2. The size is consistent with the predicted size of 312 bp. Lane 3 is the result of negative control from tube 3 which shows no product around 300 bp.

Within this disclosure, any indication that a feature is optional is intended provide adequate support (e.g., under 35 U.S.C. 112 or Art. 83 and 84 of EPC) for claims that include closed or exclusive or negative language with reference to the optional feature. Exclusive language specifically excludes the particular recited feature from including any additional subject matter. For example, if it is indicated that A can be drug X, such language is intended to provide support for a claim that explicitly specifies that A consists of X alone, or that A does not include any other drugs besides X. "Negative" language explicitly excludes the optional feature itself from the scope of the claims. For example, if it is indicated that element A can include X, such language is intended to provide support for a claim that explicitly specifies that A does not include X. Non-limiting examples of exclusive or negative terms include "only," "solely," "consisting of," "consisting essentially of," "alone," "without", "in the absence of (e.g., other items of the same type, structure and/or function)" "excluding," "not including", "not", "cannot," or any combination and/or variation of such language.

Similarly, referents such as "a," "an," "said," or "the," are intended to support both single and/or plural occurrences unless the context indicates otherwise. For example "a dog" is intended to include support for one dog, no more than one dog, at least one dog, a plurality of dogs, etc. Non-limiting examples of qualifying terms that indicate singularity include "a single", "one," "alone", "only one," "not more than one", etc. Non-limiting examples of qualifying terms that indicate (potential or actual) plurality include "at least one," "one or more," "more than one," "two or more," "a multiplicity," "a plurality," "any combination of," "any permutation of," "any one or more of," etc. Claims or descriptions that include "or" between one or more members of a group are considered satisfied if one, more than one, or all of the group members are present in, employed in, or otherwise relevant to a given product or process unless indicated to the contrary or otherwise evident from the context.

Where ranges are given herein, the endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While this invention has been particularly shown and described with references to example embodiments thereof, it will be understood by those skilled in the art that the various changes in form and details may be made therein without departing from the scope of the invention encompassed by the appended claims.

What is claimed is:
1. An isolated nucleic acid consisting of SEQ ID NO: 5.

\* \* \* \* \*